(12) United States Patent
Hanasaki et al.

(10) Patent No.: US 7,183,275 B2
(45) Date of Patent: Feb. 27, 2007

(54) 2-IMINO-1,3-THIAZINE DERIVATIVES

(75) Inventors: Koji Hanasaki, Osaka (JP); Takami Murashi, Osaka (JP); Hiroyuki Kai, Koka-gun (JP)

(73) Assignee: Shionogi Co., Ltd., Osaka (JP)

( * ) Notice: Subject to any disclaimer, the term of this patent is extended or adjusted under 35 U.S.C. 154(b) by 286 days.

(21) Appl. No.: 10/972,414

(22) Filed: Oct. 26, 2004

(65) Prior Publication Data

US 2005/0124617 A1 Jun. 9, 2005

Related U.S. Application Data

(62) Division of application No. 10/069,421, filed as application No. PCT/JP00/06185 on Sep. 11, 2000, now Pat. No. 6,818,640.

(30) Foreign Application Priority Data

Sep. 14, 1999 (JP) ................... 11-260780

(51) Int. Cl.
*A61K 31/54* (2006.01)
*C07D 279/06* (2006.01)
(52) U.S. Cl. .................. 514/227.2; 544/53; 544/54
(58) Field of Classification Search ............. 514/227.2; 544/53, 54
See application file for complete search history.

(56) References Cited

U.S. PATENT DOCUMENTS

| | | | |
|---|---|---|---|
| 3,678,041 A | 7/1972 | Clin-Byla | |
| 4,289,778 A | 9/1981 | Balko | |
| 5,670,530 A | 9/1997 | Chen et al. | |
| 6,713,472 B1 * | 3/2004 | Nishimura et al. | 514/211.15 |
| 6,916,806 B2 * | 7/2005 | Kai et al. | 514/227.2 |
| 6,956,034 B2 * | 10/2005 | Rheinheimer et al. | 514/230.5 |
| 6,960,515 B2 * | 11/2005 | Cho et al. | 438/592 |
| 7,084,137 B2 * | 8/2006 | Bruns et al. | 514/227.2 |

FOREIGN PATENT DOCUMENTS

| | | |
|---|---|---|
| FR | 2 201 080 | 4/1974 |
| JP | 48-23793 | 3/1973 |
| JP | 48-36169 | 5/1973 |
| JP | 50-37775 | 4/1975 |
| JP | 51-54555 | 5/1976 |
| JP | 52-17468 | 2/1977 |
| JP | 52-51364 | 4/1977 |
| JP | 56-10180 | 2/1981 |
| JP | 57-134472 | 8/1982 |
| JP | 59-172486 | 9/1984 |
| JP | 62-212378 | 9/1987 |
| JP | 63-41471 | 2/1988 |
| JP | 2-3678 | 1/1990 |
| JP | 2-223564 | 9/1990 |
| JP | 6-220053 | 8/1994 |
| JP | 11-80124 | 3/1999 |
| WO | 99/29601 | 12/1999 |
| WO | 00/42031 | 7/2000 |
| WO | WO 00/42031 | 7/2000 |
| WO | WO 01/70733 A2 | 9/2001 |

OTHER PUBLICATIONS

Gieldanowski et al., Arch. Immunl. Ther. Exp., 26(1-6), pp. 921-929 (1978).
Gailwad et al., Indian J. Pharm. Sci., 46(5), pp. 170-171 (1984).
Munro et al., NATURE, 365(2), pp. 61-65 (1993).
Database CA "Online" Chemical Abstracts Service, Columbus, OH. Database accession No. 105:208863 XP002208734, Abstract of Mizrakh et al., SU 1 209 689 A (USSR) Feb. 7, 1986.
Database CA "Online" Chemical Abstracts Service, Columbus, OH. Database accession No. 126:277422 XP002208735, Abstract of Malesic et al., Journal of Heterocyclic Chemistry 34(1), 43-48 (1997).
Database CA "Online" Chemical Abstracts Service, Columbus, OH. Database accession No. 121:290104 XP002208736, Abstract of Dianez et al., Acta Crystallagr. Sec. C: Cryst. Struct. Commun. C50(10), 1640-2 (1994).
Database CA "Online" Chemical Abstracts Service, Columbus, OH. Database accession No. 120:217389 XP002208737, Abstract of Avalos et al., Heterocylces 35(2), 1237-46, (1993).
Database CA "Online" Chemical Abstracts Service, Columbus, OH. Database accession No. 105:191000 XP002208738, Abstract of Mizrakh et al., ZH. Obshch. Khim. 56(1), 73-81, (1986).
Database CA "Online" Chemical Abstracts Service, Columbus, OH. Database accession No. 102149160 XP002208739, Abstract of Yamamoto et al., Chem. Pharm. Bull. 32(11), 4292-9, (1984).
Database CA "Online" Chemical Abstracts Service, Columbus, OH. Database accession No. 91:211309 XP002208740, Abstract of Yamamoto et al., Kyoritsu Yakka Daigaku Kenkyu Nempo (23), 38-46, (1978).
Database CA "Online" Chemical Abstracts Service, Columbus, OH. Database accession No. 90:64825 XP002208741, Abstract of Kalman et al., Cryst. Struct. Commun. 7(4), 659-62, (1978).
Database CA "Online" Chemical Abstracts Service, Columbus, OH. Database accession No. 89:41683 XP002208742, Abstract of Sohar et al., Org. Magn. Reson. 11(1), 9-11, (1978).
Database CA "Online" Chemical Abstracts Service, Columbus, OH. Database accession No. 88:152523 XP002208743, Abstract of Kalman et al., Tetrahedron Lett. (48), 4237-40, (1977).
Database CA "Online" Chemical Abstracts Service, Columbus, OH. Database accession No. 81:105381 XP002208744, Abstract of Markov et al., ZH. Org. Khim. 10(6), 1262-4, (1974).
Database CA "Online" Chemical Abstracts Service, Columbus, OH. Database accession No. 76:126938 XP002208745, Abstract of Toth et al., Magy. Kem. Lapja 26(11), 561-70, (1971).

(Continued)

*Primary Examiner*—Deborah C. Lambkin
(74) *Attorney, Agent, or Firm*—Wenderoth, Lind & Ponack, L.L.P.

(57) ABSTRACT

The present invention relates to 2-imino-1,3-thiazine derivatives, in specific, 2-imino-1,3-thiazine derivatives having a selective antagonistic activity or agonistic activity to a cannabinoid type 2 receptor and their pharmaceutical use.

10 Claims, No Drawings

OTHER PUBLICATIONS

Database CA "Online" Chemical Abstracts Service, Columbus, OH. Database accession No. 74:63815 XP002208746, Abstract of Sohar, Magy. Kem. Foly. 76(11), 577-83, (1970).

Database CA "Online" Chemical Abstracts Service, Columbus, OH. Database accession No. 73:44468 XP002208747, Abstract of Toldy et al., (25), 2177-81, (1970).

Avalos et al., Martin, "Reactions of 2-Amino-2-thiazolines with Isocyanates and Isothiocyanates. Chemical and Computational Studies on the Regioselectivity, Adduct Rearrangement and Mechanistic Pathways," *Journal of Organic Chemistry*, vol. 65, pp. 8882-8892, Dec. 5, 2000.

* cited by examiner

2-IMINO-1,3-THIAZINE DERIVATIVES

This application is a divisional of Ser. No. 10/069,421, filed Feb. 26, 2002, now U.S. Pat. No. 6,818,640, which is a 371 U.S. national stage of International Application No. PCT/JP00/06185 filed Sep. 11, 2000.

TECHNICAL FIELD

The present invention relates to 2-imino-1,3-thiazine derivatives, in detail, 2-imino-1,3-thiazine derivatives having a selective antagonistic activity or agonistic activity to a cannabinoid type 2 receptor and pharmaceutical use of themselves.

BACKGROUND ART

Cannabinoid was discovered as the main active substance contained in marijuana in 1960 and found to exhibit an activity to the central nervous system (illusion, euphoria, sensory confusion of time and space) and an activity to the peripheral cell system (immunosuppressive activity, anti-inflammatory activity, analgesic activity).

After that, anandamide and 2-arachidonoylglycerol produced from phospholipid containing arachidonic acid were discovered as endogenous agonists to a cannabinoid receptor. These endogenous agonists were known to exhibit an activity to the central nervous system and an activity to the peripheral cell system. It was disclosed in Hypertension (1997) 29, 1204–1210 that anandamide exhibits an activity to the cardiovascular system.

A cannabinoid type 1 receptor discovered in 1990 was found to distribute in the central nervous system such as the brain. Agonists to this receptor were found to suppress the release of neurotransmitters to cause central actions such as illusion or the like. A cannabinoid type 2 receptor discovered in 1993 was found to distribute in immune tissues such as the spleen or the like. Agonists to this receptor were found to suppress an activation of cells in immunocyte or phlogocyte to exhibit an immunosuppressive activity, an anti-inflammatory activity and an analgesic activity (Nature, 1993, 365, 61–65).

Therefore, selective antagonists or agonists to the cannabinoid type 2 receptor are expected as immunosuppressive agents, anti-inflammatory agents, analgesic agents without causing side effects on the central nervous system such as illusion or the drug dependence, which are associated with the cannabinoid type 1 receptor (Nature, 1998, 349, 277–281).

Known as compounds having an antagonistic activity or agonistic activity to the cannabinoid type 2 receptor are isoindolynone derivatives (WO97/29079 and WO99/02499), pyrazole derivatives (WO98/41519) and the like.

On the other hand, Japanese Patent Publications (Kokai 1986-65894, Kokai 1987-29594) disclose that organophosphorus compounds having a 2-imino-1,3-thiazine skelton are useful as insecticides.

However, it is not known that 2-imino-1,3-thiazine derivatives have an antagonistic activity or agonistic activity to the cannabinoid type 2 receptor.

DISCLOSURE OF INVENTION

The present invention provides 2-imino-1,3-thiazine derivatives or the like as novel compounds having a selective antagonistic activity or agonistic activity to the cannabinoid type 2 receptor.

The present invention comprises, 1) a pharmaceutical composition which comprises a compound of the formula (I):

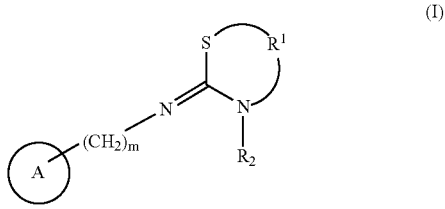

wherein $R^1$ is optionally substituted alkylene, $R^2$ is alkyl; a group of the formula: $-C(=R^5)-R^6$ wherein $R^5$ is O or S, and $R^6$ is alkyl, alkoxy, alkylthio, optionally substituted amino, optionally substituted aralkyloxy, optionally substituted aralkylthio, optionally substituted aralkylamino, alkoxyalkyl, alkylthioalkyl or optionally substituted aminoalkyl; or a group of the formula: $-SO_2R^7$ wherein $R^7$ is alkyl, optionally substituted amino, optionally substituted aryl or optionally substituted heteroaryl, m is an integer of 0 to 2, A is optionally substituted aromatic carbocycle or optionally substituted aromatic heterocycle, a prodrug of itself, a pharmaceutically acceptable salt thereof or a solvate thereof, 2) the pharmaceutical composition according to the above 1) wherein the group of the formula:

is a group of the formula:

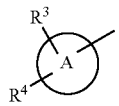

wherein $R^3$ and $R^4$ each is independently hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl or a group of the formula: $-C(=O)-R^H$ wherein $R^H$ is hydrogen, alkyl, optionally substituted aryl or optionally substituted non-aromatic heterocyclic group, or $R^3$ and $R^4$ taken together may form alkylenedioxy, A is optionally substituted aromatic carbocycle or optionally substituted aromatic heterocycle, 3) the pharmaceutical composition according to the above 1) or 2) which has a binding activity to a cannabinoid type 2 receptor, 4) the pharmaceutical composition according to the above 3) which has an agonistic activity to a cannabinoid type 2 receptor, 5) the pharmaceutical composition according to the above 3) which is useful as an anti-inflammatory agent, 6) the pharmaceutical composition according to the above 3) which is useful as an immunosuppressive agent, 7) the pharmaceutical composition according to the above 3) which is useful as a nephritis treating agent, 8) a compound of the formula (II):

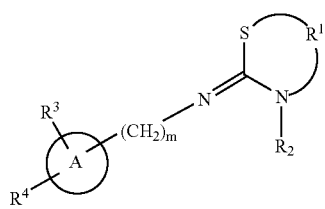

(II)

wherein $R^1$ is optionally substituted alkylene, $R^2$ is a group of the formula: —C(=$R^5$)—$R^6$ wherein $R^5$ is O or S, $R^6$ is alkyl, alkoxy, alkylthio, optionally substituted amino, optionally substituted aralkyloxy, optionally substituted aralkylthio, optionally substituted aralkylamino, alkoxyalkyl, alkylthioalkyl or optionally substituted aminoalkyl, or a group of the formula: —$SO_2R^7$ wherein $R^7$ is alkyl, optionally substituted amino, optionally substituted aryl or optionally substituted heteroaryl, $R^3$ and $R^4$ each is independently hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl, or a group of the formula: —C(=O)—$R^H$ wherein $R^H$ is hydrogen, alkyl, optionally substituted aryl or optionally substituted non-aromatic heterocyclic group, or $R^3$ and $R^4$ taken together may form alkylenedioxy, m is an integer of 0 to 2, A is optionally substituted aromatic carbocycle or optionally substituted aromatic heterocycle, a prodrug of itself, a pharmaceutically acceptable salt thereof or a solvate thereof, 9) the compound according to the above 8) wherein m is 0, a prodrug of itself, a pharmaceutically acceptable salt thereof or a solvate thereof, 10) the compound according to the above 8) or 9) wherein $R^1$ is a C2–C9 straight or branched alkylene optionally substituted with alkylene, a prodrug of itself, a pharmaceutically acceptable salt thereof or a solvate thereof, 11) the compound according to any one of the above 8) to 10) wherein $R^1$ is a C2–C9 straight alkylene substituted with alkylene, or a C2–C9 branched alkylene, a prodrug of itself, a pharmaceutically acceptable salt thereof or a solvate thereof, 12) the compound according to any one of the above 8) to 11) wherein $R^6$ is alkoxy or alkylthio, and $R^7$ is optionally substituted aryl, a prodrug of itself, a pharmaceutically acceptable salt thereof or a solvate thereof, 13) the compound according to any one of the above 8) to 12) wherein $R^3$ and $R^4$ each is independently hydrogen, alkyl, alkoxy or alkylthio, and A is optionally substituted aromatic carbocycle, a prodrug of itself, a pharmaceutically acceptable salt thereof or a solvate thereof, 14) the compound according to the above 8) wherein $R^1$ is 2,2-dimethyltrimethylene, 2,2-diethyltrimethylene, 2,2-ethylenetrimethylene, 1-methyltrimethylene, 2-methyltrimethylene, trimethylene, 2,2-di-n-propyltrimethylene, 2,2-tetramethylenetrimethylene, 2,2-pentamethylenetrimethylene, 1,1-dimethylethylene or 1-methylethylene, $R^6$ is methyl, ethyl, n-propyl, i-propyl, methoxy, ethoxy, n-propoxy, i-propoxy, n-butoxy, methylthio, ethylthio, n-propylthio, i-propylthio, i-butylthio, sec-butylthio, benzyloxy, benzylthio, methoxymethyl, ethoxymethyl, methylthiomethyl, ethylthiomethyl or ethylamino, $R^7$ is methyl, ethyl, 4-tolyl, 4-nitrophenyl, 3-nitrophenyl, 2-nitrophenyl, 4-methoxyphenyl, 4-trifluoromethylphenyl, 2-thienyl or 2-naphthyl, $R^3$ is hydrogen, methyl, ethyl, n-propyl, i-propyl, n-butyl, i-butyl, sec-butyl, t-butyl, methoxy, ethoxy, n-propoxy, i-propoxy, n-butoxy, methylthio, ethylthio, n-propylthio, i-propylthio, dimethylamino, acetylamino, N-acetylmethylamino, diethylamino, ethylmethylamino, propylmethylamino, phenyl, phenoxy, fluoro, chloro, bromo, nitro, trifluoromethyl, difluoromethoxy, trifluoromethoxy, N-methylcarbamoyl, methoxycarbonyl, methanesulfinyl, ethanesulfinyl, methanesulfonyl, ethanesulfonyl, acetyl, methoxymethyl, 1-methoxyethyl, 3-pyridyl, morpholino, pyrrolidino, piperidino, 2-oxopyrrolidino, 1-methoxyiminoethyl or morpholinocarbonyl, $R^4$ is hydrogen, methyl, ethyl, fluoro, chloro, nitro, methoxy or ethoxy, or $R^3$ and $R^4$ taken together may form —O—$CH_2$—O—, A is benzene, naphthalene, pyridine or quinoline, a prodrug of itself, a pharmaceutically acceptable salt thereof or a solvate thereof, 15) a pharmaceutical composition which comprises the compound according to any one of the above 8) to 14), a prodrug of itself, a pharmaceutically acceptable salt thereof or a solvate thereof, 16) the pharmaceutical composition according to the above 15) which has a binding activity to a cannabinoid type 2 receptor, 17) the pharmaceutical composition according to the above 16) which has an agonistic activity to a cannabinoid type 2 receptor, 18) the pharmaceutical composition according to the above 16) which is useful as an anti-inflammatory agent, 19) the pharmaceutical composition according to the above 16) which is useful as an immunosuppressive agent, 20) the pharmaceutical composition according to the above 16) which is useful as a nephritis treating agent, 21) a method for treating inflammation which comprises administering the pharmaceutical composition according to the above 1), 22) a method of immunosuppression which comprises administering the pharmaceutical composition according to the above 1), 23) a method for treating nephritis which comprises administering the pharmaceutical composition according to the above 1), 24) use of the compound according to the above 1) for manufacturing an anti-inflammatory agent, 25) use of the compound according to the above 1) for manufacturing an immunosuppressive agent, and 26) use of the compound according to the above 1) for manufacturing a nephritis treating agent.

BEST MODE FOR CARRYING OUT THE INVENTION

The meanings of each term used in compound of the formula (I) and (II) are explained below. Each term is used to express the same meaning in the specification.

The term "alkylene" includes a C2–C10 straight or branched alkylene, for example, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, 2,2-di-n-propyltrimethylene or the like. Preferred is a C2–C9 straight or branched alkylene. More preferred is a C2–C9 branched alkylene, for example, 2,2-dimethyltrimethylene, 2,2-diethyltrimethylene, 1-methyltrimethylene, 2-methyltrimethylene, trimethylene, 2,2-di-n-propyltrimethylene, 1,1-dimethylethylene or 1-methylethylene. The position number of these substituents is based on either the order of N—$R^1$—S or that of S—$R^1$—N.

Examples of substituents of "optionally substituted alkylene" include alkylene (e.g., methylene, ethylene, trimethylene, tetramethylene, pentamethylene or the like), cycloalkyl (e.g., cyclopropyl, cyclobutyl, cyclopentyl, cyclohexyl or the like), alkoxy (e.g., methoxy, ethoxy or the like), alkylthio (e.g., methylthio, ethylthio or the like), alkylamino (e.g., methylamino, ethylamino, dimethylamino or the like), acylamino (e.g., acetylamino or the like), aryl (e.g., phenyl or the like), aryloxy(e.g., phenoxy or the like), halogen (fluoro, chloro, bromo, iodo), hydroxy, amino, nitro, alkylsulfonyl (e.g., methanesulfonyl, ethanesulfonyl or the like), arylsulfonyl (e.g., benzenesulfonyl or the like), cyano, hydroxyamino, carboxy, alkoxycarbonyl (e.g., methoxycarbonyl, ethoxycarbonyl or the like), acyl (e.g., acetyl, benzoyl or the like), aralkyl (e.g., benzyl or the like), mercapto, hydorazino, amidino, guanidino or the like. One to four of these substituents may substitute at any position. Preferred as the substituent of "optionally substituted alkylene" is alkylene.

Alkylene substituted with alkylene include alkylene substituted via a spiro atom with alkylene (e.g., 2,2-ethylenetrimethylene, 2,2-trimethylenetrimethylene, 2,2-tetramethylenetrimethylene, 2,2-pentamethylenetrimethylene or the like) and alkylene substituted at the different positions with alkylene (e.g., 1,2-tetramethyleneethylene, 1,2-ethylenetrimethylene or the like). Preferred examples include 2,2-ethylenetrimethylene, 2,2-trimethylenetrimethylene, 2,2-tetramethylenetrimethylene, 2,2-pentamethylenetrimethylene, especially, 2,2-ethylenetrimethylene, 2,2-tetramethylenetrimethylene and 2,2-pentamethylenetrimethylene.

The term "alkyl" includes a C1–C10 straight or branched alkyl, for example, methyl, ethyl, n-propyl, i-propyl, n-butyl, i-butyl, sec-butyl, tert-butyl, n-pentyl, i-pentyl, neopentyl, n-hexyl, n-heptyl, n-octyl, n-noyl, n-decyl or the like. Preferred is a C1–C4 straight or branched alkyl, for example, methyl, ethyl, n-propyl, i-propyl, n-butyl, i-butyl, sec-butyl and tert-butyl.

The term "alkoxy" includes an oxygen atom substituted with the above "alkyl", for example, methoxy, ethoxy, n-propoxy, i-propoxy, n-butoxy, i-butoxy, sec-butoxy, tert-butoxy, n-pentyloxy, n-hexyloxy, n-heptyloxy, n-octyloxy or the like. Preferred is a C1–C4 straight or branched alkoxy, for example, methoxy, ethoxy, n-propoxy, i-propoxy, n-butoxy, i-butoxy, sec-butoxy and tert-butoxy.

The term "alkylthio" includes a sulfur atom substituted with the above "alkyl", for example, methylthio, ethylthio, n-propylthio, i-propylthio, n-butylthio, i-butylthio, sec-butylthio, tert-butylthio, n-pentylthio, n-hexylthio or the like. Preferred is a C1–C4 straight or branched alkylthio, for example, methylthio, ethylthio, n-propylthio, i-propylthio, n-butylthio, i-butylthio, sec-butylthio and tert-butylthio.

Examples of substituents of "optionally substituted amino" includes alkyl (e.g., methyl, ethyl, n-propyl, i-propyl or the like), acyl (e.g., formyl, acetyl, propionyl, benzoyl or the like) or the like. A nitrogen atom of an amino group may be mono- or di-substituted with these substituents.

Examples of "optionally substituted amino" include amino, methylamino, ethylamino, n-propylamino, i-propylamino, dimethylamino, diethylamino, ethylmethylamino, acetylamino, N-acetylmethylamino, propylmethylamino or the like.

The term "aryl" includes a C6–C14 aromatic carbocyclic group, for example, phenyl, naphthyl, anthryl, phenanthryl or the like.

The term "aralkyl" includes the above "alkyl" substituted with the above "aryl", for example, benzyl, phenylethyl (e.g., 1-phenylethyl, 2-phenylethyl), phenylpropyl (e.g., 1-phenylpropyl, 2-phenylpropyl, 3-phenylpropyl or the like), naphthylmethyl (e.g., 1-naphthylmethyl, 2-naphthylmethyl or the like) or the like.

The term "aralkyloxy" includes an oxygen atom substituted with the above "aralkyl", for example, benzyloxy, phenylethyloxy (e.g., 1-phenylethyloxy, 2-phenylethyloxy), phenylpropoxy (e.g., 1-phenylpropyloxy, 2-phenylpropyloxy, 3-phenylpropyloxy or the like), naphthylmethoxy (e.g., 1-naphthylmethoxy, 2-naphthylmethoxy or the like) or the like.

The term "aralkylthio" includes a sulfur atom substituted with the above "aralkyl", for example, benzylthio, phenylethylthio (e.g., 1-phenylethylthio, 2-phenylethylthio), phenylpropylthio (e.g., 1-phenylpropylthio, 2-phenylpropylthio, 3-phenylpropylthio or the like), naphthylmethylthio (e.g., 1-naphthylmethylthio, 2-naphthylmethylthio or the like) or the like.

The term "aralkylamino" includes a nitrogen atom substituted with one or two of the above "aralkyl", for example, benzylamino, phenylethylamino (e.g., 1-phenylethylamino, 2-phenylethylamino), phenylpropylamino (e.g., 1-phenylpropylamino, 2-phenylpropylamino, 3-phenylpropylamino), naphthylmethylamino (e.g., 1-naphthylmethylamino, 2-naphthylmethylamino or the like), dibenzylamino or the like.

The term "alkoxyalkyl" includes the above "alkyl" substituted with the above "alkoxy", for example, methoxymethyl, ethoxymethyl, n-propoxymethyl, 1-methoxyethyl, 2-methoxyethyl, 1-ethoxyethyl, 2-ethoxyethyl, 1-n-propoxyethyl, 2-n-propoxyethyl, 1-methoxy-n-propyl, 2-methoxy-n-propyl, 3-methoxy-n-propyl, 1-ethoxy-n-propyl, 2-ethoxy-n-propyl, 3-ethoxy-n-propyl, 1-n-propoxy-n-propyl, 2-n-propoxy-n-propyl, 3-n-propoxy-n-propyl or the like.

The term "alkylthioalkyl" includes the above "alkyl" substituted with the above "alkylthio", for example, methylthiomethyl, ethylthiomethyl, n-propylthiomethyl, 1-methylthioethyl, 2-methylthioethyl, 1-ethylthioethyl, 2-ethylthioethyl, 1-n-propylthioethyl, 2-n-propylthioethyl, 3-n-propylthioethyl, 1-methylthio-n-propyl, 2-methylthio-n-propyl, 3-methylthio-n-propyl, 1-ethylthio-n-propyl, 2-ethylthio-n-propyl, 3-ethylthio-n-propyl, 1-n-propylthio-n-propyl, 2-n-propylthio-n-propyl, 3-n-propylthio-n-propyl or the like.

The term "optionally substituted aminoalkyl" includes the above "alkyl" substituted with the above "optionally substituted amino", for example, N-methylaminomethyl, N-acetylaminomethyl, N,N-dimethylaminomethyl or the like.

The term "alkoxyalkoxy" includes the above "alkoxy" substituted with the above "alkoxy", for example, methoxymethoxy, ethoxymethoxy, n-propoxymethoxy, isopropoxymethoxy, 1-methoxyethoxy, 2-methoxyethoxy or the like.

The term "alkylthioalkoxy" includes the above "alkoxy" substituted with the above "alkylthio", for example, methylthiomethoxy, ethylthiomethoxy, n-propylthiomethoxy, isopropylthiomethoxy, 1-methylthioethoxy, 2-methoxyethoxy or the like.

The term "heteroaryl" includes a C1–C9 heteroaryl having one to four nitrogen atom(s), oxygen atom(s) and/or sulfur atom(s), for example, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiadinyl (e.g., 1-phenothiadinyl, 2-phenothiadinyl, 3-phenothiadinyl, 4-phenothiadinyl) or the like.

Preferred as heteroaryl of $R^3$ and $R^4$ is 3-pyridyl. Preferred as heteroaryl of $R^7$ is 2-thienyl.

The ring A includes "optionally substituted aromatic carbocycle" or "optionally substituted aromatic heterocycle".

The term "aromatic carbocycle" includes a C6–C14 aromatic carbocycle, for example, benzene, naphthalene, anthracene, phenanthrene or the like. Preferred is benzene or naphthalene.

The term "aromatic heterocycle" includes a C1–C9 aromatic ring having one to four nitrogen atom(s), oxygen atom(s) and/or sulfur atom(s), for example, furan, thiophene, pyrrole, imidazole, pyrazole, triazole, tetrazole, oxazole, isoxazole, thiazole, thiadiazole, isothiazole, pyridine, pyridazine, pyrimidine, furazan, pyrazine, benzofuran, benzothiophene, benzimidazole, dibenzofuran, benzoxazole, quinoxaline, cinnoline, quinazoline, quinoline, phthalazine, isoquinoline, purine, pteridine, carbazole, phenanthridine, acridine, indole, isoindole or phenazine or the like. Preferred is pyridine, quinoline or isoquinoline.

Examples of the substituents of "optionally substituted aralkyloxy", "optionally substituted aralkylthio", "optionally substituted aralkylamino", "optionally substituted aryl", "optionally substituted heteroaryl", "optionally substituted aryloxy", "optionally substituted aromatic carbocycle", "optionally substituted aromatic heterocycle" and "optionally substituted non-aromatic heterocyclic group" include alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl, a group of the formula: —C(=O)—$R^H$ wherein $R^H$ is hydrogen, alkyl, optionally substituted aryl or optionally substituted non-aromatic heterocyclic group, arylsulfonyl (e.g., benzenesulfonyl or the like), cyano, hydroxy amino, aralkyl (e.g., benzyl or the like), mercapto, hydrazino, amidino, guanidino, isocyano, isocyanato, thiocyanato, isothiocyanato, sulfamoyl, formyloxy, haloformyl, oxalo, thioformyl, thiocarboxy, dithiocarboxy, thiocarbamoyl, sulfino, sulfo, sulfoamino, azido, ureido, amidino, guanidino, oxo, thioxo or the like.

These substituents may substitute at any substitutable positions. Alkylenedioxy may substitute at the same or different positions on the ring. An example of alkylenedioxy includes —O—$CH_2$—O—, —O—$CH_2$—$CH_2$—O—, —O—$CH_2$—$CH_2$—$CH_2$—O—.

The term "aryloxy" includes an oxygen atom substituted with the above "aryl", for example, phenoxy, naphthoxy (e.g., 1-naphthoxy, 2-naphthoxy or the like), anthryloxy (e.g., 1-anthryloxy, 2-anthryloxy or the like), phenanthryl (e.g., 1-phenanthryl, 2-phenanthryl or the like) or the like.

The term "cycloalkyl" includes C3–C7 cycloalkyl, for example, cyclopropyl, cyclobutyl, cyclopentyl, cyclohexyl or the like.

The term "halogen" includes fluoro, chloro, bromo and iodo. Preferred is fluoro, chloro or bromo.

The term "haloalkyl" includes the above "alkyl" substituted with one or more halogen, for example, chloromethyl, dichloromethyl, difluoromethyl, trifluoromethyl, chloroethyl (e.g., 1-chloroethyl, 2-chloroethyl or the like), dichloroethyl (e.g., 1,1-dichloroethyl, 1,2-dichloroethyl, 2,2-dichloroethyl or the like) or the like.

The term "haloalkoxy" includes the above "alkoxy" substituted with one or more halogen, for example, dichloromethoxy, difluoromethoxy, trifluoromethoxy, trifluoroethoxy (2,2,2-trifluoroethoxy or the like) or the like.

Examples of the substituents of "optionally substituted carbamoyl" include alkyl (e.g., methyl, ethyl, n-propyl, i-propyl or the like), acyl (e.g., formyl, acetyl, propionyl, benzoyl or the like) or the like. The nitrogen atom of carbamoyl group may be mono- or di-substituted with these substituents.

Preferred as "optionally substituted carbamoyl" is carbamoyl, N-methylcarbamoyl or N-ethylcarbamoyl.

The term "alkoxycarbonyl" includes carbonyl substituted with "alkoxy". Preferred is methoxycarbonyl, ethoxycarbonyl or the like.

The term "alkylsulfinyl" includes sulfinyl substituted with the above "alkyl". Preferred is methanesulfinyl, ethanesulfinyl or the like.

The term "alkylsulfonyl" includes sulfonyl substituted with the above "alkyl". Preferred is methanesulfonyl, ethanesulfonyl or the like.

The term "non-aromatic heterocyclic group" includes a C1–C9 non-aromatic ring having one to four nitrogen atom(s), oxygen atom(s) and/or sulfur atom(s), for example, 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl or the like. Preferred is morpholino, pyrrolidino, piperidino or piperazino.

The term "alkoxyiminoalkyl" include the above "alkyl" substituted with alkoxyimino, for example, methoxyiminomethyl, ethoxyiminomethyl, 1-methoxyiminoethyl or the like.

Examples of a group of the formula: —C(=O)—$R^H$ wherein $R^H$ is hydrogen, alkyl, optionally substituted aryl or optionally substituted non-aromatic heterocyclic group include formyl, acetyl, benzoyl, toluoyl, morpholinocarbonyl or the like.

The term "m" is an integer of 0 to 2. Preferred as "m" is 0.

The term "an agonistic activity to a cannabinoid type 2 receptor" includes agonizing a cannabinoid type 2 receptor.

The compounds of the present invention can be prepared in accordance with the following processes.

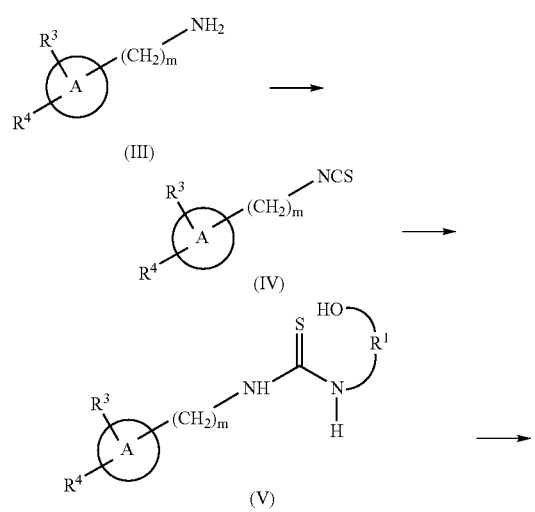

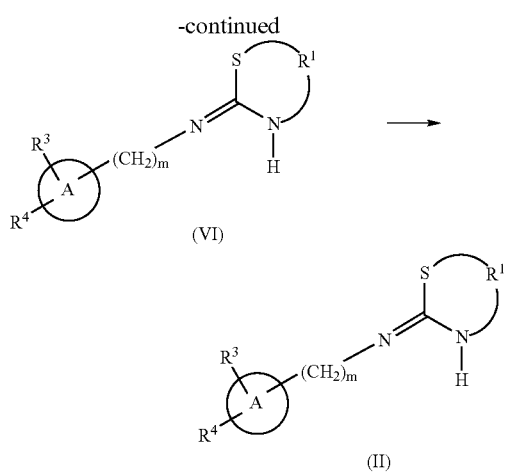

wherein $R^1$ is optionally substituted alkylene, $R^2$ is alkyl; a group of the formula: —C(=$R^5$)—$R^6$ wherein $R^5$ is O or S, $R^6$ is alkyl, alkoxy, alkylthio, optionally substituted amino, optionally substituted aralkyloxy, optionally substituted aralkylthio, optionally substituted aralkylamino, alkoxyalkyl, alkylthioalkyl or optionally substituted aminoalkyl; or a group of the formula: —$SO_2R^7$ wherein $R^7$ is alkyl, optionally substituted amino, optionally substituted aryl or optionally substituted heteroaryl, $R^3$ and $R^4$ each is independently hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl, or a group of the formula: —C(=O)—$R^H$ wherein $R^H$ is hydrogen, alkyl, optionally substituted aryl or optionally substituted non-aromatic heterocyclic group, or $R^3$ and $R^4$ taken together may form —O—$CH_2$—O—, m is an integer of 0 to 2, A is optionally substituted aromatic carbocycle or optionally substituted aromatic heterocycle.

Process 1

This is a process for producing a compound of the formula (IV) which comprises converting amino group of a compound of the formula (III) to isothiocyanic acid ester (isothiocyanate).

A method for converting amino group to isothio cyanic acid ester (isothiocyanate) includes the following methods; 1) a method which comprises reacting the starting compound with carbon disulfide in the presence of a base such as ammonia ($NH_3$, $NH_4OH$), triethylamine ($Et_3N$) and reacting the obtained dithiocarbamate with ethyl chlorocarboxylate ($ClCO_2Et$) and triethylamine ($Et_3N$), 2) a method which comprises reacting the above dithiocarbamate with acid metalate such as lead nitrate or the like, 3) a method of reacting thiophosgene ($CSCl_2$) and 4) a method of reacting thiocarbonyldiimidazole or the like.

In the above 1), a base (1.0 to 1.5 mole equivalent) and carbon disulfide (1.0 to 1.5 mole equivalent) are added to a solution of a compound of the formula (III) in an aprotic solvent (e.g., diethylether, tetrahydrofuran, dimethylformamide, benzene, toluene, dichloromethane, chloroform or the like) and the mixture is stirred for 0.5 to 10 hours. After that, ethyl chlorocarboxylate (1.0 to 1.5 mole equivalent) and triethylamine (1.0 to 1.5 mole equivalent) are added thereto and the mixture is stirred in the same solvent for 0.5 to 10 hours. The reaction temperature is preferably 0 to 100° C., especially 0° C. to room temperature.

In the above 3), thiophosgene (1.0 to 1.5 mole equivalent) is added to a solution of the compound of the formula (III) in an aprotic solvent (e.g., diethylether, tetrahydrofuran, dimethylformamide, benzene, toluene, dichloromethane, chloroform or the like) and stirred for 0.5 to 10 hours. The reaction temperature is preferably 0 to 100° C., especially 0° C. to room temperature.

In the above 4), thiocarbonyldiimidazole (1.0 to 1.5 mole equivalent) is added to a solution of the compound of the formula (III) in an aprotic solvent (e.g., diethylether, tetrahydrofuran, dimethylformamide, benzene, toluene, dichloromethane, chloroform or the like) and stirred for 0.5 to 10 hours. The reaction temperature is preferably 0 to 100° C., especially 0° C. to room temperature.

Examples of the compound of the formula (III) wherein m is 0 include aniline, 2-methylaniline, 2-ethylaniline, 2-n-propylaniline, 2-i-propylaniline, 2-n-butylaniline, 2-sec-butylaniline, 2-t-butylaniline, 3-methylaniline, 3-i-propylaniline, 3-i-propyl-4-methylaniline, 3-t-butylaniline, 4-methylaniline, 4-i-propylaniline, 2,6-dimethylaniline, 2,3-dimethylaniline, 2,4-dimethylaniline, 3,4-diethylaniline, 2,5-dimethylaniline, 3,4-dimethylaniline, 3,5-dimethylaniline, 2,6-diethylaniline, 2,6-di-i-propylaniline, 2-methoxyaniline, 2-ethoxyaniline, 2-i-propoxyaniline, 3-methoxyaniline, 3,5-dimethoxyaniline, 3-n-butoxyaniline, 4-n-butoxyaniline, 4-ethoxyaniline, 3,4-dimethoxyaniline, 2-methylthioaniline, 2-ethylthioaniline, 2-i-propylthioaniline, 2-N,N-dimethylaminoaniline, 2-phenylaniline, 3-phenylaniline, 4-phenoxyaniline, 2-cyclohexylaniline, 2-cyclopentylaniline, 2-nitroaniline, 2,4-dinitroaniline, 2-fluoroaniline, 2-chloroaniline, 4-chloroaniline, 2,3-dichloroaniline, 3,4-dichloroaniline, 2-i-propyl-4-nitroaniline, 2-i-propyl-6-nitroaniline, 2-hydroxyaniline, 2-N,N-dimethylaminocarbonylaniline, 2-N-acetylaniline, 2-(1-ethylpropyl)aniline, 2-i-propyl4-methylaniline, 2-i-propyl-4-hydroxyaniline, 2-i-propyl-4-chloroaniline, 2-i-propyl-4-aminoaniline, 2-i-propyl-5-methylaniline, 2-i-propyl-5-hydroxy aniline, 2-i-propyl-5-chloroaniline, 4-chloro-3-methylaniline, 3,4-methylenedioxyaniline or the like.

Examples of the compound of the formula (III) wherein m is 1 include benzylamine, 2-methylbenzylamine, 2-ethylbenzylamine, 2-n-propylbenzylamine, 2-i-propylbenzylamine, 2-n-butylbenzylamine, 2-sec-butylbenzylamine, 2-t-butylbenzylamine, 3-methylbenzylamine, 3-i-propylbenzylamine, 3-i-propyl-4-methylbenzylamine, 3-t-butylbenzylamine, 4-methylbenzylamine, 4-i-propylbenzylamine, 2,6-dimethylbenzylamine, 2,3-dimethylbenzylamine, 2,4-dimethylbenzylamine, 3,4-diethylbenzylamine, 2,5-dimethylbenzylamine, 3,4-dimethylbenzylamine, 3,5-dimethylbenzylamine, 2,6-diethylbenzylamine, 2,6-di-i-propylbenzylamine, 2-methoxybenzylamine, 2-ethoxybenzylamine, 2-i-propoxybenzylamine, 3-methoxybenzylamine, 3,5-dimethoxybenzylamine, 3-n-butoxybenzylamine, 4-n-butoxybenzylamine, 4-ethoxybenzylamine, 3,4-dimethoxybenzylamine, 2-methylthiobenzylamine, 2-ethylthiobenzylamine, 2-i-propylthiobenzylamine, 2-N,N-dimethylaminobenzylamine, 2-phenylbenzylamine, 3-phenylbenzylamine, 4-phenoxybenzylamine, 2-cyclohexylbenzylamine, 2-cyclopentylbenzylamine, 2-nitrobenzylamine, 2,4-dinitrobenzylamine, 2-fluorobenzylamine, 2-chlorobenzylamine, 4-chlorobenzylamine, 2,3-dichlorobenzylamine, 3,4-dichlorobenzylamine, 2-i-propyl-4-nitrobenzylamine, 2-i-propyl-6-nitrobenzylamine, 2-hydroxybenzylamine, 2-N,N-dimethylaminocarbonylbenzylamine, 2-N-acetylbenzylamine, 2-(1-ethylpropyl)benzylamine, 2-i-propyl4-methylbenzylamine, 2-i-propyl-4-hydroxybenzylamine, 2-i-propyl-4-chlorobenzylamine, 2-i-propyl-4-aminobenzylamine, 2-i-propyl-5-methylbenzylamine, 2-i-propyl-5-hydroxybenzylamine, 2-i-propyl-5-chlorobenzylamine, 4-chloro-3-methylbenzylamine, 3,4-methylenedioxybenzylamine or the like.

Examples of the compound of the formula (III) wherein m is 2 include phenethylamine, 2-methylphenethylamine, 2-ethylphenethylamine, 2-n-propylphenethylamine, 2-i-propylphenethylamine, 2-n-butylphenethylamine, 2-sec-butylphenethylamine, 2-t-butylphenethylamine, 3-methylphenethylamine, 3-i-propylphenethylamine, 3-i-propyl-4-methylphenethylamine, 3-t-butylphenethylamine, 4-methylphenethylamine, 4-i-propylphenethylamine, 2,6-dimethylphenethylamine, 2,3-dimethylphenethylamine, 2,4-dimethylphenethylamine, 3,4-diethylphenethylamine, 2,5-dimethylphenethylamine, 3,4-dimethylphenethylamine, 3,5-dimethylphenethylamine, 2,6-diethylphenethylamine, 2,6-di-i-propylphenethylamine, 2-methoxyphenethylamine, 2-ethoxyphenethylamine, 2-i-propoxyphenethylamine, 3-methoxyphenethylamine, 3,5-dimethoxyphenethylamine, 3-n-butoxyphenethylamine, 4-n-butoxyphenethylamine, 4-ethoxyphenethylamine, 3,4-dimethoxyphenethylamine, 2-methylthiophenethylamine, 2-ethylthiophenethylamine, 2-i-propylthiophenethylamine, 2-N,N-dimethylaminophenethylamine, 2-phenylphenethylamine, 3-phenylphenethylamine, 4-phenoxyphenethylamine, 2-cyclohexylphenethylamine, 2-cyclopentylphenethylamine, 2-nitrophenethylamine, 2,4-dinitrophenethylamine, 2-fluorophenethylamine, 2-chlorophenethylamine, 4-chlorophenethylamine, 2,3-dichlorophenethylamine, 3,4-dichlorophenethylamine, 2-i-propyl-4-nitrophenethylamine, 2-i-propyl-6-nitrophenethylamine, 2-hydroxyphenethylamine, 2-N,N-dimethylaminocarbonylphenethylamine, 2-N-acetylphenethylamine, 2-(1-ethylpropyl)phenethylamine, 2-i-propyl4-methylphenethylamine, 2-i-propyl-4-hydroxyphenethylamine, 2-i-propyl-4-chlorophenethylamine, 2-i-propyl-4-aminophenethylamine, 2-i-propyl-5-methylphenethylamine, 2-i-propyl-5-hydroxyphenethylamine, 2-i-propyl-5-chlorophenethylamine, 4-chloro-3-methylphenethylamine, 3,4-methylenedioxyphenethylamine or the like.

Process 2

This is a process for producing a compound of the formula (V) which comprises reacting an isothiocyanate of the compound of the formula (IV) with $NH_2$—$R^1$—OH.

This process can be carried out in an aprotic solvent (e.g., diethylether, tetrahydrofuran, dimethylformamide, benzene, toluene, dichloromethane, chloroform or the like).

The reaction temperature is preferably 0 to 100° C., especially 0° C. to room temperature. The reaction time is 0.5 to 10 hours.

The amount of $NH_2$—$R^1$—OH wherein $R^1$ is optionally substituted alkylene is 1.0 to 1.5 mole equivalent to that of the compound of the formula (IV).

Examples of $NH_2$—$R^1$—OH include 2-aminoethanol, 2-amino-2-methylethanol, 2-amino-1-methylethanol, 2-amino-1,1-dimethylethanol, 3-aminopropanol, 3-amino-2,2-dimethylpropanol, 3-amino-1-methylpropanol, 3-amino-2-methylpropanol, 3-amino-3-methylpropanol, 3-amino-2,2-diethylpropanol, 1-aminomethyl-1- hydroxymethylcyclopropane, 1-aminomethyl-1-(hydroxymethyl)cyclobutane, 2-(aminomethyl)cyclopentanol or the like.

Process 3

This is a process for producing a compound of the formula (VI) which comprises the cyclization of the compound of the formula (V).

A method of the cyclization includes 1) a method which comprises reacting with diethylazodicarboxylate (DEAD) and triphenylphosphine ($Ph_3P$), 2) a method which comprises reacting with hydrochloric acid or the like.

In the above 1), the reaction can be carried out in an aprotic solvent (e.g., diethylether, tetrahydrofuran, dimethylformamide, benzene, toluene, dichloromethane, chloroform or the like) with stirring for 0.5 to 5 hours at 0° C. to room temperature. The amount of diethylazodicarboxylate (DEAD) and triphenylphosphine ($Ph_3P$) are 1.0 to 1.5 mole equivalent to that of the compound (V).

In the above 2), the reaction can be carried out in concentrated hydrochloric acid with refluxing for 0.5 to 10 hours.

Process 4

This is a process for producing a compound of the formula (II) which comprises introducing $R^2$ (a group of the formula: $—C(=R^5)—R^6$ or a group of the formula: $—SO_2R^7$ wherein $R^5$ is O or S, $R^6$ is alkyl, alkoxy, alkylthio, optionally substituted amino, optionally substituted aralkyloxy, optionally substituted aralkylthio, optionally substituted aralkylamino, alkoxyalkyl, alkylthioalkyl or optionally substituted aminoalkyl, $R^7$ is alkyl, optionally substituted amino, optionally substituted aryl or optionally substituted heteroaryl, to the compound of the formula (VI).

This process can be carried out by reacting with a compound of the formula: $X—C(=R^5)—R^6$ wherein $R^5$ and $R^6$ are as defined above and X is halogen in the presence of a base (e.g., triethylamine, pyridine, N,N-dimethylaminopyridine or the like). This process can be carried out under generally known conditions of N-acylation. For example, the reaction can be carried out in an aprotic solvent (e.g., diethylether, tetrahydrofuran, dimethylformamide, benzene, toluene, dichloromethane, chloroform or the like) with stirring at 0 to 100° C. for 0.5 to 10 hours.

A thioic acid ester, a compound wherein $R^5$ is S, $R^6$ is alkylthio or optionally substituted aralkylthio can be prepared by reacting with carbon dioxide ($CS_2$) in the presence of a base (e.g., sodium hydride or the like), and reacting with halogenated alkyl (e.g., methyl iodide, ethyl iodide or the like) or halogenated aralkyl (e.g., benzylbromide or the like). The reaction can be carried out in an aprotic solvent (e.g., diethylether, tetrahydrofuran, dimethylformamide, benzene, toluene, dichloromethane, chloroform or the like) with stirring at 0° C. to room temperature.

When $R^2$ to be introduced is a group of the formula: $—SO_2R^7$ wherein $R^7$ is alkyl, optionally substituted amino, optionally substituted aryl or optionally substituted heteroaryl, the compound of the formula (VI) can be reacted with a compound of the formula: $R^7SO_2X$ wherein X is halogen or the like in the presence of a base.

A prodrug is a derivative which is converted to a pharmaceutically active compound of the present invention under a physiological condition. Method for the selection and process of an appropriate prodrug derivative are described in the literature such as Design of Prodrugs, Elsevier, Amsterdam 1985.

A prodrug of the present invention can be prepared by introducing a leaving group to substituents on ring A which are substitutable (e.g., amino, hydroxy or the like). Examples of a prodrug derived form a compound having an amino group includes carbamate derivatives (e.g., methylcarbamate, cyclopropylmethylcarbamate, t-butylcarbamate, benzylcarbamate or the like), amide derivatives (e.g., formamide, acetamide or the like), N-alkyl derivative (e.g., N-allylamine, N-methoxymethylamine or the like) or the like. Examples of a prodrug derived form a compound having hydroxy group include ether derivatives (methoxymethylether, methoxyethoxymethylether or the like), ester derivatives (e.g., acetate, pivaloate, benzoate or the like) or the like.

Examples of a pharmaceutically acceptable salt include basic salts (e.g., alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts). Acid addition salts include, for example, mineral acid salts such as hydrochlorides salts, sulfates salts, nitrate salts, phosphates salts, carbonates salts, hydrogen carbonates salts or perchlorates salts; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

A solvate includes a solvate of the compound of the formula (I) or (II), a prodrug of itself or a pharmaceutically acceptable salt thereof, for example, monosolvate, disolvate, monohydrate, dihydrate or the like.

The compound of the present invention has a binding activity to the cannabinoid type 2 receptor (CB2R), and selectively binds to the cannabinoid type 2 receptor (CB2R) to exhibit an antagonistic activity or agonistic activity to CB2R, especially an agonistic activity to CB2R.

Since the compound of the present invention does not have a binding activity to the cannabinoid type 1 receptor (CB1R), the present compound neither causes side effects on the central nervous system such as illusion or the drug dependence associated with the cannabinoid type 1 receptor.

Therefore, the compound of the present invention can be used for treating or preventing diseases associated with the cannabinoid type 2 receptor (CB2R). For example, Proc. Natl. Acad. Sci. USA 96, 14228–14233. discloses that CB2R agonists have an anti-inflammatory activity and analgesic activity. Nature, 1998, 349, 277–281 discloses that CB2R agonists have an analgesic activity. European Journal of Pharmacology 396 (2000) 85–92 discloses that CB2R antagonists have an analgesic activity.

The compound of the present invention suppresses an activation of cells in immunocyte or phlogocyte to exhibit an activity to the peripheral cell system (e.g., an immunosuppressive activity, an anti-inflammatory activity and an analgesic activity). Thus, the present compounds can be used as anti-inflammatory agents, antiallergenic agents, analgesic agents, immune deficiency treating agents, immunosuppressive agents, immunomodulating agents, autoimmune disease treating agents, chronic rheumatoid arthritis treating agents, multiple sclerosis treating agents or the like.

Agonists to the cannabinoid type 2 receptor are known to suppress nephritis caused by rat Thy-1 antibody in WO97/29079. Therefore, the present compounds are useful as nephritis treating agents.

When using a compound of the present invention in treatment, it can be formulated into ordinary formulations for oral and parenteral administration. A pharmaceutical composition containing a compound of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulations, carriers, excipients, solvents and bases known to one ordinary skilled in the art may be used. Tablets are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrates (e.g., starch sodium glycolate) or lubricants (e.g., magnesium stearate). Tablets may be coated appropriately. In the case of liquid formulations such as syrups, solutions or suspensions, they may contain suspending agents (e.g., methyl cellulose), emulsifiers (e.g., lecithin), preservatives and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension.

Although an appropriate dosage of the present compound varies depending on the administration route, age, body weight, sex, or conditions of the patient, and the kind of drug(s) used together, if any, and should be determined by the physician in the end, in the case of oral administration, the daily dosage can generally be between about 0.01–100 mg, preferably about 0.01–10 mg, more preferably about 0.01–1 mg, per kg body weight. In the case of parenteral administration, the daily dosage can generally be between about 0.001–100 mg, preferably about 0.001–1 mg, more preferably about 0.001–0.1 mg, per kg body weight. The daily dosage can be administered in 1–4 divisions.

EXAMPLE

The following Examples are provided to further illustrate the present invention and are not to be construed as limiting the scope.

The meaning of each abbreviation are shown as follows.
Me: methyl, Et: ethyl, Pr: propyl, Pr$^i$: i-propyl,
Bu: butyl, Bu$^i$: i-butyl, Bu$^s$: sec-butyl,
Bu$^t$: t-butyl
Ph: phenyl, Ac: acetyl, Bn: benzyl
DMF: N,N-dimethylformamide, THF: tetrahydrofuran,
DEAD: diethyl azodicarboxylate, Reference Example 1-1

Preparation of (2-isopropylphenyl)isothiocyanate (Compound 2)

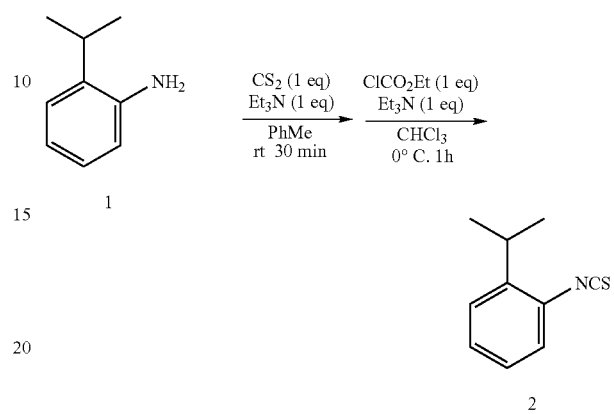

To a mixture of 2-isopropylaniline (5.00 g), triethylamine (3.74 g) and toluene (10 ml) was added dropwise for 10 minutes carbon dioxide (2.81 g). The mixture was stirred at room temperature for 1 hour and kept stationary for 12 hours. The reaction mixture was concentrated under reduced pressure. Dichloromethane (20 ml) and triethylamine (3.74 g) were added thereto. To the solution was added under ice-cooling for 10 minutes ethyl chlorocarbonate (4.01 g). The mixture was stirred at room temperature for 1 hour. To the reaction mixture was added 10% hydrochloric acid (20 ml). The mixture was extracted with dichloromethane (60 ml), dried over anhydrous magnesium sulfate and concentrated under reduced pressure to give (2-isopropylphenyl) isothiocyanate (6.55 g, yield: 99%) as yellow oil.

$^1$H-NMR (δ ppm TMS/CDCl$_3$) 1.25(6H, d, J=6.7), 3.25 (1H, q, J=6.7), 7.14–7.30(4H, m).

Reference Example 1-2

Preparation of (2-isopropylphenyl)isothiocyanate (Compound 2)

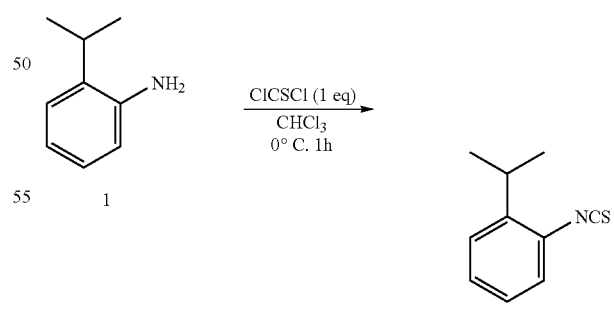

To a solution of 2-isopropylaniline (1.81 g) in diethylether (20 ml) was added dropwise under ice-cooling for 10 minutes thiophosgene (1.54 g). The mixture was stirred at room temperature for 1 hour.

To the reaction solution was added water (30 ml). The mixture was extracted with diethylether (60 ml), dried over anhydrous magnesium sulfate and concentrated under reduced pressure to give (2-isopropylphenyl)isothiocyanate (2.35 g, yield: 99%) as brown oil.

Reference Example 2

Preparation of N-(2-isopropylphenyl)-N'-(1-hydroxy-2,2-dimethyl)propylthiourea (Compound 3)

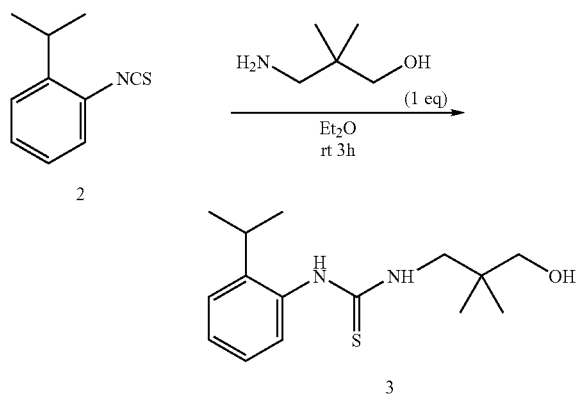

To a solution of (2-isopropylphenyl)isothiocyanate (3.30 g) in diethylether (20 ml) was added 3-amino-2,2-dimethylpropanol (1.92 g). The mixture was stirred at room temperature for 1 hour and concentrated under reduced pressure. The obtained residue was purified by silica gel column chromatography (n-hexane/ethyl acetate) to give N-(2-isopropylphenyl)-N'-(1-hydroxy-2,2-dimethyl)propylthiourea (4.60 g, yield: 88%) as yellow oil.

$^1$H-NMR (δ ppm TMS/CDCl$_3$) 0.82(6H, s), 1.25(6H, d, J=6.7), 3.11(1H, q, J=6.7), 3.25(2H, s), 3.55(2H, d, J=6.3), 6.05(1H, m), 7.17–7.40(4H, m).

Reference Example 3

Preparation of 2-(2-isopropylphenyl)imino-5,5-dimethyl-1,3-thiazine (Compound 4)

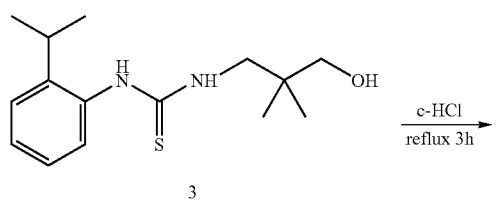

To N-(2-isopropylphenyl)-N'-(1-hydroxy-2,2-dimethyl)propylthiourea (10.37 g) was added concentrated hydrochloric acid (5 ml). The mixture was refluxed for 3 hours. The reaction solution was cooled to room temperature and poured into an aqueous solution of 20% sodium hydroxide (25 ml). The precipitated crystal was filtered and recrystallized with ethyl acetate to give 2-(2-isopropylphenyl)imino-5,5-dimethyl-1,3-thiazine (4.80 g, yield: 50%) as a white crystal.

M.p. 155–157° C.

$^1$H-NMR (δ ppm TMS/CDCl$_3$) 1.15(6H, s), 1.20(6H, d, J=6.7), 2.67(2H, s), 3.09(2H, s), 3.15(1H, q, J=6.7), 6.88 (1H, m), 7.05–7.11(2H, m), 7.20(1H, m).

Reference Example 4

Preparation of 2-(2-isopropylphenyl)imino-5,5-dimethyl-1,3-thiazine (Compound 4)

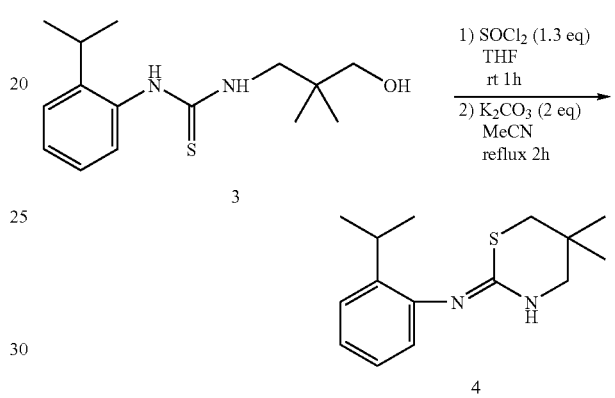

To a solution of N-(2-isopropylphenyl)-N'-(1-hydroxy-2,2-dimethyl)propylthiourea (1.00 g) in tetrahydrofuran (6 ml) was added dropwise thionylchloride (0.60 g). The mixture was stirred at room temperature for 1 hour and concentrated under reduced pressure. To the solution were added acetonitrile (20 ml) and potassium carbonate (0.93 g). The mixture was refluxed for 2 hours. To the solution was added water (40 ml). The mixture was extracted with dichloromethane (60 ml), dried over anhydrous magnesium sulfate and concentrated under reduced pressure. The obtained residue was purified by silica gel column chromatography (n-hexane/ethyl acetate) to give 2-(2-isopropylphenyl)imino-5,5-dimethyl-1,3-thiazine (0.45 g, yield: 48%) as a white crystal.

The following Examples 1 to 5 were carried out by using 2-(2-isopropylphenyl)imino-5,5-dimethyl-1,3-thiazine prepared in Reference Example 3 and 4.

Example 1

Preparation of 3-ethyl-2-(2-isopropylphenyl)imino-5,5-dimethyl-1,3-thiazine (Compound I-1)

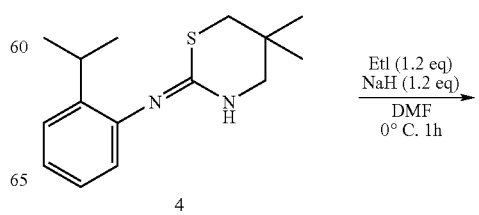

-continued

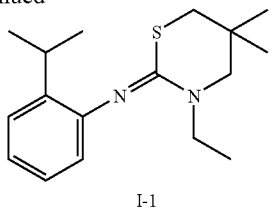

I-1

To a solution of 2-(2-isopropylphenyl)imino-5,5-dimethyl-1,3-thiazine (0.26 g) in N,N-dimethylformamide (2 ml) was added under ice-cooling 60% sodium hydride (0.05 g). The mixture was stirred for 30 minutes. Ethyliodide (0.17 g) was added thereto. The mixture was stirred at room temperature for 2 hours. To a reaction mixture was added water (30 ml), extracted with diethylether (60 ml), dried over anhydrous magnesium sulfate and concentrated under reduced pressure. The obtained residue was purified by silica gel column chromatography (n-hexane/ethyl acetate) to give 3-ethyl-2-(2-isopropylphenyl)imino-5,5-dimethyl-1,3-thiazine (0.21 g, yield: 71%) as colorless oil.

$^1$H-NMR (δ ppm TMS/CDCl$_3$) 1.13 (6H, s), 1.20 (6H, d, J=6.9), 1.25 (3H, t, J=7.4), 2.61 (2H, s),3.05 (2H, s), 3.17 (1H, m), 3.64 (2H, q, J=6.9), 6.72–6.80 (1H, m), 6.98–7.07 (2H, m), 7.20–7.32 (1H, m).

Example 2

Preparation of 2-(2-isopropylphenyl)imino-3-propionyl-5,5-dimethyl-1,3-thiazine (Compound I-2)

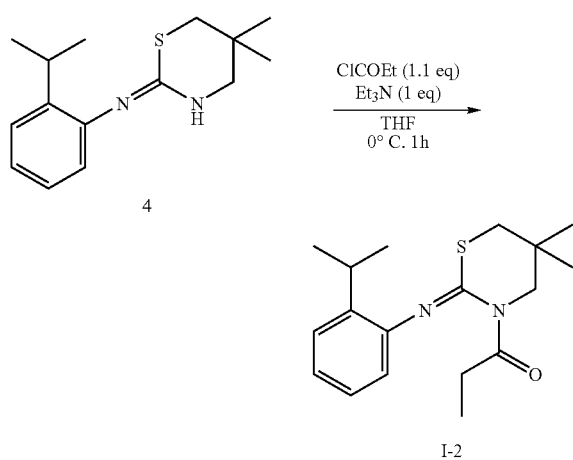

To a mixture of 2-(2-isopropylphenyl)imino-5,5-dimethyl-1,3-thiazine (0.26 g), triethylamine (0.15 g) and dichloromethane (5 ml) was added dropwise for 5 minutes propionylchloride (0.13 g). The mixture was stirred at room temperature for 2 hours. To the solution was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 2-(2-isopropylphenyl)imino-3-propionyl-5,5-dimethyl-1,3-thiazine (0.18 g, yield: 56%) as colorless oil.

$^1$H-NMR (δ ppm TMS/CDCl$_3$)1.14 (6H, s), 1.20 (6H, d, J=6.9), 1.22 (3H, t, J=7.4), 2.60 (2H, s), 2.95 (2H, q, J=7.4), 2.96 (1H, q, J=6.9), 3.73 (2H, s), 6.73–6.78 (1H, m), 7.10–7.17 (2H, m), 7.25–7.32 (1H, m).

Example 3

Preparation of 3-(ethoxycarbonyl)-2-(2-isopropylphenyl)imino-5,5-dimethyl-1,3-thiazine (Compound I-3)

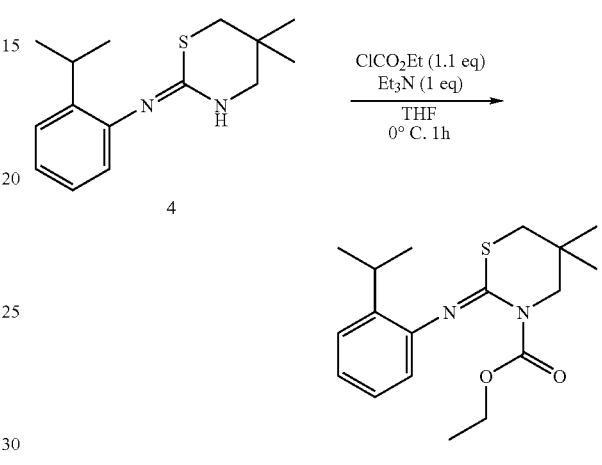

To a mixture of 2-(2-isopropylphenyl)imino-5,5-dimethyl-1,3-thiazine (0.26 g), triethylamine (0.15 g) and dichloromethane (5 ml) was added dropwise for 5 minutes ethyl chlorocarbonate (0.13 g). The mixture was stirred at room temperature for 2 hours. To the solution was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 3-(ethoxycarbonyl)-2-(2-isopropylphenyl)imino-5,5-dimethyl-1,3-thiazine (0.23 g, yield: 68%) as a white crystal. M.p. 84–86° C.

$^1$H-NMR (δ ppm TMS/CDCl$_3$) 1.16 (6H, s), 1.21 (6H, d, J=6.9), 1.36 (3H, t, J=7.1), 2.59 (2H, s), 3.17 (1H, q, J=6.9), 3.65 (2H, s), 4.32 (2H, q, J=7.1), 6.74–6.78 (1H, m), 7.12–7.16 (2H, m), 7.30–7.36 (1H, m).

Example 4

Preparation of 3-(ethylthiocarbonyl)-2-(2-isopropylphenyl)imino-5,5-dimethyl-1,3-thiazine (Compound I-4)

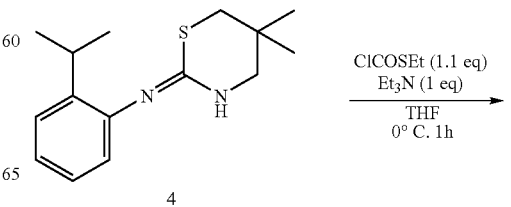

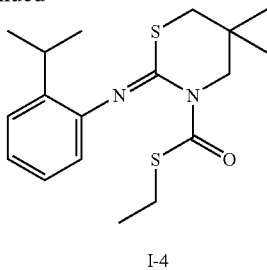

I-4

To a mixture of 2-(2-isopropylphenyl)imino-5,5-dimethyl-1,3-thiazine (1.00 g), triethylamine (0.58 g) and dichloromethane (5 ml) was added dropwise for 5 minutes ethyl chlorothiocarbonate (0.56 g). The mixture was stirred at room temperature for 1 hour. To the solution was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 3-(ethylthiocarbonyl)-2-(2-isopropylphenyl)imino-5,5-dimethyl-1,3-thiazine (0.74 g, yield: 56%) as colorless oil.

$^1$H-NMR (δ ppm TMS/CDCl$_3$)1.16 (6H, s), 1.21 (6H, d, J=6.9), 1.36 (3H, t, J=7.1), 2.63 (2H, s), 2.89 (2H, q, J=7.1), 3.15 (1H, q, J=6.9), 3.77 (2H, s), 6.79–6.85 (1H,m), 7.12–7.16 (2H, m), 7.30–7.36 (1H, m).

Example 5

Preparation of 2-(2-isopropylphenyl)imino-3-(methylthio)thiocarbonyl-5,5-dimethyl-1,3-thiazine (Compound I-5)

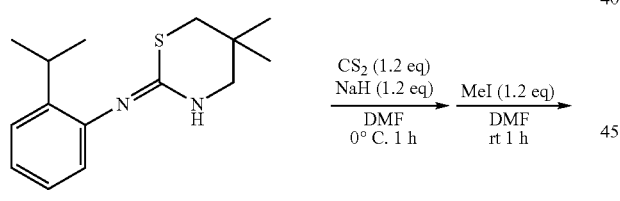

To a mixture of 2-(2-isopropylphenyl)imino-5,5-dimethyl-1,3-thiazine (0.26 g), carbon dioxide (0.09 g) and N,N-dimethylformamide (2 ml) was added under ice-cooling 60% sodium hydride (0.05 g). The mixture was stirred for 30 minutes. Methyliodide (0.17 g) was added thereto. The mixture was stirred at room temperature for 2 hours. To the solution was added water (30 ml), extracted with diethylether (60 ml), dried over anhydrous magnesium sulfate and concentrated under reduced pressure. The obtained residue was purified by silica gel column chromatography (n-hexane/ethyl acetate) to give 2-(2-isopropylphenyl)imino-3-(methylthio)thiocarbonyl-5,5-dimethyl-1,3-thiazine (0.14 g, yield: 40%) as a yellow crystal. M.p. 77–79° C.

$^1$H-NMR (δ ppm TMS/CDCl$_3$)1.20 (6H, d, J=6.9), 1.23 (6H, s), 2.65 (3H, s), 2.68 (2H, s), 3.11 (1H, q, J=6.9), 4.51 (2H, s), 6.83–6.90 (1H, m), 7.11–7.18 (2H, m), 7.28–7.35 (1H, m).

The following Reference Example 5 was carried out in accordance with Reference Example 2 and 3.

Reference Example 5

Preparation of 2-(2-isopropylphenyl)imino-1,3-thiazolidine (Compound 6)

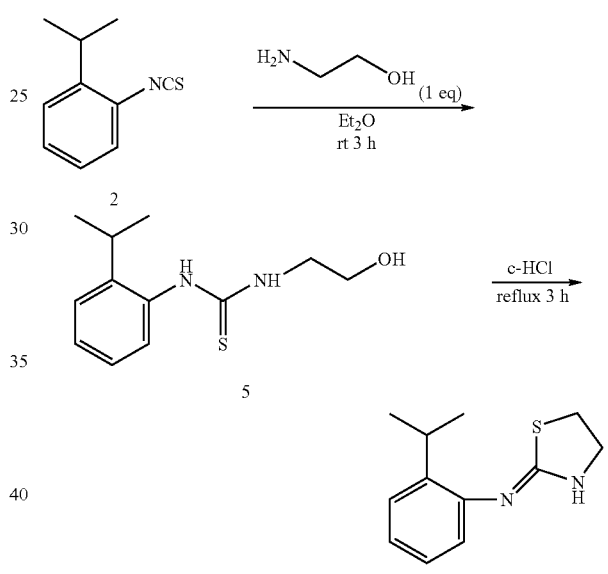

To a solution of (2-isopropylphenyl)isothiocyanate (2.00 g) in diethylether (20 ml) was added 2-aminoethanol (0.69 g). The mixture was stirred at room temperature for 1 hour and concentrated under reduced pressure. To the obtained oil was added concentrated hydrochloric acid (5 ml). The mixture was refluxed for 3 hours. The reaction mixture was cooled to room temperature and poured into an aqueous solution of 20% sodium hydroxide (25 ml). The mixture was extracted with dichloromethane (60 ml), dried over anhydrous magnesium sulfate and concentrated under reduced pressure. The obtained residue was purified by silica gel column chromatography (n-hexane/ethyl acetate) to give 2-(2-isopropylphenyl)imino-1,3-thiazolidine (1.80 g, yield: 73%) as a white crystal. M.p. 76–77° C.

$^1$H-NMR (δ ppm TMS/CDCl$_3$) 1.20(6H, d, J=6.7), 3.15 (1H, q, J=6.7), 3.27(2H, t, J=6.7), 3.67(2H, t, J=6.7), 6.95–6.99(1H, m), 7.05–7.19(2H, m), 7.22–7.26(1H, m).

The following Example 6 and 7 were carried out by using 2-(2-isopropylphenyl)imino-1,3-thiazolidine prepared in Reference Example 5.

Example 6

Preparation of 3-(ethylthiocarbonyl)-2-(2-isopropylphenyl)imino-1,3-thiazolidine (Compound I-6)

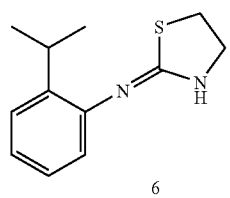

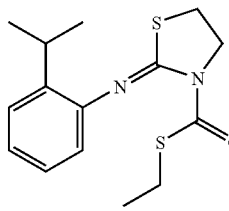

To a mixture of 2-(2-isopropylphenyl)imino-1,3-thiazolidine (0.25 g), triethylamine (0.15 g) and dichloromethane (5 ml) was added dropwise for 5 minutes ethyl chlorothiocarboxylate (0.15 g). The mixture was stirred for 2 hours. To the solution was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 3-(ethylthiocarbonyl)-2-(2-isopropylphenyl)imino-1,3-thiazolidine (0.27 g, yield: 77%) as a white crystal. M.p. 79–81° C.

$^1$H-NMR (δ ppm TMS/CDCl$_3$) 1.20 (6H, d, J=6.9), 1.30 (3H, t, J=7.4), 2.90 (2H, t, J=7.4), 3.15 (2H, t, J=7.4), 3.20 (1H, q, J=6.9), 4.31 (2H, t, J=7.4), 6.79–6.82 (1H, m), 7.07–7.16 (2H, m), 7.28–7.32 (1H, m).

Example 7

Preparation of 2-(2-isopropylphenyl)imino-3-(methylthio)thiocarbonyl-1,3-thiazolidine (Compound I-7)

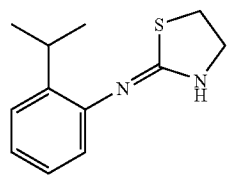

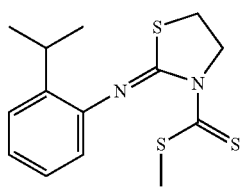

To a mixture of 2-(2-isopropylphenyl)imino-1,3-thiazolidine (0.22 g), carbon disulfide (0.09 g) and N,N-dimethylformamide (2 ml) was added under ice-cooling 60% sodium hydride (0.05 g). The mixture was stirred for 30 minutes. Methyliodide (0.17 g) was added thereto. The mixture was stirred at room temperature for 2 hours. To the mixture was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 2-(2-isopropylphenyl)imino-3-(methylthio)thiocarbonyl-1,3-thiazolidine (0.14 g, yield: 45%) as colorless oil.

$^1$H-NMR (δ ppm TMS/CDCl$_3$) 1.23 (6H, d, J=6.9), 2.65 (3H, s), 2.90 (2H, t, J=7.4), 3.20 (1H, q, J=6.9), 4.45 (2H, t, J=7.4), 6.79–6.82 (1H, m), 7.07–7.16 (2H, m), 7.28–7.32 (1H, m).

Reference Example 6

Preparation of (2-methoxybenzyl)isothiocyanate (Compound 8)

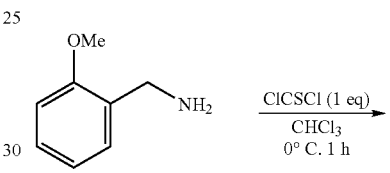

To a solution of 2-methoxybenzylamine (1.80 g) in diethylether (20 ml) was added dropwise under ice-cooling for 10 minutes thiophosgene (1.54 g). The mixture was stirred at room temperature for 1 hour. To the reaction solution was added water (30 ml), extracted with diethylether (60 ml), dried over anhydrous magnesium sulfate and concentrated under reduced pressure to give (2-methoxybenzyl)isothiocyanate (2.35 g, yield: 99%) as brown oil.

$^1$H-NMR (δ ppm TMS/CDCl$_3$) 3.86(3H, s), 4.70(2H, s), 6.88 (1H, d, J=7.4), 6.98(1H, t, J=7.4), 7.24–7.30(2H, m).

Reference Example 7

Preparation of N-(2-methoxybenzyl)-N'-(1-hydroxy-2,2-dimethyl)propylthiourea (Compound 9)

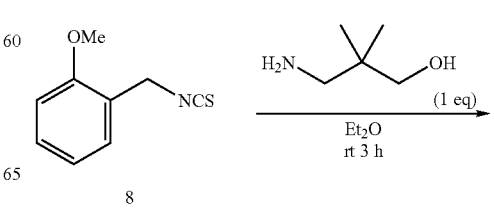

-continued

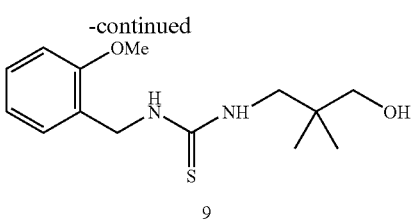

9

To a solution of (2-methoxybenzyl)isothiocyanate (2.35 g) in diethylether (20 ml) was added 3-amino-2,2-dimethylpropanol (1.34 g). The mixture was stirred at room temperature for 1 hour. The mixture was concentrated under reduced pressure. The obtained residue was purified by silica gel column chromatography (n-hexane/ethyl acetate) to give N-(2-methoxybenzyl)-N'-(1-hydroxy-2,2-dimethyl)propylthiourea (3.70 g, yield: 99%) as colorless oil.

$^1$H-NMR (δ ppm TMS/CDCl$_3$) 0.82(6H, s), 3.25(2H, s), 3.55(2H, d, J=6.3), 3.86(3H, s), 4.70(2H, s), 6.50(1H, brs), 6.88(1H, d, J=7.4), 6.95(1H, t, J=7.4), 7.24–7.30(2H, m).

Reference Example 8

Preparation of 2-(2-methoxybenzyl)imino-5,5-dimethyl-1,3-thiazine (Compound 10)

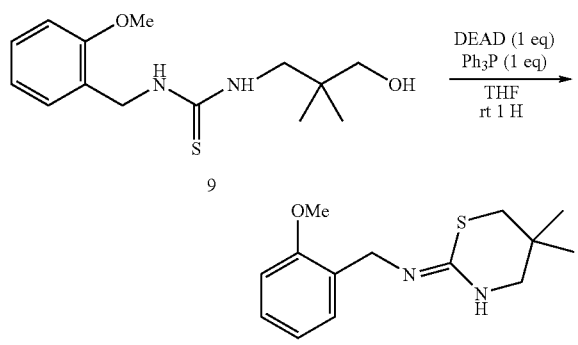

To a mixture of N-(2-methoxybenzyl)-N'-(1-hydroxy-2,2-dimethyl)propylthiourea (3.70 g), triphenylphosphine (3.44 g) and tetrahydrofuran (20 ml) was added dropwise for 10 minutes diethyl azodicarboxylate (2.28 g). The mixture was stirred at room temperature for 2 hours. To the solution was added water (40 ml). The mixture was extracted with dichloromethane (90 ml), dried over anhydrous magnesium sulfate and concentrated under reduced pressure. The obtained residue was purified by silica gel column chromatography (n-hexane/ethyl acetate) to give 2-(2-methoxybenzyl)imino-5,5-dimethyl-1,3-thiazine (0.87 g, yield: 25%) as colorless oil.

$^1$H-NMR (δ ppm TMS/CDCl$_3$) 1.05(6H, s,), 2.75(2H, s), 3.23(2H, s), 3.83(3H, s), 4.41(2H, s), 6.86–6.95(1H, m), 7.20–7.30(1H, m), 7.44–7.48 (2H, m).

The following Examples 8 and 9 were carried out by using 2-(2-methoxybenzyl)imino-5,5-dimethyl-1,3-thiazine prepared in Reference Example 8.

Example 8

Preparation of 3-(ethylthiocarbonyl)-2-(2-methoxybenzyl)imino-5,5-dimethyl-1,3-thiazine (Compound I-8)

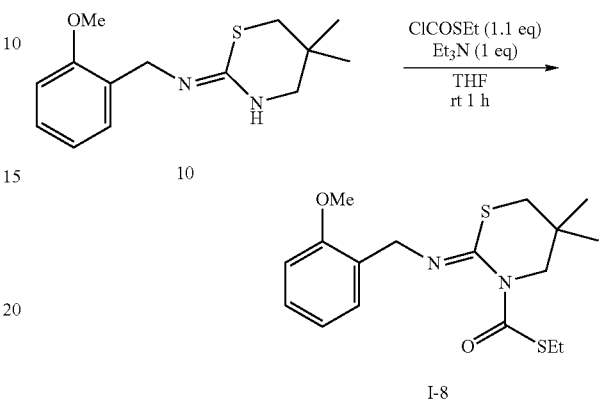

To a mixture of 2-(2-methoxybenzyl)imino-5,5-dimethyl-1,3-thiazine (0.28 g), triethylamine (0.15 g) and dichloromethane (5 ml) was added dropwise for 5 minutes ethyl chlorothiocarboxylate (0.17 g). The mixture was stirred at room temperature for 1 hour. To the reaction solution was added water (30 ml), extracted with diethylether (60 ml), dried over anhydrous magnesium sulfate and concentrated under reduced pressure. The obtained residue was purified by silica gel column chromatography (n-hexane/ethyl acetate) to give 3-(ethylthiocarbonyl)-2-(2-methoxybenzyl)imino-5,5-dimethyl-1,3-thiazine (0.20 g, yield: 57%) as colorless oil.

$^1$H-NMR (δ ppm TMS/CDCl$_3$) 1.15 (6H, s), 1.25 (3H, t, J=7.4), 2.69 (2H, s), 2.83 (2H, q, J=7.4), 3.69 (2H, s), 3.84 (3H, s), 4.61 (2H, s), 6.86 (1H, d, J=8.2), 6.96 (1H, t, J=8.2), 7.26 (1H, t, J=8.2), 7.55 (1H, t, J=8.2).

Example 9

Preparation of 2-(2-methoxybenzyl)imino-3-(methylthio)thiocarbonyl-5,5-dimethyl-1,3-thiazine (Compound I-9)

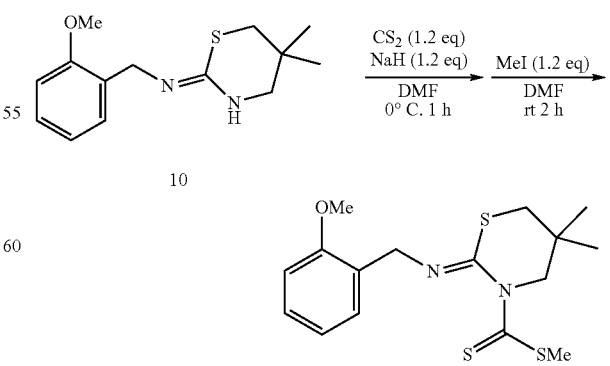

To a mixture of 2-(2-methoxybenzyl)imino-5,5-dimethyl-1,3-thiazine(0.27 g), carbon disulfide (0.09 g) and N,N-dimethylformamide (2 ml) was added under ice-cooling 60% sodium hydride (0.05 g). The mixture was stirred for 30 minutes. Methyl iodide (0.17 g) was added thereto. The mixture was stirred at room temperature for 2 hours. To the solution was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 2-(2-methoxybenzyl)imino-3-(methylthio)thiocarbonyl-5,5-dimethyl-1,3-thiazine (0.20 g, yield: 57%) as colorless oil.

$^1$H-NMR (δ ppm TMS/CDCl$_3$) 1.25 (6H, s), 2.56 (3H, s), 2.72 (2H, s), 3.85 (3H, s), 4.43 (2H, s), 4.63 (2H, s), 6.86–6.88(2H, m), 7.20–7.30 (1H, m), 7.44–7.48 (1H, m).

Reference Example 9

Preparation of (2-methoxyphenethyl)isothiocyanate (Compound 12)

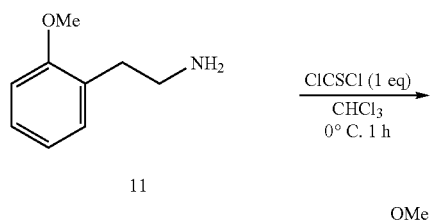

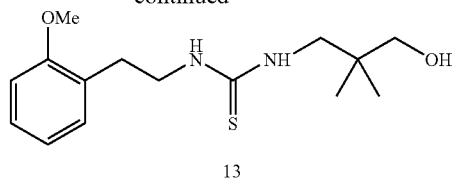

To a solution of 2-methoxyphenethylamine (1.98 g) in diethylether (20 ml) was added dropwise under ice-cooling thiophosgene (1.54 g). The mixture was stirred at room temperature for 1 hour. To the solution was added water (30 ml). The mixture was extracted with diethylether (60 ml), dried over anhydrous magnesium sulfate and concentrated under reduced pressure to give (2-methoxyphenethyl)isothiocyanate (1.80 g, yield: 71%) as brown oil.

$^1$H-NMR (δ ppm TMS/CDCl$_3$) 3.00(2H, t, J=7.4), 3.70 (2H, t, J=7.4), 3.86(3H, s), 6.88–6.95(2H, m), 7.15(1H, d, J=7.4), 7.24(1H, t, J=7.4).

Reference Example 10

Preparation of N-(2-methoxyphenethyl)-N'-(1-hydroxy-2,2-dimethyl)propylthiourea (Compound 13)

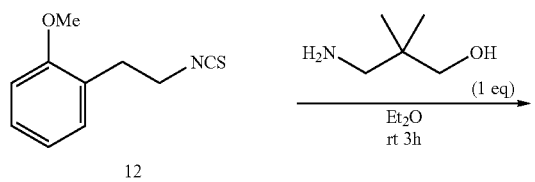

To a solution of (2-methoxyphenethyl)isothiocyanate (2.35 g) in diethylether (20 ml) was added 3-amino-2,2-dimethylpropanol (1.34 g). The mixture was stirred at room temperature for 1 hour. The mixture was concentrated under reduced pressure. The obtained residue was purified by silica gel column chromatography (n-hexane/ethyl acetate) to give N-(2-methoxyphenethyl)-N'-(1-hydroxy-2',2-dimethyl)propylthiourea (2.45 g, yield 89%) as colorless oil.

$^1$H-NMR (δ ppm TMS/CDCl$_3$) 0.82(6H, s), 2.90(2H, t, J=7.4), 3.25(2H, s), 3.55(2H, d, J=6.3), 3.70(2H, t, J=7.4), 3.86(3H, s), 6.50(1H, brs), 6.88–6.95(2H, m), 7.15(1H, m), 7.24(1H, m).

Reference Example 11

Preparation of 2-(2-methoxyphenethyl)imino-5,5-dimethyl-1,3-thiazine (Compound 14)

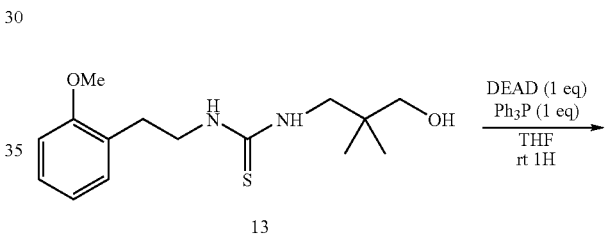

To a mixture of N-(2-methoxyphenethyl)-N'-(1-hydroxy-2,2-dimethyl)propylthiourea (2.40 g), triphenylphosphine (2.12 g) and tetrahydrofuran (20 ml) was added dropwise for 10 minutes diethyl azodicarboxylate (2.28 g). The mixture was stirred at room temperature for 2 hours. To the solution was added water (40 ml). The mixture was extracted with dichloromethane (90 ml), dried over magnesium sulfate and concentrated under reduced pressure. The obtained residue was purified by silica gel column chromatography (n-hexane/ethyl acetate) to give 2-(2-methoxyphenethyl)imino-5,5-dimethyl-1,3-thiazine (0.70 g, yield: 31%) as colorless oil.

$^1$H-NMR (δ ppm TMS/CDCl$_3$) 1.05(6H, s,), 2.72(2H, s), 2.80(2H, t, J=7.4), 3.25(2H, s), 3.55(2H, d, J=6.3), 3.83(3H, s), 6.83–6.95(2H, m), 7.15(1H, m), 7.24(1H, m).

The following Examples 10 and 11 were carried out by using 2-(2-methoxyphenethyl)imino-5,5-dimethyl-1,3-thiazine prepared in Example 11.

Example 10

Preparation of 3-(ethylthiocarbonyl)-2-(2-methoxyphenethyl)imino-5,5-dimethyl-1,3-thiazine (Compound I-10)

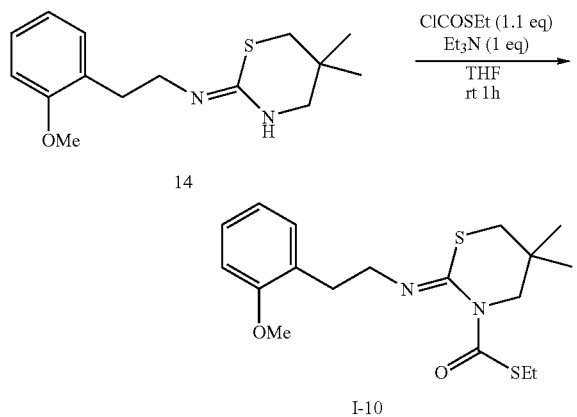

To a mixture of 2-(2-methoxyphenethyl)imino-5,5-dimethyl-1,3-thiazine (0.28 g), triethylamine (0.15 g) and dichloromethane (5 ml) was added dropwise for 3 minutes ethyl chlorothiocarbonate (0.15 g). The mixture was stirred at room temperature for 2 hours. To the solution was added water (30 ml). The mixture was extracted with diethylether (60 ml), dried over anhydrous magnesium sulfate and concentrated under reduced pressure. The obtained residue was purified by silica gel column chromatography (n-hexane/ethyl acetate) to give 2-(2-methoxyphenethyl)imino-N-(ethylthiocarbamoyl)-5,5-dimethyl-1,3-thiazine (0.21 g, yield: 60%) as colorless oil.

$^1$H-NMR (δ ppm TMS/CDCl$_3$) 1.11 (6H, s), 1.26 (3H, t, J=7.4), 2.61 (2H, s), 2.83 (2H, q, J=7.4), 2.99–3.05 (2H, m), 3.61–3.66 (2H, m), 3.62 (2H, s), 3.82 (3H, s), 6.86–6.91 2H, m), 7.17–7.26 (2H, m).

Example 11

Preparation of 2-(2-methoxyphenethyl)imino-3-(methylthio)thiocarbonyl-5,5-dimethyl-1,3-thiazine (Compound I-11)

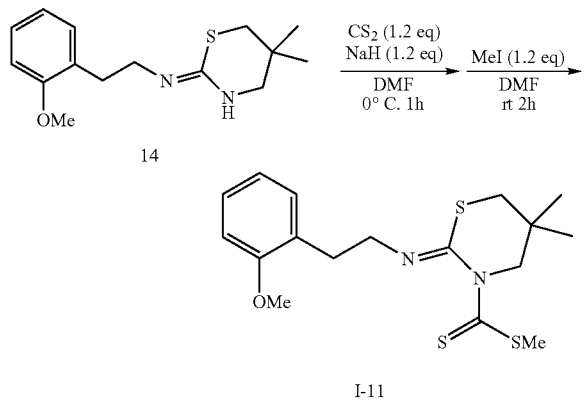

To a mixture of 1-(1-methoxyphenethyl)imino-5,5-dimethyl-1,3-thiazine (0.28 g), carbondisulfide (0.09 g) and N,N-dimethylformamide (2 ml) was added under ice-cooling 60% sodium hydride (0.05 g). The mixture was stirred for 30 minutes. Methyliodide (0.17 g) was added thereto. The mixture was stirred at room temperature for 2 hours. To the solution was added water (30 ml). The mixture was extracted with diethylether (60 ml), dried over anhydrous magnesium sulfate and concentrated under reduced pressure. The obtained residue was chromatographed (n-hexane/ethyl acetate) to give 2-(2-methoxyphenethyl)imino-3-(methylthio)thiocarbonyl-5,5-dimethyl-1,3-thiazine (0.18 g, yield: 50%) as colorless oil.

$^1$H-NMR (δ ppm TMS/CDCl$_3$) 1.19 (6H, s), 2.55 (3H, s), 2.64 (2H, s), 3.05 (2H, t, J=7.5), 3.66 (2H, t, J=7.5), 3.84 (3H, s), 4.35 (2H, s), 6.84–6.91 (2H, m), 7.17–7.30 (2H, m).

The compounds shown in the following tables were prepared in accordance with the above Example. The numbers of left column in Tables represent Compound No.

TABLE 1

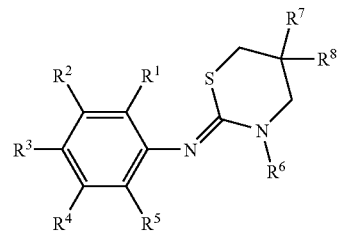

| | R$^1$ | R$^2$ | R$^3$ | R$^4$ | R$^5$ | R$^6$ | R$^7$ | R$^8$ |
|---|---|---|---|---|---|---|---|---|
| I-16 | H | H | H | H | H | COSEt | Me | Me |
| I-17 | F | H | H | H | H | COSEt | Me | Me |
| I-18 | Cl | H | H | H | H | COSEt | Me | Me |
| I-19 | Me | H | H | H | H | COSEt | Me | Me |
| I-20 | Et | H | H | H | H | COSEt | Me | Me |
| I-21 | Pr | H | H | H | H | COSEt | Me | Me |
| I-22 | Bu | H | H | H | H | COSEt | Me | Me |
| I-23 | Bu$^s$ | H | H | H | H | COSEt | Me | Me |
| I-24 | Bu$^t$ | H | H | H | H | COSEt | Me | Me |
| I-25 | Ph | H | H | H | H | COSEt | Me | Me |
| I-26 | CF$_3$ | H | H | H | H | COSEt | Me | Me |
| I-27 | OMe | H | H | H | H | COSEt | Me | Me |
| I-28 | OEt | H | H | H | H | COSEt | Me | Me |
| I-29 | OPr$^i$ | H | H | H | H | COSEt | Me | Me |
| I-30 | SMe | H | H | H | H | COSEt | Me | Me |
| I-31 | SEt | H | H | H | H | COSEt | Me | Me |
| I-32 | SPr$^i$ | H | H | H | H | COSEt | Me | Me |
| I-33 | NMe$_2$ | H | H | H | H | COSEt | Me | Me |
| I-34 | H | Pr$^i$ | H | H | H | COSEt | Me | Me |
| I-35 | H | H | Cl | H | H | COSEt | Me | Me |
| I-36 | H | H | Pr$^i$ | H | H | COSEt | Me | Me |
| I-37 | H | H | NO$_2$ | H | H | COSEt | Me | Me |
| I-38 | Me | Me | H | H | H | COSEt | Me | Me |
| I-39 | Me | H | Me | H | H | COSEt | Me | Me |
| I-40 | Me | H | H | Me | H | COSEt | Me | Me |
| I-41 | Me | H | H | H | Me | COSEt | Me | Me |
| I-42 | H | Me | Me | H | H | COSEt | Me | Me |
| I-43 | H | Me | H | Me | H | COSEt | Me | Me |
| I-44 | Me | H | Cl | H | H | COSEt | Me | Me |

TABLE 2

| | R¹ | R² | R³ | R⁴ | R⁵ | R⁶ | R⁷ | R⁸ |
|---|---|---|---|---|---|---|---|---|
| I-45 | Cl | H | Me | H | H | COSEt | Me | Me |
| I-46 | Pr$^i$ | H | NO$_2$ | H | H | COSEt | Me | Me |
| I-47 | Pr$^i$ | H | H | H | NO$_2$ | COSEt | Me | Me |
| I-48 | NO$_2$ | H | NO$_2$ | H | H | COSEt | Me | Me |
| I-49 | Pr | H | H | H | H | COSMe | Me | Me |
| I-50 | Pr$^i$ | H | H | H | H | COSMe | Me | Me |
| I-51 | Bu$^s$ | H | H | H | H | COSMe | Me | Me |
| I-52 | H | Pr$^i$ | H | H | H | COSMe | Me | Me |
| I-53 | H | OMe | OMe | H | H | COSMe | Me | Me |
| I-54 | H | —OCH$_2$O— | | H | H | COSMe | Me | Me |
| I-55 | H | OMe | OMe | OMe | H | COSMe | Me | Me |
| I-56 | Et | H | H | H | H | CSSMe | Me | Me |
| I-57 | Bu$^s$ | H | H | H | H | CSSMe | Me | Me |
| I-58 | CH$_2$OMe | H | H | H | H | CSSMe | Me | Me |
| I-59 | CH(Me)OMe | H | H | H | H | CSSMe | Me | Me |
| I-60 | OMe | H | H | H | H | CSSMe | Me | Me |
| I-61 | OEt | H | H | H | H | CSSMe | Me | Me |
| I-62 | SMe | H | H | H | H | CSSMe | Me | Me |
| I-63 | SEt | H | H | H | H | CSSMe | Me | Me |
| I-64 | SPr$^i$ | H | H | H | H | CSSMe | Me | Me |
| I-65 | SOMe | H | H | H | H | CSSMe | Me | Me |
| I-66 | SO$_2$Me | H | H | H | H | CSSMe | Me | Me |
| I-67 | SOEt | H | H | H | H | CSSMe | Me | Me |
| I-68 | NMe$_2$ | H | H | H | H | CSSMe | Me | Me |
| I-69 | H | Pr$^i$ | H | H | H | CSSMe | Me | Me |
| I-70 | H | H | Cl | H | H | CSSMe | Me | Me |

TABLE 3

| | R¹ | R² | R³ | R⁴ | R⁵ | R⁶ | R⁷ | R⁸ |
|---|---|---|---|---|---|---|---|---|
| I-71 | Me | H | Me | H | H | CSSMe | Me | Me |
| I-72 | Me | H | H | Me | H | CSSMe | Me | Me |
| I-73 | Me | H | H | H | Me | CSSMe | Me | Me |
| I-74 | H | Me | H | H | H | CSSMe | Me | Me |
| I-75 | H | Me | H | Me | H | CSSMe | Me | Me |
| I-76 | OMe | OMe | H | H | H | CSSMe | Me | Me |
| I-77 | H | OMe | OMe | H | H | CSSMe | Me | Me |
| I-78 | OMe | H | H | OMe | H | CSSMe | Me | Me |
| I-79 | OMe | H | OMe | H | H | CSSMe | Me | Me |
| I-80 | H | —OCH$_2$O— | | H | H | CSSMe | Me | Me |
| I-81 | Pr$^i$ | H | NO$_2$ | H | H | CSSMe | Me | Me |
| I-82 | Pr$^i$ | H | H | H | NO$_2$ | CSSMe | Me | Me |
| I-83 | H | OMe | OMe | OMe | H | CSSMe | Me | Me |
| I-84 | Pr$^i$ | H | H | H | H | CSSEt | Me | Me |
| I-85 | Bu$^s$ | H | H | H | H | CSSEt | Me | Me |
| I-86 | OEt | H | H | H | H | CSSEt | Me | Me |
| I-87 | SMe | H | H | H | H | CSSEt | Me | Me |

TABLE 3-continued

| | R¹ | R² | R³ | R⁴ | R⁵ | R⁶ | R⁷ | R⁸ |
|---|---|---|---|---|---|---|---|---|
| I-88 | H | Pr$^i$ | H | H | H | CSSEt | Me | Me |
| I-118 | H | OEt | OEt | H | H | CSSMe | Me | Me |
| I-119 | OMe | H | Me | H | H | CSSMe | Me | Me |
| I-120 | OMe | H | H | Me | H | CSSMe | Me | Me |
| I-121 | H | OMe | Me | H | H | CSSMe | Me | Me |
| I-122 | Me | Me | H | H | H | CSSMe | Me | Me |
| I-123 | N(Me)Ac | H | H | H | H | CSSMe | Me | Me |

TABLE 4

| | R⁶ | R⁷ | R⁸ |
|---|---|---|---|
| I-89 | COPr | Me | Me |
| I-90 | COOMe | Me | Me |
| I-91 | COOPr | Me | Me |
| I-92 | CONHEt | Me | Me |
| I-93 | COCH$_2$OMe | Me | Me |
| I-94 | COCH$_2$SMe | Me | Me |
| I-95 | COCH$_2$SEt | Me | Me |
| I-96 | CSOEt | Me | Me |
| I-97 | CSNHEt | Me | Me |
| I-98 | CSSPr | Me | Me |
| I-99 | CSSPr$^i$ | Me | Me |
| I-100 | CSSBn | Me | Me |

TABLE 5

| | R¹ | R² | R³ | n | R⁶ | R⁷ | R⁸ |
|---|---|---|---|---|---|---|---|
| 1-101 | H | H | Cl | 1 | COSEt | Me | Me |
| 1-102 | H | H | Cl | 1 | CSSMe | Me | Me |
| 1-103 | Cl | H | Cl | 2 | COSEt | Me | Me |
| 1-104 | Cl | H | Cl | 2 | CSSMe | Me | Me |

TABLE 6

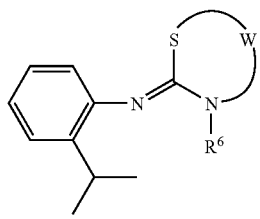

| | R⁶ | W |
|---|---|---|
| I-105 | COSEt | (S-CH2CH2CH2-N) |
| I-106 | COSEt | (S-CH2CH(Me)CH2-N... ) |
| I-107 | COSEt | |
| I-108 | COSEt | |
| I-109 | COSEt | |
| I-110 | COSEt | |
| I-111 | COSEt | |
| I-112 | COSEt | |
| I-113 | CSSMe | |
| I-114 | CSSMe | |

TABLE 6-continued

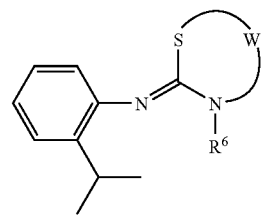

| | R⁶ | W |
|---|---|---|
| I-115 | CSSMe | |
| I-116 | CSSMe | |
| I-117 | CSSMe | |

TABLE 7

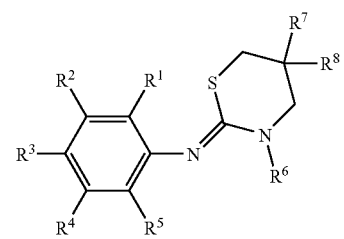

| | R¹ | R² | R³ | R⁴ | R⁵ | R⁶ | R⁷ | R⁸ |
|---|---|---|---|---|---|---|---|---|
| I-124 | H | H | OEt | H | H | CSSMe | Me | Me |
| I-125 | H | OEt | H | H | H | CSSMe | Me | Me |
| I-126 | H | H | OMe | H | H | CSSMe | Me | Me |
| I-127 | H | OMe | H | H | H | CSSMe | Me | Me |
| I-128 | H | OEt | OMe | H | H | CSSMe | Me | Me |
| I-129 | H | OPr | OMe | H | H | CSSMe | Me | Me |
| I-130 | H | OEt | OEt | H | H | CSSMe | Me | Me |
| I-131 | H | H | OPr | H | H | CSSMe | Me | Me |
| I-132 | H | OPr | H | H | H | CSSMe | Me | Me |
| I-133 | H | H | OBu | H | H | CSSMe | Me | Me |
| I-134 | H | OBu | H | H | H | CSSMe | Me | Me |
| I-135 | H | OMe | OEt | H | H | CSSMe | Me | Me |
| I-136 | H | OMe | OPr | H | H | CSSMe | Me | Me |
| I-137 | H | OBu | OMe | H | H | CSSMe | Me | Me |
| I-138 | H | H | OPrⁱ | H | H | CSSMe | Me | Me |
| I-139 | H | OPrⁱ | H | H | H | CSSMe | Me | Me |
| I-140 | H | H | H | H | H | CSSMe | Me | Me |
| I-141 | F | H | H | H | H | CSSMe | Me | Me |
| I-142 | Cl | H | H | H | H | CSSMe | Me | Me |
| I-143 | H | Cl | H | H | H | CSSMe | Me | Me |
| I-144 | Me | H | H | H | H | CSSMe | Me | Me |
| I-145 | H | Me | H | H | H | CSSMe | Me | Me |
| I-146 | H | H | Me | H | H | CSSMe | Me | Me |
| I-147 | H | Bu | H | H | H | CSSMe | Me | Me |
| I-148 | H | H | Bu | H | H | CSSMe | Me | Me |

TABLE 8

| | R¹ | R² | R³ | R⁴ | R⁵ | R⁶ | R⁷ | R⁸ |
|---|---|---|---|---|---|---|---|---|
| I-149 | Buᵗ | H | H | H | H | CSSMe | Me | Me |
| I-150 | H | H | Et | H | H | CSSMe | Me | Me |
| I-151 | H | Et | H | H | H | CSSMe | Me | Me |
| I-152 | H | H | F | H | H | CSSMe | Me | Me |
| I-153 | H | F | H | H | H | CSSMe | Me | Me |
| I-154 | H | H | Prⁱ | H | H | CSSMe | Me | Me |
| I-155 | H | H | Morpholino | H | H | CSSMe | Me | Me |
| I-156 | H | Ac | H | H | H | CSSMe | Me | Me |
| I-157 | H | H | Br | H | H | CSSMe | Me | Me |
| I-158 | H | Br | H | H | H | CSSMe | Me | Me |
| I-159 | Br | H | H | H | H | CSSMe | Me | Me |
| I-160 | H | C(Me)=NOMe | H | H | H | CSSMe | Me | Me |
| I-161 | H | H | Ac | H | H | CSSMe | Me | Me |
| I-162 | H | H | C(Me)=NOMe | H | H | CSSMe | Me | Me |
| I-163 | OPrⁱ | H | H | H | H | CSSMe | Me | Me |
| I-164 | Pr | H | H | H | H | CSSMe | Me | Me |
| I-165 | CF₃ | H | H | H | H | CSSMe | Me | Me |
| I-166 | H | H | OPh | H | H | CSSMe | Me | Me |
| I-167 | H | H | Pr | H | H | CSSMe | Me | Me |
| I-168 | H | H | Buᵗ | H | H | CSSMe | Me | Me |
| I-169 | H | CF₃ | H | H | H | CSSMe | Me | Me |
| I-170 | H | H | CF₃ | H | H | CSSMe | Me | Me |
| I-171 | Prⁱ | H | NHAc | H | H | CSSMe | Me | Me |
| I-172 | Prⁱ | H | H | H | NHAc | CSSMe | Me | Me |
| I-173 | H | COOMe | H | H | OMe | CSSMe | Me | Me |

TABLE 9

| | R¹ | R² | R³ | R⁴ | R⁵ | R⁶ | R⁷ | R⁸ |
|---|---|---|---|---|---|---|---|---|
| I-174 | Morpholino | H | H | H | H | CSSMe | Me | Me |
| I-175 | H | Morpholino | H | H | H | CSSMe | Me | Me |
| I-176 | Prⁱ | H | H | COOEt | H | CSSMe | Me | Me |
| I-177 | H | H | Piperidino | H | H | CSSMe | Me | Me |
| I-178 | Pyrrolidino | H | H | H | H | CSSMe | Me | Me |
| I-179 | H | SMe | H | H | H | CSSMe | Me | Me |
| I-180 | H | H | SMe | H | H | CSSMe | Me | Me |
| I-181 | OCF₃ | H | H | H | H | CSSMe | Me | Me |
| I-182 | H | OCF₃ | H | H | H | CSSMe | Me | Me |
| I-183 | H | H | OCF₃ | H | H | CSSMe | Me | Me |
| I-184 | H | H | 3-Pyridyl | H | H | CSSMe | Me | Me |
| I-185 | H | 3-Pyridyl | H | H | H | CSSMe | Me | Me |
| I-186 | 3-Pyridyl | H | H | H | H | CSSMe | Me | Me |
| I-187 | OPh | H | H | H | H | CSSMe | Me | Me |
| I-188 | H | OEt | OEt | H | H | COOMe | Me | Me |
| I-189 | OMe | H | H | H | H | COOMe | Me | Me |

TABLE 9-continued

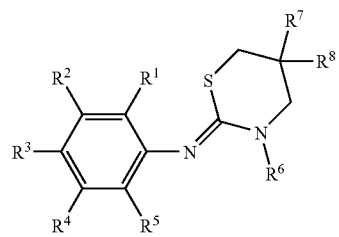

| | R¹ | R² | R³ | R⁴ | R⁵ | R⁶ | R⁷ | R⁸ |
|---|---|---|---|---|---|---|---|---|
| I-190 | H | H | Et | H | H | COOMe | Me | Me |
| I-191 | H | H | Pr$^i$ | H | H | COOMe | Me | Me |
| I-192 | OMe | H | H | H | H | COSMe | Me | Me |
| I-193 | H | H | Et | H | H | COSMe | Me | Me |
| I-194 | H | H | Pr$^i$ | H | H | COSMe | Me | Me |
| I-195 | H | H | OEt | H | H | COSMe | Me | Me |
| I-196 | H | OMe | OEt | H | H | COSMe | Me | Me |
| I-197 | H | Piperidino | H | H | H | CSSMe | Me | Me |
| I-198 | H | H | NEt$_2$ | H | H | CSSMe | Me | Me |

TABLE 10

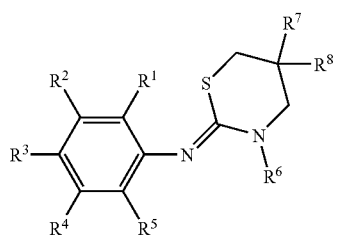

| | R¹ | R² | R³ | R⁴ | R⁵ | R⁶ | R⁷ | R⁸ |
|---|---|---|---|---|---|---|---|---|
| I-199 | OMe | H | COOMe | H | H | CSSMe | Me | Me |
| I-200 | H | 2-Oxopyr-rolidino | H | H | H | CSSMe | Me | Me |
| I-201 | H | OPh | H | H | H | CSSMe | Me | Me |
| I-202 | H | H | Ph | H | H | CSSMe | Me | Me |
| I-203 | Ph | H | H | H | H | CSSMe | Me | Me |
| I-204 | H | Ph | H | H | H | CSSMe | Me | Me |
| I-205 | Pr$^i$ | H | H | H | H | CSOMe | Me | Me |
| I-206 | Pr$^i$ | H | l | H | H | CSSMe | Me | Me |
| I-207 | OMe | H | (Morpho-lino)CO | H | H | CSSMe | Me | Me |
| I-208 | H | H | NMe$_2$ | H | H | CSSMe | Me | Me |
| I-209 | H | NMe$_2$ | H | H | H | CSSMe | Me | Me |
| I-210 | N(Me)Et | H | H | H | H | CSSMe | Me | Me |
| I-211 | N(Me)Pr | H | H | H | H | CSSMe | Me | Me |
| I-212 | NEt$_2$ | H | H | H | H | CSSMe | Me | Me |
| I-213 | F | H | H | H | F | CSSMe | Me | Me |
| I-214 | Pr$^i$ | H | Cl | H | H | CSSMe | Me | Me |
| I-215 | NMe$_2$ | Me | H | H | H | CSSMe | Me | Me |
| I-216 | NMe$_2$ | H | Me | H | H | CSSMe | Me | Me |
| I-217 | NMe$_2$ | H | H | Me | H | CSSMe | Me | Me |
| I-218 | NMe$_2$ | H | H | Cl | H | CSSMe | Me | Me |
| I-219 | Me | H | H | H | Me | CSSMe | Me | Me |
| I-220 | NMe$_2$ | H | H | H | H | CSSEt | Me | Me |
| I-221 | H | NMe$_2$ | H | H | H | CSSEt | Me | Me |
| I-222 | NMe$_2$ | H | Me | H | H | CSSEt | Me | Me |
| I-223 | H | H | Pr$^i$ | H | H | CSSEt | Me | Me |

TABLE 11

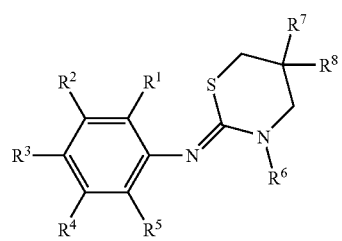

| | R¹ | R² | R³ | R⁴ | R⁵ | R⁶ | R⁷ | R⁸ |
|---|---|---|---|---|---|---|---|---|
| I-224 | OMe | H | CONHMe | H | H | CSSMe | Me | Me |
| I-225 | OCHF$_2$ | H | H | H | H | CSSMe | Me | Me |
| I-226 | H | OCHF$_2$ | H | H | H | CSSMe | Me | Me |
| I-227 | H | NEt$_2$ | H | H | H | CSSMe | Me | Me |
| I-228 | NMe$_2$ | H | Cl | H | H | CSSMe | Me | Me |
| I-229 | NMe$_2$ | H | F | H | H | CSSMe | Me | Me |
| I-230 | NMe$_2$ | H | H | F | H | CSSMe | Me | Me |
| I-231 | NMe$_2$ | H | Et | H | H | CSSMe | Me | Me |
| I-232 | NMe$_2$ | H | H | Et | H | CSSMe | Me | Me |
| I-233 | NMe$_2$ | H | Cl | H | H | CSSEt | Me | Me |
| I-234 | NMe$_2$ | H | F | H | H | CSSEt | Me | Me |
| I-235 | NMe$_2$ | H | Et | H | H | CSSEt | Me | Me |
| I-236 | Pr$^i$ | H | H | H | H | CSSBu$^s$ | Me | Me |
| I-237 | Pr$^i$ | H | H | H | H | CSSBu$^i$ | Me | Me |
| I-238 | Pr$^i$ | H | H | H | H | CSNHMe | Me | Me |
| I-239 | Me | NMe$_2$ | H | H | H | CSSMe | Me | Me |
| I-240 | NMe$_2$ | OMe | H | H | H | CSSMe | Me | Me |
| I-241 | H | NMe$_2$ | Me | H | H | CSSMe | Me | Me |
| I-242 | NMe$_2$ | Cl | H | H | H | CSSMe | Me | Me |
| I-243 | H | NMe$_2$ | OMe | H | H | CSSMe | Me | Me |
| I-244 | Pr$^i$ | H | H | H | H | CSSEt | Et | Et |
| I-245 | Pr$^i$ | H | H | H | H | Me | Me | Me |
| I-246 | Pr$^i$ | H | H | H | H | Pr | Me | Me |
| I-247 | Pr$^i$ | H | H | H | H | Pr$^i$ | Me | Me |
| I-248 | Pr$^i$ | H | H | H | H | Bu$^i$ | Me | Me |

TABLE 12

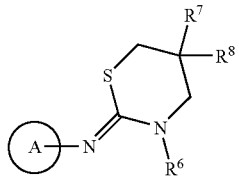

| | A | R⁶ | R⁷ | R⁸ |
|---|---|---|---|---|
| I-249 | 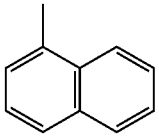 | CSSMe | Me | Me |
| I-250 | 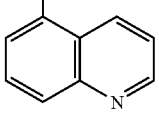 | CSSMe | Me | Me |
| I-251 | 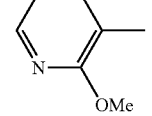 | CSSMe | Me | Me |
| I-252 | 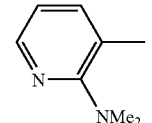 | CSSMe | Me | Me |
| I-253 | 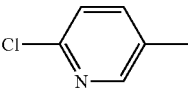 | CSSMe | Me | Me |
| I-254 | 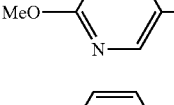 | CSSMe | Me | Me |
| I-255 | 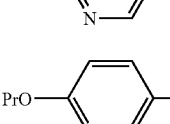 | CSSMe | Me | Me |
| I-256 | 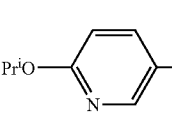 | CSSMe | Me | Me |
| I-257 | 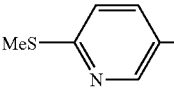 | CSSMe | Me | Me |
| I-258 | 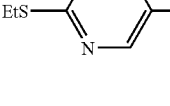 | CSSMe | Me | Me |
| I-259 |  | CSSMe | Me | Me |

TABLE 12-continued

| | A | R⁶ | R⁷ | R⁸ |
|---|---|---|---|---|
| I-260 | 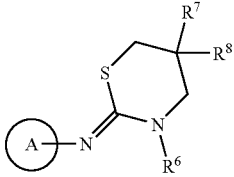 | CSSMe | Me | Me |
| I-261 | 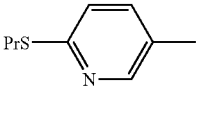 | CSSMe | Me | Me |

TABLE 13

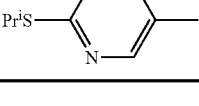

| | R¹ | R² | R³ | R⁴ | R⁵ | R⁶ | R⁷ | R⁸ |
|---|---|---|---|---|---|---|---|---|
| I-262 | NMe₂ | H | OMe | H | H | CSSMe | Me | Me |
| I-263 | NMe₂ | H | H | OMe | H | CSSMe | Me | Me |
| I-264 | Me | NEt₂ | H | H | H | CSSMe | Me | Me |
| I-265 | H | NEt₂ | Me | H | H | CSSMe | Me | Me |
| I-266 | H | NEt₂ | OMe | H | H | CSSMe | Me | Me |
| I-267 | Buˢ | H | H | H | H | CSSMe | Et | Et |
| I-268 | Prⁱ | H | H | H | H | CSSMe | Pr | Pr |
| I-269 | Prⁱ | H | H | H | H | CSSMe | —(CH₂)₄— | |
| I-270 | Prⁱ | H | H | H | H | CSSMe | —(CH₂)₅— | |

TABLE 14

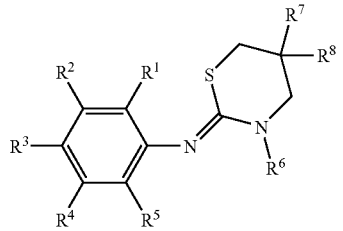

| | R¹ | R² | R³ | R⁴ | R⁵ | R⁶ | R⁷ | R⁸ |
|---|---|---|---|---|---|---|---|---|
| I-271 | Prⁱ | H | H | H | H | SO₂Me | Me | Me |
| I-272 | Prⁱ | H | H | H | H | 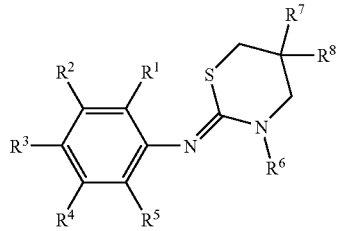 | Me | Me |
| I-273 | Prⁱ | H | H | H | H | SO₂—C₆H₄—Me | Me | Me |

TABLE 14-continued

[Structure: phenyl ring with $R^1, R^2, R^3, R^4, R^5$ substituents connected via N=C to a thiazine ring bearing S, $R^7$, $R^8$, and N-$R^6$]

| | $R^1$ | $R^2$ | $R^3$ | $R^4$ | $R^5$ | $R^6$ | $R^7$ | $R^8$ |
|---|---|---|---|---|---|---|---|---|
| I-274 | H | $Pr^i$ | H | H | H | $SO_2$-C$_6$H$_4$-Me (4-) | Me | Me |
| I-275 | H | $Pr^i$ | H | H | H | $SO_2Et$ | Me | Me |
| I-276 | H | $Pr^i$ | H | H | H | $SO_2$-C$_6$H$_4$-NO$_2$ (4-) | Me | Me |
| I-277 | H | $Pr^i$ | H | H | H | $SO_2$-C$_6$H$_4$-OMe (4-) | Me | Me |
| I-278 | H | $Pr^i$ | H | H | H | $SO_2$-C$_6$H$_4$-NO$_2$ (3-) | Me | Me |
| I-279 | H | $Pr^i$ | H | H | H | $SO_2$-C$_6$H$_4$-CF$_3$ (4-) | Me | Me |
| I-280 | H | $Pr^i$ | H | H | H | $SO_2$-C$_6$H$_4$-NO$_2$ (2-) | Me | Me |

Physical Date (M.p., $^1$H-NMR) of the compounds in the above Tables are shown in the following Tables.

TABLE 15

| Comp. No. | Physical Date | |
|---|---|---|
| | M.p. | NMR |
| I-16 | 57–59° C. | 1.16(6H, s), 1.31(3H, t, J=7.3), 2.64(2H, s), 2.91(2H, q, J=7.3), 3.78(2H, s), 6.96(1H, dd, J=7.4, 1.2), 7.14(1H, t, J=7.4), 7.36(2H, t, J=7.4). |
| I-17 | | 1.15(6H, s), 1.31(3H, t, J=7.3), 2.67(2H, s), 2.91(2H, q J=7.3), 3.77(2H, s), 7.10–7.15(4H, m). |
| I-18 | | 1.16(6H, s), 1.31(3H, t, J=7.3), 2.68(2H, s), 2.92(2H, q, J=7.3), 3.80(2H, s), 6.96(1H, dd, J=7.7, 1.2), 7.08(1H, dt, J=7.7, 1.6), 7.25(2H, t, J=7.4), 7.40(1H, d, J=7.4). |
| I-19 | | 1.15(6H, s), 1.27(3H, t, J=7.3), 2.24(3H, s), 2.62(2H, s), 2.92(2H, q, J=7.4), 3.77(2H, s), 6.83(1H, d, J=7.7), 7.04(1H, t, J=7.7), 7.16–7.22(2H, m). |
| I-20 | | 1.15(6H, s), 1.19(3H, t, J=7.4), 1.31(3H, t, J=7.3), 2.62(2H, q, J=7.3), 2.65(2H, s), 2.94(2H, q, J=7.4), 3.77(2H, s), 6.83(1H, d, J=7.6), 7.10–7.22(3H, m). |
| I-21 | | 0.95(3H, t, J=7.3), 1.15(6H, s), 1.30(3H, t, J=7.4), 1.50–1.64(2H, m), 2.56(2H, q, J=7.3), 2.59(2H, s), 2.90(2H, q, J=7.4), 3.76(2H, s), 6.82(1H, d, J=7.3), 7.06–7.28(3H, m). |
| I-22 | | 0.90(3H, t, J=7.1), 1.15(6H, s), 1.29(3H, t, J=7.4), 1.30–1.34(2H, m), 1.52–1.58(2H, m), 2.54(2H, q, J=7.1), 2.62(2H, s), 2.92(2H, q, J=7.4), 3.76(2H, s), 6.79(1H, dd, J=7.9, 1.4), 7.06–7.28(3H, m). |
| I-23 | | 0.86(3H, t, J=7.4), 1.14(6H, s), 1.16(6H, d, J=6.9), 1.29(3H, t, J=7.4), 1.48–1.58(2H, m), 2.61(2H, s), 2.89(2H, q, J=7.4), 2.88–2.92(1H, m), 3.76(2H, d, J=13.6), 3.82(1H, d, J=13.6), 6.82–6.88(1H, m), 7.10–7.18(1H, m), 7.23–7.29(1H, m). |
| I-24 | | 1.15(6H, s), 1.27(3H, t, J=7.4), 1.33(9H, s), 2.68(2H, s), 2.86(2H, q, J=7.4), 3.75(2H, s), 6.86(1H, dd, J=7.4, 1.6), 7.08–7.19(2H, m), 7.38(2H, dd, J=7.4, 1.6). |
| I-25 | | 0.99(6H, s), 1.25(3H, t, J=7.4), 2.45(2H, s), 2.82(2H, q, J=7.4), 3.51(2H, s), 6.98(1H, d, J=7.7), 7.20–7.36(6H, m), 7.43(2H, m). |
| I-26 | 82–83° C. | 1.15(6H, s), 1.29(3H, t, J=7.3), 2.66(2H, s), 2.89(2H, q, J=7.4), 3.77(2H, s), 6.98(1H, d, J=7.6), 7.19(1H, t, J=7.6), 7.49(1H, t, J=7.6), 7.64(1H, d, J=7.6). |

TABLE 16

| Comp. No. | Physical Date | |
|---|---|---|
| | M.p. | NMR |
| I-27 | | 1.16(6H, s), 1.25(3H, t, J=7.4), 2.62(2H, s), 2.88(2H, q, J=7.4), 3.78(2H, s), 3.83(3H, s), 6.91–6.96(3H, m), 7.05–7.14(1H, m). |
| I-28 | | 1.15(6H, s), 1.30(3H, t, J=7.4), 1.40(3H, t, J=7.0), 2.60(2H, s), 2.90(2H, q, J=7.4), 3.78(2H, s), 4.08(2H, q, J=7.0), 6.90–6.94(3H, m), 7.06–7.08(1H, m). |
| I-29 | | 1.14(6H, s), 1.29(6H, d, J=7.4), 1.31(6H, d, J=6.0), 2.59(2H, s), 2.89(2H, q, J=7.4), 3.76(2H, s), 4.50(1H, q, J=6.0), 6.90–6.93(3H, m), 7.01–7.07(1H, m). |
| I-30 | 78–80° C. | 1.15(6H, s), 1.29(3H, t, J=7.4), 2.43(3H, s), 2.63(2H, s), 2.89(2H, q, J=7.4), 3.78(2H, s), 6.87–6.91(1H, m), 7.05–7.14(2H, m), 7.20–7.29(1H, m). |
| I-31 | 55–57° C. | 1.15(6H, s), 1.29(3H, t, J=7.4), 1.31(3H, t, J=7.4), 2.66(2H, s), 2.89(2H, q, J=7.4), 2.94(2H, q, J=7.4), 3.78(2H, s), 6.91(1H, dd, J=7.4, 1.6), 7.08–7.20(2H, m), 7.32(1H, dd, J=7.4, 1.6). |
| I-32 | | 1.15(6H, s), 1.27(6H, d, J=6.6), 1.28(6H, d, J=7.4), 2.65(2H, s), 2.88(2H, q, J=7.4), 3.38–3.42(1H, m), 3.78(2H, s), 6.90(1H, dd, J=7.7, 1.6), 7.08–7.20(2H, m), 7.32(1H, dd, J=7.7, 1.6). |
| I-33 | | 1.15(6H, s), 1.29(3H, t, J=7.4), 2.60(2H, s), 2.71(6H, s), 2.89(2H, q, J=7.4), 3.77(2H, s), 6.90–6.98(3H, m), 7.05–7.10(1H, m). |

TABLE 16-continued

| Comp. No. | Physical Date | |
|---|---|---|
| No | M.p. | |
| I-34 | | 1.16(6H, s), 1.27(6H, d, J=6.9), 1.31(3H, t, J=7.4), 2.64(2H, s), 2.91(2H, q, J=7.4), 2.98(1H, q, J=6.9), 3.77(2H, s), 6.78–6.83(2H, m), 7.01–7.04(1H, m), 7.25–7.27(1H, m). |
| I-35 | 68–69° C. | 1.16(6H, s), 1.30(3H, t, J=7.3), 2.66(2H, s), 2.90(2H, q, J=7.3), 3.76(2H, s) 6.98(2H, dd, J=6.6, 2.1), 7.31(2H, dd, J=6.6, 2.1). |
| I-36 | 67–69° C. | 1.15(6H, s), 1.20(6H, d, J=6.9), 1.26(3H, t, J=7.4), 2.64(2H, s), 2.86(2H, q, J=7.4), 2.89(1H, q, J=6.9), 3.75(2H, s), 6.98(2H, d, J=8.2), 7.20(2H, d, J=8.3). |
| I-37 | 125–126° C. | 1.15(6H, s), 1.30(3H, t, J=7.3), 2.72(2H, s), 2.92(2H, q, J=7.3), 3.78(2H, s), 7.05(2H, d, J=8.3), 7.31(2H, d, J=8.3). |
| I-38 | 76–78° C. | 1.15(6H, s), 1.30(3H, t, J=7.4), 2.14(3H, s), 2.29(3H, s), 2.63(2H, s), 2.89(2H, q, J=7.4), 3.77(2H, s), 6.70(1H, d, J=7.9), 6.94(1H, d, J=7.9), 7.06(1H, s). |

TABLE 17

| Comp. No. | Physical Date | |
|---|---|---|
| No | M.p. | |
| I-39 | | 1.14(6H, s), 1.29(3H, t, J=7.4), 2.21(3H, s), 2.32(3H, s), 2.65(2H, s), 2.89(2H, q, J=7.4), 3.76(2H, s), 6.73(1H, d, J=7.9), 6.97(1H, d, J=7.9), 7.02(1H, s). |
| I-40 | | 1.15(6H, s), 1.30(3H, t, J=7.4), 2.19(3H, s), 2.31(3H, s), 2.64(2H, s), 2.89(2H, q, J=7.4), 3.77(2H, s), 6.65(1H, s), 6.86(1H, d, J=7.9), 7.07(1H, d, J=7.7). |
| I-41 | 59–61° C. | 1.15(6H, s), 1.30(3H, t, J=7.3), 2.19(6H, s), 2.62(2H, s), 2.90(2H, q, J=7.3), 3.78(2H, s), 6.90–6.96(1H, m), 7.02–7.08(2H, m). |
| I-42 | | 1.15(6H, s), 1.31(3H, t, J=7.4), 2.26(3H, s), 2.28(3H, s), 2.65(2H, s), 2.91(2H, q, J=7.4), 3.78(2H, s), 6.74(1H, dd, J=7.9, 1.8), 6.80(1H, d, J=1.8), 7.13(1H, d, J=7.7). |
| I-43 | | 1.15(6H, s), 1.31(3H, t, J=7.4), 2.31(6H, s), 2.63(2H, s), 2.90(2H, q, J=7.4), 3.76(2H, s), 6.58(2H, s), 6.77(1H, s). |
| I-44 | | 1.15(6H, s), 1.28(3H, t, J=7.4), 2.21(3H, s), 2.64(2H, s), 2.90(2H, q, J=7.4), 3.76(2H, s), 6.74(1H, d, J=8.2), 7.10–7.18(2H, m). |
| I-45 | | 1.15(6H, s), 1.28(3H, t, J=7.4), 2.31(3H, s), 2.66(2H, s), 2.92(2H, q, J=7.4), 3.78(2H, s), 6.74(1H, d, J=7.8), 7.04(1H, d, J=7.8), 7.25(1H, d, J=7.8). |
| I-46 | 119–120° C. | 1.16(6H, s), 1.25(6H, d, J=6.9), 1.29(3H, t, J=7.4), 2.69(2H, s), 2.90(2H, q, J=7.4), 3.15(1H, m), 3.79(2H, s), 6.92(1H, d, J=8.7), 8.01(1H, dd, J=8.5, 2.4), 8.18(1H, d, J=2.4). |
| I-47 | | 1.17(6H, s), 1.23(6H, d, J=6.9), 1.30(3H, t, J=7.4), 2.69(2H, s), 2.91(2H, q, J=7.4), 3.19(1H, m), 3.79(2H, s), 7.41(1H, d, J=8.7), 7.71(1H, d, J=2.4), 7.92(1H, dd, J=8.7, 2.4). |
| I-48 | | 1.15(6H, s), 1.30(3H, t, J=7.4), 2.73(2H, s), 2.93(2H, q, J=7.4), 3.82(2H, s) 7.15(2H, d, J=8.3), 8.48(1H, dd, J=8.3, 1.4), 8.90(1H, d, J=8.3). |

TABLE 17-continued

| Comp. No. | Physical Date | |
|---|---|---|
| No | M.p. | |
| I-49 | 64–66° C. | 0.95(3H, t, J=7.3), 1.15(6H, s), 1.50–1.64(2H, m), 2.32(3H, s), 2.56(2H, q, J=7.3), 2.63(2H, s), 3.78(2H, s), 6.82(1H, d, J=7.3), 7.06–7.28(3H, m). |
| I-50 | 95–96° C. | 1.16(6H, s), 1.20(6H, d, J=6.9), 2.32(3H, s), 2.64(2H, s), 3.12(1H, q, J=6.9), 3.79(2H, s), 6.78–6.82(1H, m), 7.11–7.20(2H, m), 7.30–7.34(1H, m). |

TABLE 18

| Comp. No. | Physical Date | |
|---|---|---|
| No | M.p. | |
| I-51 | 53–56° C. | 0.85(3H, t, J=7.3), 1.15(6H, d, J=6.9), 1.18(6H, s), 1.57–1.70(2H, m), 2.31(3H, s), 2.62(2H, s), 2.91(1H, q, J=6.9), 3.74(1H, d, J=13.7), 3.78(1H, d, J=13.7), 6.78–6.83(1H, m), 7.11–7.18(2H, m), 7.23–7.30(1H, m). |
| I-52 | 88–90° C. | 1.17(6H, s), 1.27(6H, d, J=6.9), 2.33(3H, s), 2.65(2H, s), 2.91(1H, q, J=6.9), 3.79(2H, s), 6.78–6.83(2H, m), 7.01–7.04(1H, m), 7.20–7.24(1H, m). |
| I-53 | | 1.16(6H, s), 2.32(3H, s), 2.65(2H, s), 3.77(2H, s), 3.87(6H, s), 6.51–6.59(2H, m), 6.80–6.89(1H, m). |
| I-54 | 102–104° C. | 1.15(6H, s), 2.31(3H, s), 2.65(2H, s), 3.76(2H, s), 5.96(1H, s), 6.42(1H, dd, J=8.1, 1.8), 6.53(1H, d, J=1.8), 6.78(1H, d, J=8.1). |
| I-55 | 129–131° C. | 1.16(6H, s), 2.32(3H, s), 2.67(2H, s), 3.78(2H, s), 3.85(6H, s), 3.86(3H, s), 6.20(2H, s) |
| I-56 | 107–109° C. | 1.17(3H, t, J=7.6), 1.22(6H, s), 2.58(2H, q, J=7.6), 2.64(3H, s), 2.66(2H, s), 4.51(2H, s), 6.91(1H, dd, J=7.5, 1.3), 7.02–7.19(2H, m), 7.23–7.28(1H, m). |
| I-57 | | 0.85(3H, t, J=7.3), 1.18(6H, d, J=6.9), 1.23(6H, s), 1.57–1.70(2H, m), 2.64(3H, s), 2.66(2H, s), 2.88(1H, q, J=6.9), 4.38(1H, d, J=13.7), 4.60(1H, d, J=13.7), 6.83–6.90(1H, m), 7.11–7.18(2H, m), 7.28–7.35(1H, m). |
| I-58 | 85–87° C. | 1.22(6H, s), 2.62(3H, s), 2.63(2H, s), 3.35(3H, s), 4.40(2H, s), 4.48(2H, s), 6.93–6.99(1H, m), 7.11–7.29(2H, m), 7.40–7.49(1H, m). |
| I-59 | 113–114° C. | 1.22(3H, s), 1.24(3H, s), 1.37(3H, d, J=6.4), 2.63(3H, s), 2.65(2H, s), 3.24(3H, s), 4.35(1H, d, J=13.6), 4.55(1H, q, J=6.4), 4.66(1H, d, J=13.6), 6.91(1H, d, J=7.4), 7.19–7.40(2H, m), 7.51(1H, d, J=7.4). |
| I-60 | 128–130° C. | 1.22(6H, s), 2.62(3H, s), 2.65(2H, s), 3.85(3H, s), 4.53(2H, s), 6.93–6.99(2H, m), 7.02–7.15(2H, m). |
| I-61 | 100–101° C. | 1.26(6H, s), 1.43(3H, t, J=7.4), 2.66(2H, s), 2.67(3H, s), 4.08(2H, q, J=7.0), 4.55(2H, s), 6.95–6.99(3H, m), 7.11–7.18(1H, m). |
| I-62 | 137–139° C. | 1.23(6H, s), 2.43(3H, s), 2.64(3H, s), 2.67(2H, s), 4.53(2H, s), 6.87–6.92(1H, m), 7.11–7.20(2H, m), 7.23–7.29(1H, m). |

TABLE 19

| Comp. No. | Physical Date | |
|---|---|---|
| No | M.p. | |
| I-63 | 103–105° C. | 1.15(6H, s), 1.29(3H, t, J=7.4), 1.31(3H, t, J=7.4), 2.66(2H, s), 2.89(2H, q, J=7.4), 2.94(2H, q, J=7.4), 3.78(2H, s), 6.91(1H, dd, J=7.4, 1.6), 7.08–7.20(2H, m), 7.32(1H, dd, J=7.4, 1.6). |
| I-64 | 125–126° C. | 1.24(6H, s), 1.28(6H, d, J=6.6), 2.63(3H, s), 2.66(2H, s), 3.38–3.42(1H, m), 4.53(2H, s), 6.97(1H, dd, J=7.7, 1.6), 7.08–7.20(2H, m), 7.32(1H, dd, J=7.7, 1.6). |
| I-65 | | 1.22(6H, s), 2.63(3H, s), 2.65(2H, d, J=13.6), 2.75(3H, s), 4.17(1H, d, J=13.6), 4.77(1H, d, J=13.6), 7.06(1H, dd, J=7.7, 1.7), 7.19–7.40(2H, m), 7.97(1H, dd, J=7.7, 1.7). |
| I-66 | 147–149° C. | 1.23(6H, s), 2.63(3H, s), 2.71(2H, s), 3.13(3H, s), 4.52(2H, s), 7.11(1H, m,), 7.11–7.20(2H, m), 7.23–7.29(1H, m). |
| I-67 | 129–130° C. | 1.22(6H, s), 1.23(3H, t, J=6.9), 2.63(3H, s), 2.66(2H, s), 2.70–2.85(1H, m), 2.90–3.15(1H, m), 4.25(1H, d, J=13.6), 4.70(1H, d, J=13.6), 7.06(1H, d, J=7.5), 7.30–7.45(2H, m), 7.90(1H, d, J=7.5). |
| I-68 | 100–102° C. | 1.23(6H, s), 2.62(3H, s), 2.65(2H, s), 2.71(6H, s), 4.50(2H, s), 6.93–6.99(3H, m), 7.02–7.15(1H, m). |
| I-69 | | 1.23(6H, s), 1.25(6H, d, J=6.9), 2.64(3H, s), 2.66(2H, s), 2.92(1H, q, J=6.9), 4.52(2H, s), 6.84–6.86(2H, m), 7.08–7.13(1H, m), 7.28–7.32(1H, m). |
| I-70 | 116–118° C. | 1.23(6H, s), 2.64(3H, s), 2.68(2H, s), 4.51(2H, s), 6.97(2H, d, J=8.6), 7.35(2H, d, J=8.6). |
| I-71 | 103–105° C. | 1.22(6H, s), 2.19(3H, s), 2.30(3H, s), 2.63(3H, s), 2.65(2H, s), 4.50(2H, s), 6.79(1H, d, J=7.9), 6.98(1H, d, J=7.9), 7.02(1H, s). |
| I-72 | 100–101° C. | 1.23(6H, s), 2.18(3H, s), 2.32(3H, s), 2.64(3H, s), 2.65(2H, s), 4.51(2H, s), 6.71(1H, s), 6.88(1H, d, J=7.9), 7.08(1H, t, J=7.9). |
| I-73 | 93–95° C. | 1.22(6H, s), 2.12(3H, s), 2.30(3H, s), 2.64(3H, s), 2.65(2H, s), 4.51(2H, s), 6.76(1H, d, J=7.9), 6.98(1H, d, J=7.9), 7.08(1H, t, J=7.9). |
| I-74 | 126–128° C. | 1.23(6H, s), 2.25(3H, s), 2.27(3H, s), 2.64(3H, s), 2.65(2H, s), 4.51(2H, s), 6.76(1H, d, J=7.9), 6.82(1H, s), 713(1H, d, J=7.9). |
| I-75 | 96–98° C. | 1.23(6H, s), 2.32(6H, s), 2.63(3H, s), 2.65(2H, s), 4.51(2H, s), 6.64(2H, s), 6.80(1H, s). |
| I-76 | | 1.22(6H, s), 2.64(3H, s), 2.65(2H, s), 3.79(3H, s), 3.88(3H, s), 4.52(2H, s), 6.60(1H, d, J=7.9), 6.73(1H, d, J=7.9), 7.04(1H, d, J=7.9). |

TABLE 20

| Comp. No. | Physical Date | |
|---|---|---|
| No | M.p. | |
| I-77 | | 1.24(6H, s), 2.63(3H, s), 2.68(2H, s), 3.87(6H, s), 4.50(2H, s), 6.61–6.65(2H, m), 6.85–6.89(1H, m). |
| I-78 | | 1.22(6H, s), 2.62(3H, s), 2.66(2H, s), 3.81(6H, s), 4.52(2H, s), 6.48(1H, dd, J=8.5, 2.4), 6.51(1H, d, J=2.4), 6.92(1H, d, J=8.5). |
| I-79 | | 1.22(6H, s), 2.62(3H, s), 2.64(2H, s), 3.77(6H, s), 4.52(2H, s), 6.56(1H, d, J=2.4), 6.68(1H, dd, J=8.5, 2.4), 686(1H, d, J=8.5). |
| I-80 | 108–110° C. | 1.23(6H, s), 2.63(3H, s), 2.66(2H, s), 4.49(2H, s), 6.04(2H, s), 6.50(1H, dd, J=8.1, 1.8), 6.61(1H, d, J=1.8), 6.83(1H, d, J=8.1). |
| I-81 | | 1.23(6H, s), 1.25(6H, d, J=6.9), 2.65(3H, s), 2.71(2H, s), 3.11(1H, q, J=6.9), 4.51(2H, s), 7.02(1H, d, J=8.5), 8.04(1H, dd, J=8.5, 2.7), 8.21(1H, d, J=2.7). |
| I-82 | | 1.21(6H, s), 1.24(6H, d, J=6.9), 2.63(3H, s), 2.66(2H, s), 3.17(1H, q, J=6.9), 4.51(2H, s), 7.45(1H, d, J=8.5), 7.80(1H, d, J=2.4), 7.99(1H, dd, J=8.5, 2.4). |
| I-83 | | 1.24(6H, s), 2.64(3H, s), 2.68(2H, s), 3.85(6H, s), 3.86(3H, s), 4.51(2H, s), 6.28(2H, s). |
| I-84 | 68–70° C. | 1.22(6H, d, J=6.9), 1.23(6H, s), 1.35(3H, t, J=7.4), 2.65(2H, s), 3.11(1H, q, J=6.9), 3.25(2H, q, J=6.9), 4.48(2H, s), 6.89–6.92(1H, m), 7.14–7.20(2H, m), 7.30–7.34(1H, m). |
| I-85 | | 0.85(3H, t, J=7.4), 1.18(6H, d, J=6.9), 1.23(6H, s), 1.35(3H, t, J=7.4), 1.57–1.70(2H, m), 2.56(2H, s), 2.87(1H, q, J=6.9), 3.25(2H, q, J=7.4), 4.35(1H, d, J=13.7), 4.60(1H, d, J=13.7), 6.89–6.92(1H, m), 7.10–7.18(2H, m), 7.30–7.34(1H, m). |
| I-86 | 96–97° C. | 1.23(6H, s), 1.36(3H, t, J=7.0), 1.40(3H, t, J=7.0), 2.63(2H, s), 3.27(2H, q, J=7.4), 4.06(2H, q, J=7.0), 4.51(2H, s), 6.92–7.08(3H, m), 7.11–7.15(1H, m). |
| I-87 | 105–106° C. | 1.22(6H, s), 1.35(3H, t, J=7.4), 2.43(3H, s), 2.66(2H, s), 3.26(2H, q, J=7.4), 4.50(2H, s), 6.95–6.98(1H, m), 7.10–7.17(2H, m), 7.24–7.29(1H, m). |

TABLE 21

| Comp. No. | Physical Date | |
|---|---|---|
| No | M.p. | |
| I-88 | | 1.23(6H, s), 1.25(6H, d, J=6.9), 1.35(3H, t, J=7.4), 2.66(2H, s), 2.90(1H, q, J=6.9), 3.28(2H, q, J=7.4), 4.50(2H, s), 6.84–6.88(2H, m), 7.08–7.13(1H, m), 7.28–7.32(1H, m). |
| I-89 | | 0.98(3H, t, J=7.4), 1.12(6H, s), 1.22(6H, d, J=6.9), 1.72–1.80(2H, m), 2.58(2H, s), 2.90(2H, t, J=7.4), 3.06(1H, q, J=6.9), 3.71(2H, s), 6.71–6.76(1H, m), 7.11–7.20(2H, m), 7.30–7.34(1H, m). |
| I-90 | 99–101° C. | 1.14(6H, s), 1.21(6H, d, J=6.9), 2.58(2H, s), 3.14(1H, q, J=6.9), 3.64(2H, s), 3.86(3H, s), 6.73–6.78(1H, m), 7.11–7.18(2H, m), 7.28–7.35(1H, m). |

TABLE 21-continued

| Comp. No. | Physical Date | |
|---|---|---|
| No | M.p. | |
| I-91 | | 1.00(3H, t, J=7.3), 1.14(6H, s), 1.20(6H, d, J=6.9), 1.74(2H, q, J=7.3), 2.58(2H, s), 3.16(1H, q, J=6.9), 3.65(2H, s), 4.23(2H, q, J=6.9), 6.73–6.80(1H, m), 7.12–7.18(2H, m), 7.31–7.34(1H, m). |
| I-92 | 52–53° C. | 1.13(6H, s), 1.19(6H, d, J=6.9), 1.20(3H, t, J=7.4), 2.60(2H, s), 2.98(1H, q, J=6.9), 3.38(2H, q, J=7.4), 3.77(2H, s), 6.73–6.78(1H, m), 7.09–7.18(2H, m), 7.28–7.32(1H, m). |
| I-93 | 76–78° C. | 1.14(6H, s), 1.22(6H, d, J=6.9), 2.62(2H, s), 2.96(1H, q, J=6.9), 3.48(3H, s), 3.75(2H, s), 4.64(2H, s), 6.73–6.78(1H, m), 7.10–7.17(2H, m), 7.25–7.32(1H, m). |
| I-94 | 61–62° C. | 1.14(6H, s), 1.20(6H, d, J=6.9), 2.23(3H, s), 2.68(2H, s), 2.93(1H, q, J=6.9), 3.71(2H, s), 3.94(2H, s), 6.82–6.86(1H, m), 7.10–7.18(2H, m), 7.30–7.36(1H, m). |
| I-95 | 50–52° C. | 1.13(6H, s), 1.20(6H, d, J=6.9), 1.31(3H, t, J=7.3), 2.65(2H, J=7.3), 2.68(2H, s), 2.90(1H, q, J=6.9), 3.71(2H, s), 3.97(2H, s), 6.82–6.86(1H, m), 7.12–7.19(2H, m), 7.30–7.36(1H, m). |
| I-96 | 73–75° C. | 1.21(6H, s), 1.22(6H, d, J=6.9), 1.42(3H, t, J=6.9), 2.61(2H, s), 3.10(1H, q, J=6.9), 4.15(2H, s), 4.65(2H, q, J=6.9), 6.74–6.78(1H, m), 7.14–7.20(2H, m), 7.30–7.34(1H, m). |
| I-97 | 160–162° C. | 1.18(6H, s), 1.22(6H, d, J=6.9), 1.25(3H, t, J=7.4), 2.60(2H, s), 2.90(1H, q, J=6.9), 3.71(2H, q, J=7.4), 4.40(2H, s), 6.74–6.78(1H, m), 7.14–7.20(2H, m), 7.30–7.34(1H, m). |
| I-98 | | 1.04(3H, t, J=7.4), 1.20(6H, d, J=6.9), 1.27(6H, s), 1.73(2H, m), 2.64(2H, s), 3.12(1H, q, J=6.9), 3.22(2H, t, J=7.4), 4.48(2H, s), 6.89–6.92(1H, m), 7.10–7.20(2H, m), 7.28–7.35(1H, m). |

TABLE 22

| Comp. No. | Physical Date | |
|---|---|---|
| No | M.p. | |
| I-99 | 113–114° C. | 1.04(6H, d, J=6.9), 1.27(6H, s), 1.42(3H, d, J=6.9), 2.63(2H, s), 3.14(1H, q, J=6.9), 4.02(1H, q, J=6.9), 4.46(2H, s), 6.89–6.93(1H, m), 7.10–7.20(2H, m), 7.28–7.35(1H, m). |
| I-100 | | 1.10(6H, d, J=6.9), 1.22(6H, s), 2.64(2H, s), 3.08(1H, q, J=6.9), 4.48(2H, s), 4.49(2H, s), 6.83–6.90(1H, m), 7.11–7.18(2H, m), 7.20–7.38(6H, m). |
| I-101 | | 1.15(6H, s), 1.25(3H, t, J=7.4), 2.70(2H, s), 2.87(2H, q, J=7.4), 3.69(2H, s), 4.55(2H, s), 7.30–7.40(4H, m). |
| I-102 | | 1.24(6H, s), 2.57(3H, s), 2.73(2H, s), 4.43(2H, s), 4.58(2H, s), 7.23–7.40(4H, m). |

TABLE 22-continued

| Comp. No. | Physical Date | |
|---|---|---|
| No | M.p. | |
| I-103 | | 1.11(6H, s), 1.26(3H, t, J=7.4), 2.61(2H, s), 2.83(2H, q, J=7.4), 3.10(2H, t, J=7.4), 3.65(2H, s), 3.66(2H, t, J=7.4), 7.17(1H, dd, J=8.2, 2.1), 7.30(1H, t, J=8.2), 7.36(1H, d, J=2.1). |
| I-104 | | 1.16(6H, s), 2.55(3H, s), 2.63(2H, s), 3.13(2H, t, J=7.5), 3.69(2H, t, J=7.5), 4.35(2H, s), 7.15(1H, dd, J=8.2, 2.1), 7.25(1H, t, J=8.2), 7.36(1H, d, J=2.1). |
| I-105 | | 1.20(6H, d, J=6.9), 1.30(3H, t, J=7.4), 2.10–2.22(2H, m), 2.88(2H, t, J=6.4), 2.94(2H, q, J=7.4), 3.11(1H, q, J=6.9), 4.05(2H, t, J=7.4), 6.82–6.86(1H, m), 7.10–7.16(2H, m), 7.28–7.34(1H, m). |
| I-106 | | 1.17–1.30(12H, m), 1.45–1.52(1H, m), 1.90–1.96(1H, m), 2.92(2H, q, J=7.4), 2.95–3.05(2H, m), 3.14–3.23(1H, m), 3.72–3.75(1H, m), 7.20–7.30(2H, m), 7.40–7.45(2H, m). |
| I-107 | | 1.22(6H, d, J=6.9), 1.28(3H, d, J=6.6), 1.29(3H, t, J=7.4), 1.75–1.77(1H, m), 2.29–2.34(1H, m), 2.88(2H, q, J=7.4), 3.14(1H, m), 3.31–3.36(1H, m), 4.01–4.10(2H, m), 6.81–6.85(1H, m), 7.10–7.20(2H, m), 7.28–7.35(1H, m). |
| I-108 | | 1.12(3H, d, J=6.6), 1.20(6H, d, J=6.9), 1.29(3H, t, J=7.4), 2.40–2.50(1H, m), 2.57(1H, dd, J=13.5, 6.6), 2.91(2H, q, J=7.4), 2.95(1H, m), 3.14(1H, m), 3.45(1H, dd, J=13.5, 8.4), 4.30(1H, dd, J=13.5, 8.4), 6.81–6.85(1H, m), 7.10–7.20(2H, m), 7.28–7.35(1H, m). |

TABLE 23

| Comp. No. | Physical Date | |
|---|---|---|
| No | M.p. | |
| I-109 | | 0.88(6H, t, J=7.5), 1.22(6H, d, J=6.9), 1.29(3H, t, J=7.4), 1.45–1.52(4H, m), 2.58(2H, s), 2.89(2H, q, J=7.4), 3.15(1H, m), 3.77(2H, s), 6.78–6.83(1H, m), 7.08–7.21(2H, m), 7.30–7.35(1H, m). |
| I-110 | 109–111° C. | 1.21(6H, d, J=6.9), 1.23(6H, s), 1.25(3H, t, J=7.4), 2.81(2H, q, J=7.4), 2.90(1H, t, J=6.9), 3.05(2H, s), 7.13–7.30(2H, m), 7.36–7.45(2H, m). |
| I-111 | | 1.21(6H, d, J=6.9), 1.31(3H, t, J=7.4), 1.42(3H, d, J=6.7), 2.90(2H, q, J=7.4), 3.23(1H, q, J=6.9), 3.69(1H, q, J=6.6), 3.87–3.93(1H, m), 6.78–6.82(1H, m), 7.08–7.20(2H, m), 7.25–7.30(1H, m). |
| I-112 | | 1.19–1.25(9H, m), 1.14(3H, d, J=6.3), 2.76(1H, d, J=10.9), 2.96(2H, q, J=7.4), 3.22(1H, q, J=6.9), 3.44–3.48(1H, m), 5.12(1H, q, J=6.3), 6.81–6.85(1H, m), 7.09–7.16(2H, m), 7.28–7.32(1H, m). |

TABLE 23-continued

| Comp. No | M.p. | Physical Date |
|---|---|---|
| I-113 | 126–128° C. | 1.18(6H, d, J=6.9), 1.22(6H, d, J=6.9), 1.45(3H, t, J=7.4), 1.80–1.91(1H, m), 2.57–2.64(2H, m), 2.61(3H, s), 2.86–2.89(1H, m), 3.07(1H, m), 5.95–6.05(1H, m), 6.98–7.00(1H, m), 7.12–7.22(2H, m), 7.28–7.35(1H, m). |
| I-114 | | 1.20(6H, d, J=6.9), 1.28(3H, d, J=6.9), 1.82–1.88(1H, m), 2.48–2.63(1H, m), 2.63(3H, s), 3.11(1H, m), 3.29–3.35(1H, m), 4.26(1H, m), 4.98(1H, m), 6.90–6.95(1H, m), 7.15–7.20(2H, m), 7.30–7.35(1H, m). |
| I-115 | | 1.14(3H, d, J=6.5), 1.20(6H, d, J=6.9), 2.53(1H, dd, J=13.0, 5.4), 2.75(3H, s), 2.80–2.85(1H, m), 2.95(1H, dd, J=13.0, 5.4), 3.11(1H, m), 3.72(1H, dd, J=13.0, 9.0), 5.15(1H, dd, J=13.0, 9.0), 6.90–6.95(1H, m), 7.15–7.25(2H, m), 7.30–7.35(1H, m). |
| I-116 | 119–121° C. | 0.88(6H, t, J=7.5), 1.20(6H, d, J=6.9), 1.45–1.52(4H, m), 2.62(2H, s), 2.64(3H, s), 3.15(1H, m), 4.66(2H, s), 6.78–6.83(1H, m), 7.08–7.21(2H, m), 7.30–7.35(1H, m). |
| I-117 | 99–100° C. | 0.71–0.79(1H, m), 0.85–0.90(2H, m), 1.22(6H, d, J=6.9), 1.22–1.25(1H, m), 2.61(3H, s), 2.79(3H, s), 3.00–3.05(1H, m), 4.40(2H, s), 6.92–6.95(1H, m), 7.15–7.21(2H, m), 7.30–7.35(1H, m). |

TABLE 24

| Comp. No | M.p. | Physical Date |
|---|---|---|
| I-118 | | 1.23(6H, s), 1.45(6H, t, J=7.4), 2.63(3H, s), 2.67(2H, s), 4.08(2H, q, J=7.0), 4.55(2H, s), 6.57–6.63(2H, m), 6.85(1H, d, J=7.9). |
| I-119 | 116–118° C. | 1.24(6H, s), 2.37(3H, s), 2.64(3H, s), 2.66(2H, s), 3.84(3H, s), 4.54(2H, s), 6.75–6.80(2H, m), 6.88(1H, m). |
| I-120 | 92–93° C. | 1.23(6H, s), 2.27(3H, s), 2.63(3H, s), 2.67(2H, s), 3.84(3H, s), 4.51(2H, s), 6.51–6.58(2H, m), 7.10(1H, d, J=7.9). |
| I-121 | 129–130° C. | 1.22(6H, s), 2.30(3H, s), 2.63(3H, s), 2.65(2H, s), 3.80(3H, s), 4.53(2H, s), 6.78–6.95(3H, m). |
| I-122 | 93–95° C. | 1.22(6H, s), 2.12(3H, s), 2.30(3H, s), 2.64(3H, s), 2.65(2H, s), 4.51(2H, s), 6.76(1H, d, J=7.9), 6.98(1H, d, J=7.9), 7.08(1H, t, J=7.9). |
| I-123 | 151–152° C. | 1.22(6H, s), 1.83(3H, s), 2.63(3H, s), 2.65(2H, s), 3.17(1H, d, J=13.6), 4.40(1H, d, J=13.6), 4.65(1H, d, J=13.6), 7.01(1H, d, J=7.9), 7.10–7.15(2H, m), 7.30–7.35(1H, m). |

TABLE 25

| Comp. No | M.p. | NMR(CHCl$_3$) |
|---|---|---|
| I-124 | 105–106° C. | 1.23(6H, s), 1.41(3H, t, J=7.0), 2.63(3H, s), 2.66(2H, s), 4.08(2H, q, J=7.0), 4.50(2H, s), 6.88(2H, d, J=8.6), 6.98(2H, d, J=8.6). |
| I-125 | 92–94° C. | 1.23(6H, s), 1.40(3H, t, J=7.0), 2.62(3H, s), 2.66(2H, s), 4.08(2H, q, J=7.0), 4.50(2H, s), 6.57–6.63(2H, m), 6.70–6.75(1H, m), 7.25–7.30(1H, m). |
| I-126 | 108–109° C. | 1.23(6H, s), 2.63(3H, s), 2.65(2H, s), 3.81(3H, s), 4.50(2H, s), 6.92(2H, d, J=8.6), 7.04(2H, d, J=8.6). |
| I-127 | 62–64° C. | 1.23(6H, s), 2.63(3H, s), 2.66(2H, s), 3.82(3H, s), 4.50(2H, s), 6.57–6.63(2H, m), 6.70–6.75(1H, m), 7.25–7.30(1H, m). |
| I-128 | 78–79° C. | 1.23(6H, s), 1.44(3H, t, J=7.0), 2.59(3H, s), 2.63(2H, s), 3.82(3H, s), 4.10(2H, q, J=7.0), 4.47(2H, s), 6.57–6.63(2H, m), 6.82–6.87(1H, m). |
| I-129 | 58–60° C. | 1.04(3H, t, J=7.0), 1.23(6H, s), 2.00(2H, sext, J=7.0), 2.63(3H, s), 2.67(2H, s), 3.87(3H, s), 4.10(2H, t, J=7.0), 4.50(2H, s), 6.58–6.64(2H, m), 6.86–6.91(1H, m). |
| I-130 | | 1.13(6H, s), 1.45(6H, t, J=7.4), 2.28(3H, s), 2.62(2H, s), 3.74(2H, s), 4.08(4H, q, J=7.4), 6.46–6.53(2H, m), 6.88–6.92(1H, m). |
| I-131 | 91–93° C. | 1.04(3H, t, J=7.0), 1.22(6H, s), 1.76(2H, sext, J=7.0), 2.63(3H, s), 2.65(2H, s), 3.91(2H, t, J=7.0), 4.50(2H, s), 6.90(2H, d, J=8.6), 6.98(2H, d, J=8.6). |
| I-132 | 103–104° C. | 1.04(3H, t, J=7.0), 1.22(6H, s), 1.76(2H, sext, J=7.0), 2.63(3H, s), 2.65(2H, s), 3.91(2H, t, J=7.0), 4.50(2H, s), 6.50(1H, d, J=2.1), 6.60(1H, d, J=7.4), 6.72(1H, dd, J=7.4, 2.1), 7.28(1H, d, J=7.4). |
| I-133 | 91–92° C. | 0.98(3H, t, J=7.0), 1.23(6H, s), 1.42–1.48(2H, m), 1.70–1.80(2H, m), 2.63(3H, s), 2.65(2H, s), 3.96(2H, t, J=7.0), 4.50(2H, s), 6.90(2H, d, J=8.6), 6.98(2H, d, J=8.6). |
| I-134 | 86–87° C. | 0.98(3H, t, J=7.0), 1.23(6H, s), 1.42–1.48(2H, m), 1.70–1.80(2H, m), 2.63(3H, s), 2.65(2H, s), 3.96(2H, t, J=7.0), 4.50(2H, s), 6.50(1H, d, J=2.1), 6.60(1H, d, J=7.8), 6.72(1H, dd, J=7.8, 2.1), 7.28(1H, d, J=7.8). |

TABLE 26

| Comp. No | M.p. | NMR(CHCl$_3$) |
|---|---|---|
| I-135 | 69–70° C. | 1.22(6H, s), 1.47(3H, t, J=7.0), 2.64(3H, s), 2.66(2H, s), 3.88(3H, s), 4.15(2H, q, J=7.0), 4.51(2H, s), 6.61(1H, d, J=8.2), 6.62(1H, d, J=2.1), 6.88(1H, d, J=8.2). |
| I-136 | 88–89° C. | 1.04(3H, t, J=7.0), 1.23(6H, s), 1.80(2H, sext, J=7.0), 2.63(3H, s), 2.67(2H, s), 3.87(3H, s), 3.90(2H, t, J=7.0), 4.51(2H, s), 6.61(1H, dd, J=8.2, 2.1), 6.62(1H, d, J=2.1), 6.88(1H, d, J=8.2). |

TABLE 26-continued

| Comp. No. | Physical Date | |
|---|---|---|
| No | M.p. | NMR(CHCl$_3$) |
| I-137 | 83–85° C. | 0.98(3H, t, J=7.0), 1.23(6H, s), 1.42–1.48(2H, m), 1.70–1.80(2H, m), 2.64(3H, s), 2.68(2H, s), 3.87(3H, s), 4.03(2H, t, J=7.0), 4.50(2H, s), 6.59(1H, d, J=8.2), 6.61(1H, s), 6.88(1H, d, J=8.2). |
| I-138 | 84–85° C. | 1.23(6H, s), 1.34(6H, d, J=6.1), 2.63(3H, s), 2.65(2H, s), 4.50(2H, s), 4.53(1H, sept, J=6.1), 6.89(2H, d, J=8.6), 7.04(2H, d, J=8.6). |
| I-139 | 92–93° C. | 1.23(6H, s), 1.34(6H, d, J=6.1), 2.63(3H, s), 2.65(2H, s), 4.50(2H, s), 4.53(1H, sept, J=6.1), 6.50(1H, d, J=2.1), 6.60(1H, d, J=8.0), 6.72(1H, dd, J=8.0, 2.1), 7.28(1H, d, J=8.0). |
| I-140 | 109–110° C. | 1.22(6H, s), 2.63(3H, s), 2.65(2H, s), 4.50(2H, s), 7.04(2H, d, J=7.5), 7.15(1H, d, J=7.5), 7.32(2H, t, J=7.5). |
| I-141 | 92–93° C. | 1.23(6H, s), 2.63(3H, s), 2.69(2H, s), 4.54(2H, s), 7.01–7.08(1H, m), 7.11–7.15(3H, m). |
| I-142 | 133–135° C. | 1.23(6H, s), 2.63(3H, s), 2.69(2H, s), 4.54(2H, s), 7.03(1H, dd, J=8.0, 2.1), 7.08(1H, dd, J=8.0, 2.1), 7.25(1H, t, J=8.0), 7.44(1H, t, J=8.0). |
| I-143 | 92–93° C. | 1.23(6H, s), 2.63(3H, s), 2.67(2H, s), 4.50(2H, s), 6.88(1H, dd, J=8.0, 2.1), 7.03(1H, d, J=2.1), 7.15(1H, dd, J=8.0, 2.1), 7.28(1H, t, J=8.0). |
| I-144 | 134–135° C. | 1.22(6H, s), 2.22(3H, s), 2.63(3H, s), 2.65(2H, s), 4.50(2H, s), 7.00(1H, d, J=8.1), 7.08(1H, t, J=8.1), 7.15–7.25(2H, m). |
| I-145 | 87–89° C. | 1.23(6H, s), 2.37(3H, s), 2.63(3H, s), 2.66(2H, s), 4.50(2H, s), 6.82(1H, d, J=8.1), 6.84(1H, s), 6.98(1H, d, J=8.1), 7.21(1H, t, J=8.1). |

TABLE 27

| Comp. No. | Physical Date | |
|---|---|---|
| No | M.p. | NMR(CHCl$_3$) |
| I-146 | 91–93° C. | 1.23(6H, s), 2.35(3H, s), 2.63(3H, s), 2.65(2H, s), 4.50(2H, s), 6.92(2H, d, J=8.6), 7.15(2H, d, J=8.6). |
| I-147 | 82–83° C. | 0.90(3H, t, J=7.0), 1.22(6H, s), 1.28–1.40(2H, m), 1.48–1.55(2H, m), 2.55(2H, t, J=7.0), 2.64(3H, s), 2.66(2H, s), 4.50(2H, s), 6.90(1H, d, J=7.8), 7.09(1H, t, J=7.8), 7.11(1H, t, J=7.8), 7.28(1H, d, J=7.8). |
| I-148 | 72–73° C. | 0.90(3H, t, J=7.0), 1.22(6H, s), 1.28–1.40(2H, m), 1.48–1.55(2H, m), 2.60(2H, t, J=7.0), 2.64(3H, s), 2.66(2H, s), 4.50(2H, s), 6.95(2H, d, J=8.6), 7.18(2H, d, J=8.6). |
| I-149 | 133–134° C. | 1.23(6H, s), 1.35(9H, s), 2.65(3H, s), 2.69(2H, s), 4.50(2H, s), 6.97(1H, d, J=7.8), 7.13(1H, t, J=7.8), 7.19(1H, t, J=7.8), 7.41(1H, d, J=7.8). |
| I-150 | 99–100° C. | 1.22(6H, s), 1.23(3H, t, J=7.4), 2.62(3H, s), 2.64(2H, s), 2.66(2H, q, J=7.4), 4.50(2H, s), 6.95(2H, d, J=8.6), 7.20(2H, d, J=8.6). |

TABLE 27-continued

| Comp. No. | Physical Date | |
|---|---|---|
| No | M.p. | NMR(CHCl$_3$) |
| I-151 | 40–42° C. | 1.23(6H, s), 1.24(3H, t, J=7.0), 2.64(3H, s), 2.66(2H, s), 2.67(2H, q, J=7.0), 4.52(2H, s), 6.83(1H, d, J=8.1), 6.86(1H, s), 7.00(1H, d, J=8.1), 7.28(1H, t, J=8.1). |
| I-152 | 118–119° C. | 1.23(6H, s), 2.64(3H, s), 2.67(2H, s), 4.52(2H, s), 6.97–7.10(4H, m). |
| I-153 | 89–90° C. | 1.23(6H, s), 2.64(3H, s), 2.67(2H, s), 4.52(2H, s), 6.73–6.90(3H, m), 7.25–7.30(1H, m). |
| I-154 | 111–112° C. | 1.22(6H, s), 1.25(6H, d, J=7.0), 2.62(3H, s), 2.64(2H, s), 2.91(1H, sept, J=7.0), 4.50(2H, s), 6.95(2H, d, J=8.6), 7.25(2H, d, J=8.6). |
| I-155 | 127–129° C. | 1.23(6H, s), 2.62(3H, s), 2.64(3H, s), 3.14–3.18(4H, m), 3.85–3.90(4H, m), 4.50(2H, s), 6.93(2H, d, J=8.6), 7.04(2H, d, J=8.6). |
| I-156 | 91–93° C. | 1.24(6H, s), 2.62(3H, s), 2.65(3H, s), 2.68(2H, s), 4.53(2H, s), 7.21–7.25(1H, m), 7.48(1H, t, J=7.9), 7.61(1H, t, J=1.8), 7.74–7.78(1H, m). |

TABLE 28

| Comp. No. | Physical Date | |
|---|---|---|
| No | M.p. | NMR(CHCl$_3$) |
| I-157 | 103.5–104.5° C. | 1.23(6H, s), 2.63(3H, s), 2.68(2H, s), 4.50(2H, s), 6.88–6.94(2H, m), 7.46–7.51(2H, m). |
| I-158 | 97–98° C. | 1.23(6H, s), 2.64(3H, s), 2.68(2H, s), 4.51(2H, s), 6.93–6.97(1H, m), 7.19–7.31(3H, m). |
| I-159 | 155.5–156.5° C. | 1.24(6H, s), 2.65(3H, s), 2.69(2H, s), 4.54(2H, s), 6.98–7.05(2H, m), 7.28–7.34(1H, m), 7.59–7.63(1H, m). |
| I-160 | 102–106° C. | 1.23(6H, s), 2.23(3H, s), 2.64(3H, s), 2.67(2H, s), 4.00(3H, s), 4.52(2H, s), 7.01–7.05(1H, m), 7.28(1H, t, J=1.8), 7.37(1H, t, J=7.8), 7.45–7.49(1H, m). |
| I-161 | 111–112° C. | 1.23(6H, s), 2.60(3H, s), 2.65(3H, s), 2.69(2H, s), 4.53(2H, s), 7.06–7.10(2H, m), 7.97–8.03(2H, m). |
| I-162 | 124–125° C. | 1.23(6H, s), 2.23(3H, s), 2.64(3H, s), 2.67(2H, s), 4.00(3H, s), 4.52(2H, s), 7.00–7.05(2H, m), 7.65–7.70(2H, m). |
| I-163 | 102–103.5° C. | 1.23(6H, s), 1.32(6H, d, J=6.3), 2.63(2H, s), 2.64(3H, s), 4.52(2H, s), 4.52(1H, sept, J=6.3), 6.90–6.98(3H, m), 7.04–7.13(1H, m) |
| I-164 | 90–92° C. | 0.94(3H, t, J=7.3), 1.23(6H, s), 1.58(2H, sext, J=7.3), 2.51–2.56(2H, m), 2.65(3H, s), 2.65(2H, s), 4.51(2H, s), 6.90(1H, dd, J=7.6, 1.3), 7.07–7.25(3H, m) |
| I-165 | 157–158° C. | 1.23(6H, s), 2.64(3H, s), 2.68(2H, s), 4.49(2H, s), 7.08(1H, d, J=7.9), 7.22(1H, d, J=7.6), 7.50–7.56(1H, m), 7.66–7.69(1H, m) |
| I-166 | 145–146° C. | 1.24(6H, s), 2.64(3H, s), 2.69(2H, s), 4.51(2H, s), 7.00–7.13(7H, m), 7.30–7.37(2H, m) |

TABLE 28-continued

| Comp. No. | Physical Date | |
|---|---|---|
| No | M.p. | NMR(CHCl$_3$) |
| I-167 | 77–79° C. | 0.95(3H, t, J=7.3), 1.23(6H, s), 1.65(2H, sext, J=7.3), 2.58(2H, t, J=7.3), 2.63(3H, s), 2.66(2H, s), 4.51(2H, s), 6.93–7.00(2H, m), 7.14–7.20(2H, m) |

TABLE 29

| Comp. No. | Physical Date | |
|---|---|---|
| No | M.p. | NMR(CHCl$_3$) |
| I-168 | 117–118° C. | 1.23(6H, s), 1.55(9H, s), 2.63(3H, s), 2.67(2H, s), 4.52(2H, s), 6.96–7.01(2H, m), 7.37–7.42(2H, m). |
| I-169 | 55–56° C. | 1.24(6H, s), 2.65(3H, s), 2.69(2H, s), 4.53(2H, s), 7.19(1H, d, J=7.6), 7.26–7.27(1H, m), 7.40–7.52(2H, m). |
| I-170 | 88–90° C. | 1.24(6H, s), 2.65(3H, s), 2.69(2H, s), 4.53(2H, s), 7.10(2H, d, J=8.2), 7.63(2H, d, J=8.2). |
| I-171 | | 1.15(6H, s), 1.18(6H, d, J=6.9), 2.17(3H, s), 2.31(3H, s), 2.64(2H, s), 3.11(1H, sept, J=6.9), 3.78(2H, s), 6.80(1H, d, J=8.2), 7.11–7.18(1H, m), 7.28–7.35(1H, m). |
| I-172 | | 1.15(6H, s), 1.18(6H, d, J=6.9), 2.15(3H, s), 2.31(3H, s), 2.65(2H, s), 3.11(1H, sept, J=6.9), 3.78(2H, s), 6.99(1H, s), 7.11–7.18(1H, m), 7.28–7.35(1H, s). |
| I-173 | 121–123° C. | 1.22(6H, s), 2.64(3H, s), 2.67(2H, s), 3.89(3H, s), 3.89(3H, s), 4.54(2H, s), 6.96(1H, d, J=8.6), 7.67(1H, d, J=2.1), 7.87(1H, dd, J=8.6, 2.1). |
| I-174 | 146–147° C. | 1.24(6H, s), 2.59(2H, s), 2.65(3H, s), 2.96–2.99(4H, m), 3.76–3.79(4H, m), 4.52(2H, s), 6.98–7.17(4H, m). |
| I-175 | 155–157° C. | 1.23(6H, s), 2.64(3H, s), 2.66(2H, s), 3.16–3.20(4H, m), 3.84–3.88(4H, m), 4.51(2H, s), 6.54–6.57(2H, m), 6.70–6.74(1H, m), 7.24–7.30(1H, m). |
| I-176 | | 1.22(6H, d, J=6.6), 1.23(6H, s), 1.38(3H, t, J=7.1), 2.65(3H, s), 2.67(2H, s), 3.08–3.18(1H, m), 4.37(2H, q, J=6.9), 4.52(2H, s), 7.38(1H, d, J=7.9), 7.59(1H, d, J=2.0), 7.82(1H, dd, J=8.1, 1.8). |
| I-177 | 120–122° C. | 1.23(6H, s), 1.50–1.61(2H, m), 1.67–1.75(4H, m), 2.62(3H, s), 2.66(2H, s), 3.13–3.17(4H, m), 4.50(2H, s), 6.92–7.02(4H, m). |
| I-178 | 124–125° C. | 1.23(6H, s), 1.85–1.90(4H, m), 2.62(3H, s), 2.68(2H, s), 3.22–3.27(4H, m), 4.48(2H, s), 6.74–6.80(2H, m), 6.95–6.98(1H, m), 7.03–7.10(1H, m). |

TABLE 30

| Comp. No. | Physical Date | |
|---|---|---|
| No | M.p. | NMR(CHCl$_3$) |
| I-179 | | 1.23(6H, s), 2.50(3H, s), 2.64(3H, s), 2.67(2H, s), 4.51(2H, s), 6.78–6.82(1H, m), 6.91(1H, t, J=2.0), 7.03–7.07(1H, m), 7.25–7.31(1H, m). |
| I-180 | 102–103° C. | 1.23(6H, s), 2.49(3H, s), 2.63(3H, s), 2.67(2H, s), 4.51(2H, s), 6.96–7.01(2H, m), 7.27–7.31(2H, m). |
| I-181 | 82–83° C. | 1.23(6H, s), 2.64(3H, s), 2.67(2H, s), 4.52(2H, s), 7.07(1H, dd, J=7.6, 1.7), 7.14–7.20(1H, m), 7.25–7.34(2H, m). |
| I-182 | | 1.23(6H, s), 2.64(3H, s), 2.69(2H, s), 4.52(2H, s), 6.90(1H, s), 6.93–7.04(2H, m), 7.38(1H, t, J=8.2) |
| I-183 | 68–70° C. | 1.24(6H, s), 2.64(3H, s), 2.69(2H, s), 4.51(2H, s), 7.01–7.07(2H, m), 7.21–7.24(2H, m). |
| I-184 | 169–170° C. | 1.25(6H, s), 2.66(3H, s), 2.70(2H, s), 4.54(2H, s), 7.13–7.18(2H, m), 7.34–7.39(1H, m), 7.59–7.63(2H, m), 7.86–7.91(1H, m), 8.58(1H, dd, J=4.8, 1.6), 8.87(1H, t, J=1.5) |
| I-185 | 92.5–93.5° C. | 1.24(6H, s), 2.65(3H, s), 2.69(2H, s), 4.54(2H, s), 7.05–7.09(1H, m), 7.24(1H, t, J=1.6), 7.34–7.40(2H, m), 7.49(1H, t, J=7.6), 7.87–7.92(1H, m), 8.60(1H, dd, J=4.9, 1.4), 8.87(1H, dd, J=2.3, 0.7) |
| I-186 | | 1.09(6H, s), 2.56(3H, s), 2.58(2H, s), 4.20(2H, s), 7.09–7.12(1H, m), 7.24–7.30(2H, m), 7.36–7.45(2H, m), 7.75–7.79 (1H, m), 8.54(1H, dd, J=4.9, 1.6), 8.68(1H, dd, J=2.3, 0.7) |
| I-187 | 110.5–111.5° C. | 1.17(6H, s), 2.51(3H, s), 2.61(2H, s), 4.33(2H, s), 6.93–7.19(7H, m), 7.23–7.30(2H, m) |
| I-188 | 75–76° C. | 1.14(6H, s), 1.43(6H, t, J=7.4), 2.61(2H, s), 3.65(2H, s), 3.84(3H, s), 4.08(4H, q, J=7.4), 6.46(1H, dd, J=8.1, 2.2), 6.52(1H, d, J=2.2), 6.84(1H, d, J=8.4). |
| I-189 | | 1.19(6H, s), 2.61(2H, s), 3.65(2H, s), 3.85(3H, s), 3.88(3H, s), 6.85–6.99(3H, m), 7.02–7.15(1H, m). |

TABLE 31

| Comp. No. | Physical Date | |
|---|---|---|
| No | M.p. | NMR(CHCl$_3$) |
| I-190 | | 1.13(6H, s), 1.23(3H, t, J=7.4), 2.62(2H, s), 2.66(2H, q, J=7.4), 3.64(2H, s), 3.84(3H, s), 6.84(2H, d, J=8.6), 7.16(2H, d, J=8.6). |
| I-191 | 45–47° C. | 1.14(6H, s), 1.25(6H, d, J=7.0), 2.62(2H, s), 2.91(1H, sept, J=7.0), 3.64(2H, s), 3.84(3H, s), 6.86(2H, d, J=8.6), 7.19(2H, d, J=8.6). |
| I-192 | 93–95° C. | 1.15(6H, s), 2.31(3H, s), 2.62(2H, s), 3.80(3H, s), 3.85(3H, s), 6.85–6.99(3H, m), 7.02–7.15(1H, m). |
| I-193 | 65–67° C. | 1.13(6H, s), 1.23(3H, t, J=7.4), 2.31(3H, s), 2.62(2H, s), 2.65(2H, q, J=7.4), 3.77(2H, s), 6.90(2H, d, J=8.3), 7.21(2H, d, J=8.3). |
| I-194 | 95–97° C. | 1.15(6H, s), 1.24(6H, d, J=7.0), 2.31(3H, s), 2.64(2H, s), 2.91(1H, sept, J=7.0), 3.77(2H, s), 6.90(2H, d, J=8.6), 7.21(2H, d, J=8.6). |
| I-195 | 94–96° C. | 1.15(6H, s), 1.41(3H, t, J=7.0), 2.31(3H, s), 2.64(2H, s), 3.77(2H, s), 4.05(2H, q, J=7.4), 6.90–6.99(4H, m). |

TABLE 31-continued

| Comp. No. | Physical Date | |
|---|---|---|
| No | M.p. | NMR(CHCl$_3$) |
| I-196 | 99–100° C. | 1.15(6H, s), 1.47(3H, t, J=7.0), 2.32(3H, s), 2.66(2H, s), 3.77(2H, s), 3.88(3H, s), 4.08(2H, q, J=7.0), 6.52(1H, d, J=8.2), 6.56(1H, d, J=2.1), 6.88(1H, d, J=8.2). |
| I-197 | 133–134° C. | 1.23(6H, s), 1.50–1.75(6H, m), 2.63(3H, s), 2.65(2H, s), 3.18(4H, t, J=5.4), 4.51(2H, s), 6.47–6.57(2H, m), 6.72–6.76(1H, m), 7.21(1H, d, J=8.1) |
| I-198 | 124–125° C. | 1.17(6H, t, J=6.9), 1.23(6H, s), 2.61(3H, s), 2.68(2H, s), 3.35(4H, q, J=6.9), 4.49(2H, s), 6.68(2H, d, J=8.9), 7.04(2H, d, J=8.9) |
| I-199 | 85–87° C. | 1.22(6H, s), 2.63(3H, s), 2.67(2H, s), 3.89(3H, s), 3.92(3H, s), 4.54(2H, s), 7.01(1H, d, J=7.9), 7.62(1H, d, J=1.3), 7.67(1H, dd, J=7.9, 1.7) |
| I-200 | 137–138° C. | 1.23(6H, s), 2.11–2.22(2H, m), 2.62(2H, t, J=7.9), 2.64(3H, s), 2.67(2H, s), 3.88(2H, t, J=7.1), 4.52(2H, s), 6.81–6.84(1H, m), 7.30–7.50(3H, m) |

TABLE 32

| Comp. No. | Physical Date | |
|---|---|---|
| No | M.p. | NMR(CHCl$_3$) |
| I-201 | 86.5–87.5° C. | 1.22(6H, s), 2.62(3H, s), 2.67(2H, s), 4.50(2H, s), 6.71(1H, t, J=2.0), 6.76–6.82(2H, m), 7.02–7.13(3H, m), 7.29–7.37(3H, m) |
| I-202 | 162–163° C. | 1.25(6H, s), 2.65(3H, s), 2.70(2H, s), 4.54(2H, s), 7.10–7.14(2H, m), 7.33–7.46(3H, m), 7.59–7.63(4H, m) |
| I-203 | 56.5–57.5° C. | 1.06(6H, s), 2.51(3H, s), 2.59(2H, s), 4.14(2H, s), 7.07(1H, dd, J=8.2, 1.3), 7.21–7.45(8H, m) |
| I-204 | 97–99° C. | 1.24(6H, s), 2.65(3H, s), 2.68(2H, s), 4.54(2H, s), 7.00–7.04(1H, m), 7.25–7.26(1H, m), 7.33–7.48(5H, m), 7.60–7.63(2H, m) |
| I-205 | 95–96° C. | 1.21(6H, s), 1.21(6H, d, J=6.9), 2.61(2H, s), 4.13(3H, s), 4.16(2H, s), 6.77–6.81(1H, m), 7.13–7.16(2H, m), 7.29–7.33(1H, m) |
| I-206 | 128–129° C. | 1.18(6H, d, J=6.9), 1.22(6H, s), 2.63(3H, s), 2.66(2H, s), 2.96–3.06(1H, m), 4.48(2H, s), 6.67(1H, d, J=8.2), 7.47(1H, dd, J=8.2, 1.7), 7.59(1H, d, J=2.0) |
| I-207 | 149–150° C. | 1.23(6H, s), 2.63(3H, s), 2.67(2H, s), 3.71(8H, m), 3.86(3H, s), 4.53(2H, s), 6.95–7.05(3H, m) |
| I-208 | 124–126° C. | 1.23(6H, s), 2.61(3H, s), 2.67(2H, s), 2.96(6H, s), 4.50(2H, s), 6.74(2H, d, J=8.2), 7.04(2H, d, J=8.2). |
| I-209 | 107–109° C. | 1.23(6H, s), 2.63(3H, s), 2.65(2H, s), 2.96(6H, s), 4.51(2H, s), 6.34(1H, d, J=2.0), 6.38(1H, d, J=8.0), 6.54(1H, dd, J=8.0, 2.0), 7.24(2H, d, J=8.0). |
| I-210 | 98–99° C. | 1.06(3H, t, J=7.4), 1.23(6H, s), 2.63(5H, s), 2.65(3H, s), 2.99(2H, q, J=7.4), 4.51(2H, s), 6.98–7.10(3H, m), 7.15–7.20(1H, m). |

TABLE 32-continued

| Comp. No. | Physical Date | |
|---|---|---|
| No | M.p. | NMR(CHCl$_3$) |
| I-211 | 94–96° C. | 0.84(3H, t, J=7.4), 1.22(6H, s), 1.49(2H, sext, J=7.3), 2.63(3H, s), 2.65(2H, s), 2.72(3H, s), 2.84(2H, t, J=7.4), 4.51(2H, s), 6.90–7.05(3H, m), 7.10–7.15(1H, m). |

TABLE 33

| Comp. No. | Physical Date | |
|---|---|---|
| No | M.p. | NMR(CHCl$_3$) |
| I-212 | 98–99° C. | 1.02(6H, t, J=7.4), 1.22(6H, s), 2.61(2H, s), 2.63 (3H, s), 3.06(4H, q, J=7.4), 4.51(2H, s), 6.98–7.10(4H, m). |
| I-213 | 83–84° C. | 1.23(6H, s), 2.64(3H, s), 2.71(2H, s), 4.57(2H, s), 6.90–7.12(3H, m) |
| I-214 | | 1.19(6H, d, J=6.9), 1.23(6H, s), 2.64(3H, s), 2.67(2H, s), 3.06(1H, sept, J=6.9), 4.49(2H, s), 6.85(1H, d, J=8.2), 7.14(1H, dd, J=8.2, 2.3), 7.27(1H, d, J=2.3). |
| I-215 | 83–85° C. | 1.23(6H, s), 2.32(3H, s), 2.63(3H, s), 2.66(2H, s), 2.71(6H, s), 4.50(2H, s), 6.75–6.80(1H, m), 6.98(1H, s), 6.97–7.00(1H, m). |
| I-216 | 99–100° C. | 1.23(6H, s), 2.33(3H, s), 2.62(3H, s), 2.65(2H, s), 2.70(6H, s), 4.50(2H, s), 6.78(2H, t, J=7.9), 6.91(1H, d, J=7.9). |
| I-217 | 98–99° C. | 1.23(6H, s), 2.30(3H, s), 2.63(3H, s), 2.64(2H, s), 2.67(6H, s), 4.50(2H, s), 6.81(1H, s), 6.92(2H, s). |
| I-218 | 117–19° C. | 1.23(6H, s), 2.63(3H, s), 2.65(2H, s), 2.68(6H, s), 4.50(2H, s), 6.89(1H, d, J=8.5), 6.99(1H, d, J=2.0), 7.04(1H, dd, J=7.9, 2.0). |
| I-219 | 68–70° C. | 1.22(6H, s), 2.22(6H, s), 2.64(3H, s), 2.66(2H, s), 4.54(2H, s), 6.93–6.98(1H, m), 7.04(2H, d, J=8.0). |
| I-220 | 97–99° C. | 1.22(6H, s), 1.34(3H, t, J=7.4), 2.64(2H, s), 2.72(6H, s), 3.25(2H, q, J=7.4), 4.47(2H, s), 6.94–7.05(3H, m), 7.15–7.20(1H, m). |
| I-221 | 118–119° C. | 1.22(6H, s), 1.34(3H, t, J=7.4), 2.64(2H, s), 2.95(6H, s), 3.25(2H, q, J=7.4), 4.47(2H, s), 6.34(1H, d, J=7.5), 6.38(1H, s), 6.52(1H, d, J=7.5), 7.24(1H, t, J=7.5). |
| I-222 | 74–76° C. | 1.22(6H, s), 1.34(3H, t, J=7.4), 2.33(3H, s), 2.63(2H, s), 2.70(6H, s), 3.25(2H, q, J=7.4), 4.47(2H, s), 6.78(1H, d, J=7.5), 6.82(1H, s), 6.91(1H, t, J=7.5). |

TABLE 34

| Comp. No. | Physical Date | |
|---|---|---|
| No | M.p. | NMR(CHCl$_3$) |
| I-223 | | 1.22(6H, s), 1.25(6H, d, J=7.0), 1.34(3H, t, J=7.4), 2.65(2H, s), 2.91(1H, sept, J=7.0), 3.25(2H, q, J=7.4), 4.50(2H, s), 6.98(2H, d, J=8.2), 7.28(2H, d, J=8.2). |

TABLE 34-continued

| Comp. No. | Physical Date | |
|---|---|---|
| No | M.p. | NMR(CHCl$_3$) |
| I-224 | | 1.21(6H, s), 2.62(3H, s), 2.66(2H, s), 2.97(3H, d, J=4.9), 3.84(3H, s), 4.51(2H, s), 6.66(1H, brs), 6.96(1H, d, J=7.9), 7.30–7.33(1H, m), 7.49(1H, d, J=1.3) |
| I-225 | 69–71° C. | 1.23(6H, s), 2.64(3H, s), 2.68(2H, s), 4.52(2H, s), 6.49(1H, t, J=74.6), 7.04–7.26(4H, m) |
| I-226 | | 1.23(6H, s), 2.64(3H, s), 2.68(2H, s), 4.51(2H, s), 6.50(1H, t, J=74.2), 7.00–7.05(2H, s), 7.11–7.16(2H, m) |
| I-227 | 81–83° C. | 1.17(6H, t, J=7.0), 1.23(6H, s), 2.63(3H, s), 2.66(2H, s), 3.35(4H, q, J=7.0), 4.52(2H, s), 6.29(1H, s), 6.30(1H, dt, J=8.2, 2.3), 6.49(1H, dd, J=8.2, 2.3), 7.19(1H, t, J=8.2). |
| I-228 | 106–107° C. | 1.21(6H, s), 2.61(3H, s), 2.64(2H, s), 2.70(6H, s), 4.47(2H, s), 6.90(2H, s), 6.93(1H, s). |
| I-229 | 121–122° C. | 1.23(6H, s), 2.62(3H, s), 2.65(2H, s), 2.70(6H, s), 4.48(2H, s), 6.50–6.70(2H, m), 6.93(1H, dd, J=8.5, 6.2). |
| I-230 | 85–86° C. | 1.21(6H, s), 2.63(3H, s), 2.64(2H, s), 2.66(6H, s), 4.49(2H, s), 6.74–6.79(2H, m), 6.93–6.98(1H, m). |
| I-231 | 82–84° C. | 1.23(6H, s), 1.25(3H, t, J=7.6), 2.62(3H, s), 2.66(2H, s), 2.67(2H, q, J=7.6), 2.71(6H, s), 4.50(2H, s), 6.80(1H, d, J=7.6), 6.84(1H, s), 6.93(1H, d, J=7.6). |
| I-232 | 75–76° C. | 1.22(3H, t, J=7.6), 1.23(6H, s), 2.60(2H, q, J=7.6), 2.63(3H, s), 2.64(2H, s), 2.68(6H, s), 4.50(2H, s), 6.83(1H, s), 6.93(2H, s). |
| I-233 | 86–88° C. | 1.22(6H, s), 1.33(3H, t, J=7.4), 2.64(2H, s), 2.71(6H, s), 3.24(2H, q, J=7.4), 4.47(2H, s), 6.92(2H, s), 6.94(1H, s). |

TABLE 35

| Comp. No. | Physical Date | |
|---|---|---|
| No | M.p. | NMR(CHCl$_3$) |
| I-234 | 70–71° C. | 1.22(6H, s), 1.34(3H, t, J=7.4), 2.64(2H, s), 2.71(6H, s), 3.25(2H, q, J=7.4), 4.46(2H, s), 6.60–6.68(2H, m), 6.92–6.94(1H, m). |
| I-235 | 80–82° C. | 1.22(6H, s), 1.24(3H, t, J=7.6), 1.33(3H, t, J=7.4), 2.60(2H, q, J=7.6), 2.61(2H, s), 2.71(6H, s), 3.24(2H, q, J=7.4), 4.47(2H, s), 6.81(1H, d, J=7.6), 6.94(1H, s), 6.94(1H, d, J=7.6). |
| I-236 | | 1.03(3H, t, J=7.3), 1.20(6H, d, J=6.9), 1.23(6H, s), 1.40(3H, d, J=6.9), 1.61–1.89(2H, m), 2.63(2H, s), 3.15(1H, sept, J=6.9), 3.95(1H, q, J=6.9), 4.47(2H, s), 6.89–6.92(1H, m), 7.13–7.20(2H, m), 7.31–7.34(1H, m) |
| I-237 | | 1.05(6H, d, J=6.6), 1.21(6H, d, J=6.6), 1.23(6H, s), 1.98–2.08(1H, m), 2.64(2H, s), 3.16(1H, sept, J=6.6), 3.20(1H, d, J=6.6), 4.49(2H, s), 6.88–6.92(1H, m), 7.13–7.22(2H, m), 7.30–7.35(1H, m) |

TABLE 35-continued

| Comp. No. | Physical Date | |
|---|---|---|
| No | M.p. | NMR(CHCl$_3$) |
| I-238 | 102–104° C. | 1.20(6H, d, J=6.9), 1.22(6H, s), 2.61(2H, s), 2.85–2.95(1H, m), 3.19(3H, d, J=4.6), 4.46(2H, s), 6.73–6.79(1H, m), 7.14–7.20(2H, m), 7.29–7.34(1H, m), 12.40(1H, brs) |
| I-239 | 58–60° C. | 1.23(6H, s), 2.17(3H, s), 2.64(3H, s), 2.65(2H, s), 2.70(6H, s), 4.52(2H, s), 6.63(1H, d, J=7.9), 6.87(1H, d, J=7.9), 7.14(1H, d, J=7.9). |
| I-240 | 100–101° C. | 1.23(6H, s), 2.62(3H, s), 2.64(2H, s), 2.78(6H, s), 3.89(3H, s), 4.52(2H, s), 6.60–6.70(2H, m), 6.94(1H, d, J=7.9). |
| I-241 | 82–83° C. | 1.23(6H, s), 2.30(3H, s), 2.63(3H, s), 2.65(2H, s), 2.70(6H, s), 4.52(2H, s), 6.63(1H, dt, J=7.9, 1.9), 6.70(1H, d, J=1.9), 7.14(1H, d, J=7.9). |
| I-242 | 99–100° C. | 1.23(6H, s), 2.63(3H, s), 2.68(2H, s), 2.81(6H, s), 4.50(2H, s), 6.91(1H, dt, J=8.4, 2.6), 7.06(1H, d, J=8.4), 7.14(1H, d, J=2.6). |
| I-243 | 63–64° C. | 1.23(6H, s), 2.63(3H, s), 2.67(2H, s), 2.78(6H, s), 3.89(3H, s), 4.52(2H, s), 6.67(1H, s), 6.70(1H, d, J=7.9), 6.81(1H, d, J=7.9). |
| I-244 | 68–70° C. | 0.88(6H, t, J=7.5), 1.22(6H, d, J=6.9), 1.35(3H, t, J=7.4), 1.50–1.70(4H, m), 2.61(2H, s), 3.15(1H, sept, J=6.9), 3.29(2H, q, J=7.4), 4.44(2H, s), 6.89–6.92(1H, m), 7.08–7.21(2H, m), 7.30–7.35(1H, m). |

TABLE 36

| Comp. No. | Physical Date | |
|---|---|---|
| No | M.p. | NMR(CHCl$_3$) |
| I-245 | 81–82° C. | 1.14(6H, s), 1.20(6H, d, J=6.9), 2.63(2H, s), 3.06(2H, s), 3.08(1H, sept, J=6.9), 3.18(3H, s), 6.74(1H, dd, J=7.3, 1.7), 6.98–7.10(2H, m), 7.20–7.24(1H, m) |
| I-246 | 47–49° C. | 0.95(3H, t, J=7.3), 1.13(6H, s), 1.20(6H, d, J=6.9), 1.55–1.74(2H, m), 2.62(2H, s), 3.03–3.11(3H, m), 3.52–3.57(2H, m), 6.73(1H, dd, J=7.6, 1.7), 6.96–7.10(2H, m), 7.21(1H, dd, J=7.3, 1.7) |
| I-247 | 68–70° C. | 1.11(6H, d, J=6.9), 1.18(6H, d, J=6.9), 1.19(6H, d, J=6.9), 2.56(2H, s), 2.89(2H, s), 3.08(1H, sept, J=6.9), 5.08(1H, sept, J=6.9), 6.73(1H, dd, J=7.9, 1.7), 6.99–7.10(2H, m), 7.21(1H, dd, J=7.9, 1.7) |
| I-248 | | 0.97(6H, d, J=6.9), 1.14(6H, s), 1.18(6H, d, J=6.9), 2.05–2.15(1H, m), 2.62(2H, s), 3.07(2H, s), 3.08(1H, sept, J=6.9), 3.44(2H, d, J=7.6), 6.71(1H, dd, J=7.6, 1.7), 6.96–7.09(2H, m), 7.21(1H, dd, J=7.6, 1.7) |
| I-249 | 96–97° C. | 1.23(6H, s), 2.64(3H, s), 2.68(2H, s), 4.59(2H, s), 7.04(1H, d, J=7.3), 7.41–7.50(3H, m), 7.67(1H, d, J=7.3), 7.87(1H, dd, J=7.3, 2.1), 8.05(1H, d, J=7.3). |

TABLE 36-continued

| Comp. No. | Physical Date | |
|---|---|---|
| No | M.p. | NMR(CHCl$_3$) |
| I-250 | 108–109° C. | 1.24(6H, s), 2.67(3H, s), 2.69(2H, s), 4.59(2H, s), 7.15(1H, d, J=7.3), 7.41(1H, q, J=7.3), 7.69(1H, t, J=8.4), 7.91(1H, d, J=7.3), 8.45(1H, d, J=8.4), 8.92–8.95(1H, m). |
| I-251 | 105–107° C. | 1.22(6H, s), 2.62(3H, s), 2.65(2H, s), 3.97(3H, s), 4.53(2H, s), 6.87–6.90(1H, m), 7.25–7.30(1H, m), 7.96–7.99(1H, m). |
| I-252 | 132–133° C. | 1.23(6H, s), 2.63(3H, s), 2.68(2H, s), 2.92(3H, s), 4.49(2H, s), 6.73–6.78(1H, m), 7.20–7.23(1H, m), 8.05–8.07(1H, m) |
| I-253 | 118–120° C. | 1.23(6H, s), 2.60(3H, s), 2.63(2H, s), 4.52(2H, s), 7.30(2H, s), 8.12(1H, s). |
| I-254 | 112–113° C. | 1.23(6H, s), 2.63(3H, s), 2.69(2H, s), 3.94(3H, s), 4.51(2H, s), 6.76(1H, d, J=8.1), 7.35(1H, dd, J=8.1, 2.1), 7.92(1H, d, J=2.1). |
| I-255 | 109–110° C. | 1.23(6H, s), 1.40(3H, t, J=7.0), 2.62(3H, s), 2.66(2H, s), 4.38(2H, q, J=7.0), 4.51(2H, s), 6.75(1H, d, J=8.1). 7.35(1H, dd, J=8.1, 2.1), 7.90(1H, d, J=2.1). |

TABLE 37

| Comp. No. | Physical Date | |
|---|---|---|
| No | M.p. | NMR(CHCl$_3$) |
| I-256 | 75–76° C. | 1.03(3H, t, J=7.6), 1.22(6H, s), 1.76(2H, sext, J=7.6), 2.63(3H, s), 2.65(2H, s), 4.24(2H, t, J=7.6), 4.51(2H, s), 6.76(1H, d, J=8.1), 7.35(1H, dd, J=8.1, 2.1), 7.92(1H, d, J=2.1). |
| I-257 | 74–76° C. | 1.24(6H, s), 1.36(6H, d, J=6.3), 2.63(3H, s), 2.70(2H, s), 4.51(2H, s), 5.28(1H, sept, J=6.3), 6.70(1H, d, J=8.1), 7.32(1H, dd, J=8.1, 2.1), 7.92(1H, d, J=2.1). |
| I-258 | 102–104° C. | 1.23(6H, s), 2.58(3H, s), 2.63(2H, s), 2.69(3H, s), 4.51(2H, s), 7.20–7.26(2H, m), 8.21(1H, d, J=2.1). |
| I-259 | 81–83° C. | 1.23(6H, s), 1.38(3H, t, J=7.3), 2.63(3H, s), 2.63(2H, s), 3.18(2H, q, J=7.3), 4.51(2H, s), 7.15–7.26(2H, m), 8.21(1H, d, J=2.1). |
| I-260 | 78–79° C. | 1.05(3H, t, J=7.4), 1.23(6H, s), 1.75(2H, sext, J=7.3), 2.63(3H, s), 2.65(2H, s), 3.15(2H, t, J=7.4), 4.51(2H, s), 7.15–7.26(2H, m), 8.20(1H, d, J=2.1). |
| I-261 | 102–103° C. | 1.23(6H, s), 1.40(6H, d, J=6.6), 2.63(3H, s), 2.66(2H, s), 4.00(1H, sept, J=6.6), 4.51(2H, s), 7.15–7.26(2H, m), 8.22(1H, d, J=2.1). |
| I-262 | 109–110° C. | 1.22(6H, s), 2.61(3H, s), 2.65(2H, s), 2.70(6H, s), 3.80(3H, s), 4.48(2H, s), 6.47(1H, dd, J=7.9, 2.1), 6.56(1H, d, J=2.1), 6.95(1H, d, J=7.9). |
| I-263 | 99–100° C. | 1.22(6H, s), 2.62(3H, s), 2.63(2H, s), 2.64(6H, s), 3.78(3H, s), 4.48(2H, s), 6.59(1H, d, J=2.1), 6.64(1H, dd, J=7.9, 2.1), 6.98(1H, d, J=7.9). |
| I-264 | 114–115° C. | 0.98(6H, t, J=7.0), 1.23(6H, s), 2.16(3H, s), 2.63(3H, s), 2.64(2H, s), 2.98(4H, q, J=7.0), 4.52(2H, s), 6.65(1H, s), 6.89(1H, d, J=7.9), 7.13(1H, t, J=7.9). |

TABLE 37-continued

| Comp. No. | Physical Date | |
|---|---|---|
| No | M.p. | NMR(CHCl$_3$) |
| I-265 | 66–67° C. | 0.98(6H, t, J=7.0), 1.23(6H, s), 2.16(3H, s), 2.63(3H, s), 2.64(2H, s), 2.98(4H, q, J=7.0), 4.52(2H, s), 6.63(1H, dd, J=7.9, 2.1), 6.70(1H, d, J=2.1), 7.16(1H, d, J=7.9). |
| I-266 | 88–90° C. | 1.04(6H, t, J=7.0), 1.24(6H, s), 2.63(3H, s), 2.67(2H, s), 3.17(4H, q, J=7.0), 3.86(3H, s), 4.51(2H, s), 6.67(1H, s), 6.70(1H, d, J=7.9), 6.85(1H, d, J=7.9). |

TABLE 38

| Comp. No. | Physical Date | |
|---|---|---|
| No | M.p. | NMR(CHCl$_3$) |
| I-267 | 138–140° C. | 0.82–0.92(9H, m), 1.18(3H, d, J=6.9), 1.51–1.65(6H, m), 2.62(2H, s), 2.65(3H, s), 2.87(1H, sept, J=6.9), 4.33(1H, d, J=13.5), 4.59(1H, d, J=13.5), 6.89–6.92(1H, m), 7.13–7.28(3H, m) |
| I-268 | 161–163° C. | 0.89–0.95(6H, m), 1.21(6H, d, J=6.9), 1.25–1.54(8H, m), 2.62(2H, s), 2.65(3H, s), 3.10(1H, sept, J=6.9), 4.47(2H, s), 6.88–6.92(1H, m), 7.14–7.18(2H, m), 7.31–7.34(1H, m) |
| I-269 | | 1.21(6H, d, J=6.9), 1.65–1.88(8H, m), 2.64(3H, s), 2.75(2H, s), 3.09(1H, sept, J=6.9), 4.57(2H, s), 6.90–6.94(1H, m), 7.13–7.20(2H, m), 7.30–7.35(1H, m) |
| I-270 | | 1.21(6H, d, J=6.9), 1.37–1.54(8H, m), 1.76–1.80(2H, m), 2.65(3H, s), 2.67(2H, s), 3.09(1H, sept, J=6.9), 4.54(2H, s), 6.89(1H, m), 7.11–7.21(2H, m), 7.29–7.34(1H, m) |

TABLE 39

| Comp. No. | Physical Date | |
|---|---|---|
| No | M.p. | NMR(CHCl$_3$) |
| I-271 | | 1.04(3H, s), 1.08(3H, s), 1.29(6H, d), J=6.9), 2.69(2H, s), 3.40(1H, sept, J=6.9), 3.43(3H, s), 3.51(2H, s), 7.18–7.29(2H, m), 7.36–7.45(2H, m) |
| I-272 | | 0.96(3H, s), 1.05(3H, s), 1.25(3H, d, J=6.9), 1.26(3H, d, J=6.9), 2.61(1H, d, J=12), 2.70(1H, d, J=12), 3.39(1H, sept, J=6.9), 3.45–3.58(2H, m), 7.02–7.07(2H, m), 7.11–7.18(1H, m), 7.38–7.45(2H, m), 7.61–7.70(2H, m) |
| I-273 | | 0.84(3H, s), 1.00(3H, s), 1.25(3H, d, J=6.9), 1.29(3H, d, J=6.9), 2.43(3H, s), 2.53(1H, d, J=12), 2.64(1H, d, J=12), 3.29(1H, d, J=16), 3.42(1H, d, J=16), 3.47(1H, sept, J=6.9), 7.09–7.19(2H, m), 7.24–7.29(2H, m), 7.38–7.45(2H, m), 7.81–7.86(2H, m) |
| I-274 | | 0.99(6H, s), 1.19(6H, d, J=6.9), 2.40(3H, s), 2.67(2H, s), 2.87(1H, sept, J=6.9), 3.43(2H, s), 7.11–7.29(6H, m), 7.68(2H, d, J=8.1) |

TABLE 39-continued

| Comp. No. | Physical Date | |
|---|---|---|
| No | M.p. | NMR(CHCl₃) |
| I-275 | | 1.07(6H, s), 1.26(6H, d, J=6.9), 1.38(3H, t, J=7.2), 2.71(2H, s), 2.93(1H, sept, J=6.9), 3.51(2H, s), 3.60(2H, q, J=7.2), 7.20–7.30(4H, m) |
| I-276 | | 1.19(6H, s), 1.23(6H, d, J=6.9), 2.77(2H, s), 2.87(1H, sept, J=6.9), 3.58(2H, s), 6.65–6.69(2H, m), 6.91(1H, d, J=7.5), 7.20(1H, t, J=7.5), 7.51(2H, d, J=9.3), 8.22(2H, d, J=9.3) |
| I-277 | | 0.99(6H, s), 1.20(6H, d, J=6.9), 2.67(2H, s), 2.88(1H, sept, J=6.9), 3.44(2H, s), 3.85(3H, s), 6.86–6.90(2H, m), 7.11–7.26(4H, m), 7.72–7.76(2H, m) |

TABLE 40

| Comp. No. | Physical Date | |
|---|---|---|
| No | M.p. | NMR(CHCl₃) |
| I-278 | | 1.03(6H, s), 1.20(6H, d, J=6.9), 2.70(2H, s), 2.88(1H, sept, J=6.9), 3.44(2H, s), 7.08–7.31(4H, m), 7.60(1H, t, J=8.4), 8.04(1H, d, J=8.4), 8.39(d, J=8.4), 8.74(1H, s) |
| I-279 | | 1.01(6H, s), 1.19(6H, d, J=6.9), 2.69(2H, s), 2.88(1H, sept, J=6.9), 3.42(2H, s), 7.09–7.32(4H, m), 7.68(2H, d, J=8.4), 7.92(2H, d, J=8.4) |
| I-280 | | 1.19(3H, s), 1.21(3H, s), 1.23–1.30(6H, m), 2.62(1H, d, J=12), 2.82(1H, sept, J=6.9), 3.02(1H, d, J=12), 3.46–3.70 (2H, m), 6.53–6.60(2H, m), 6.86(1H, d, J=7.8), 7.13(1H, t, J=7.8), 7.28–7.40(2H, m), 7.61–7.66(1H, m), 7.90(1H, dd, J=7.5, 1.2) |

The following compounds are within the scope of the present invention. These compounds can be prepared in accordance with the above examples.

The numbers of left column in Table represent Compound No.

TABLE 41-A

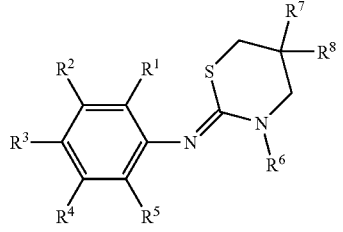

| | R¹ | R² | R³ | R⁴ | R⁵ | R⁶ | R⁷ | R⁸ |
|---|---|---|---|---|---|---|---|---|
| A-1 | H | Pr | H | H | H | CSSMe | Me | Me |
| A-2 | Prⁱ | H | Cl | H | H | CSSMe | Me | Me |
| A-3 | H | Buˢ | H | H | H | CSSMe | Me | Me |
| A-4 | H | H | Buˢ | H | H | CSSMe | Me | Me |
| A-5 | OPr | H | H | H | H | CSSMe | Me | Me |
| A-6 | OBu | H | H | H | H | CSSMe | Me | Me |
| A-7 | H | SEt | H | H | H | CSSMe | Me | Me |
| A-8 | H | H | SEt | H | H | CSSMe | Me | Me |
| A-9 | H | SPrⁱ | H | H | H | CSSMe | Me | Me |
| A-10 | H | H | SPrⁱ | H | H | CSSMe | Me | Me |
| A-11 | H | OCHF₂ | H | H | H | CSSMe | Me | Me |
| A-12 | Prⁱ | H | NMe₂ | H | H | CSSMe | Me | Me |
| A-13 | Prⁱ | NMe₂ | H | H | H | CSSMe | Me | Me |
| A-14 | Et | Et | H | H | H | CSSMe | Me | Me |
| A-15 | H | Et | Et | H | H | CSSMe | Me | Me |
| A-16 | Buⁱ | H | H | H | H | CSSMe | Me | Me |
| A-17 | H | Buⁱ | H | H | H | CSSMe | Me | Me |
| A-18 | H | H | Buⁱ | H | H | CSSMe | Me | Me |
| A-19 | H | N(Me)Et | H | H | H | CSSMe | Me | Me |
| A-20 | H | N(Me)Pr | H | H | H | CSSMe | Me | Me |
| A-21 | NPr₂ | H | H | H | H | CSSMe | Me | Me |
| A-22 | H | NPr₂ | H | H | H | CSSMe | Me | Me |
| A-23 | H | H | NPr₂ | H | H | CSSMe | Me | Me |
| A-24 | H | NPr₂ | Me | H | H | CSSMe | Me | Me |
| A-25 | H | Buᵗ | H | H | H | CSSMe | Me | Me |

TABLE 41-B

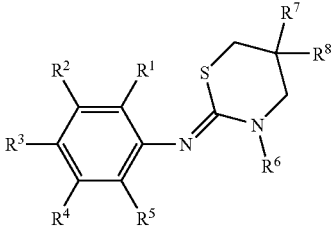

| | R¹ | R² | R³ | R⁴ | R⁵ | R⁶ | R⁷ | R⁸ |
|---|---|---|---|---|---|---|---|---|
| A-26 | H | CH₂OMe | H | H | H | CSSMe | Me | Me |
| A-27 | H | H | CH₂OMe | H | H | CSSMe | Me | Me |
| A-28 | CH₂OEt | H | H | H | H | CSSMe | Me | Me |
| A-29 | H | CH₂OEt | H | H | H | CSSMe | Me | Me |
| A-30 | H | H | CH₂OEt | H | H | CSSMe | Me | Me |
| A-31 | CH₂SMe | H | H | H | H | CSSMe | Me | Me |
| A-32 | H | CH₂SMe | H | H | H | CSSMe | Me | Me |
| A-33 | H | H | CH₂SMe | H | H | CSSMe | Me | Me |

TABLE 41-B-continued

| | R¹ | R² | R³ | R⁴ | R⁵ | R⁶ | R⁷ | R⁸ |
|---|---|---|---|---|---|---|---|---|
| A-34 | CH₂SEt | H | H | H | H | CSSMe | Me | Me |
| A-35 | H | CH₂SEt | H | H | H | CSSMe | Me | Me |
| A-36 | H | H | CH₂SEt | H | H | CSSMe | Me | Me |
| A-37 | CH₂NMe₂ | H | H | H | H | CSSMe | Me | Me |
| A-38 | H | CH₂NMe₂ | H | H | H | CSSMe | Me | Me |
| A-39 | H | H | CH₂NMe₂ | H | H | CSSMe | Me | Me |
| A-40 | CH₂NEt₂ | H | H | H | H | CSSMe | Me | Me |
| A-41 | H | CH₂NEt₂ | H | H | H | CSSMe | Me | Me |
| A-42 | H | H | CH₂NEt₂ | H | H | CSSMe | Me | Me |
| A-43 | OCH₂CH₂OMe | H | H | H | H | CSSMe | Me | Me |
| A-44 | H | OCH₂CH₂OMe | H | H | H | CSSMe | Me | Me |
| A-45 | H | H | OCH₂CH₂OMe | H | H | CSSMe | Me | Me |
| A-46 | OCH₂CH₂SMe | H | H | H | H | CSSMe | Me | Me |
| A-47 | H | OCH₂CH₂SMe | H | H | H | CSSMe | Me | Me |
| A-48 | H | H | OCH₂CH₂SMe | H | H | CSSMe | Me | Me |
| A-49 | OCH₂CH₂NMe₂ | H | H | H | H | CSSMe | Me | Me |
| A-50 | H | OCH₂CH₂NMe₂ | H | H | H | CSSMe | Me | Me |

TABLE 41-C

| | R¹ | R² | R³ | R⁴ | R⁵ | R⁶ | R⁷ | R⁸ |
|---|---|---|---|---|---|---|---|---|
| A-51 | H | H | OCH₂CH₂NMe₂ | H | H | CSSMe | Me | Me |
| A-52 | F | H | F | H | H | CSSMe | Me | Me |
| A53 | Cl | H | Cl | H | H | CSSMe | Me | Me |
| A-54 | OMe | Cl | H | H | H | CSSMe | Me | Me |
| A-55 | OMe | H | Cl | H | H | CSSMe | Me | Me |
| A-56 | OMe | Me | H | H | H | CSSMe | Me | Me |
| A-57 | OMe | Et | H | H | H | CSSMe | Me | Me |
| A-58 | OMe | H | Et | H | H | CSSMe | Me | Me |
| A-59 | OMe | H | Prⁱ | H | H | CSSMe | Me | Me |
| A-60 | OMe | H | OEt | H | H | CSSMe | Me | Me |
| A-61 | OMe | H | OPr | H | H | CSSMe | Me | Me |
| A-62 | OMe | NMe₂ | H | H | H | CSSMe | Me | Me |
| A-63 | OMe | NEt₂ | H | H | H | CSSMe | Me | Me |
| A-64 | OEt | NMe₂ | H | H | H | CSSMe | Me | Me |
| A-65 | OEt | NEt₂ | H | H | H | CSSMe | Me | Me |
| A-66 | H | OMe | F | H | H | CSSMe | Me | Me |
| A-67 | H | OMe | Cl | H | H | CSSMe | Me | Me |
| A-68 | H | OMe | OPrⁱ | H | H | CSSMe | Me | Me |
| A-69 | H | OEt | OPr | H | H | CSSMe | Me | Me |
| A-70 | H | OEt | OPrⁱ | H | H | CSSMe | Me | Me |
| A-71 | H | OEt | OBu | H | H | CSSMe | Me | Me |
| A-72 | SMe | SMe | H | H | H | CSSMe | Me | Me |
| A-73 | SMe | H | SMe | H | H | CSSMe | Me | Me |
| A-74 | NMe₂ | NMe₂ | H | H | H | CSSMe | Me | Me |
| A-75 | NMe₂ | H | NMe₂ | H | H | CSSMe | Me | Me |

TABLE 42

| | R¹ | R² | R³ | R⁴ | R⁵ | R⁶ | R⁷ | R⁸ |
|---|---|---|---|---|---|---|---|---|
| B-1 | H | H | H | H | H | COSMe | Me | Me |
| B-2 | Cl | H | H | H | H | COSMe | Me | Me |
| B-3 | Br | H | H | H | H | COSMe | Me | Me |
| B-4 | Me | H | H | H | H | COSMe | Me | Me |
| B-5 | Et | H | H | H | H | COSMe | Me | Me |
| B-6 | Bu | H | H | H | H | COSMe | Me | Me |
| B-7 | Buⁱ | H | H | H | H | COSMe | Me | Me |
| B-8 | Buᵗ | H | H | H | H | COSMe | Me | Me |
| B-9 | OEt | H | H | H | H | COSMe | Me | Me |
| B-10 | OPr | H | H | H | H | COSMe | Me | Me |
| B-11 | OCHF₂ | H | H | H | H | COSMe | Me | Me |
| B-12 | OCF₃ | H | H | H | H | COSMe | Me | Me |
| B-13 | CF₃ | H | H | H | H | COSMe | Me | Me |
| B-14 | SMe | H | H | H | H | COSMe | Me | Me |
| B-15 | SEt | H | H | H | H | COSMe | Me | Me |
| B-16 | SPrⁱ | H | H | H | H | COSMe | Me | Me |
| B-17 | NMe₂ | H | H | H | H | COSMe | Me | Me |
| B-18 | NEt₂ | H | H | H | H | COSMe | Me | Me |
| B-19 | H | Cl | H | H | H | COSMe | Me | Me |
| B-20 | H | Br | H | H | H | COSMe | Me | Me |
| B-21 | H | Me | H | H | H | COSMe | Me | Me |
| B-22 | H | Et | H | H | H | COSMe | Me | Me |
| B-23 | H | Pr | H | H | H | COSMe | Me | Me |
| B-24 | H | Bu | H | H | H | COSMe | Me | Me |
| B-25 | H | Buⁱ | H | H | H | COSMe | Me | Me |

TABLE 43

Structure: Phenyl ring with R1-R5 substituents connected via N=C to a thiazine ring with S, N-R6, and R7, R8 substituents.

| | R¹ | R² | R³ | R⁴ | R⁵ | R⁶ | R⁷ | R⁸ |
|---|---|---|---|---|---|---|---|---|
| B-26 | H | Buˢ | H | H | H | COSMe | Me | Me |
| B-27 | H | Buᵗ | H | H | H | COSMe | Me | Me |
| B-28 | H | OMe | H | H | H | COSMe | Me | Me |
| B-29 | H | OEt | H | H | H | COSMe | Me | Me |
| B-30 | H | OPr | H | H | H | COSMe | Me | Me |
| B-31 | H | OCHF₂ | H | H | H | COSMe | Me | Me |
| B-32 | H | OCF₃ | H | H | H | COSMe | Me | Me |
| B-33 | H | CF₃ | H | H | H | COSMe | Me | Me |
| B-34 | H | SMe | H | H | H | COSMe | Me | Me |
| B-35 | H | SEt | H | H | H | COSMe | Me | Me |
| B-36 | H | SPrⁱ | H | H | H | COSMe | Me | Me |
| B-37 | H | NMe₂ | H | H | H | COSMe | Me | Me |
| B-38 | H | NEt₂ | H | H | H | COSMe | Me | Me |
| B-39 | H | H | Cl | H | H | COSMe | Me | Me |
| B-40 | H | H | Br | H | H | COSMe | Me | Me |
| B-41 | H | H | Me | H | H | COSMe | Me | Me |
| B-42 | H | H | Pr | H | H | COSMe | Me | Me |
| B-43 | H | H | Bu | H | H | COSMe | Me | Me |
| B-44 | H | H | Buⁱ | H | H | COSMe | Me | Me |
| B-45 | H | H | Buˢ | H | H | COSMe | Me | Me |
| B-46 | H | H | Buᵗ | H | H | COSMe | Me | Me |
| B-47 | H | H | OMe | H | H | COSMe | Me | Me |
| B-48 | H | H | OEt | H | H | COSMe | Me | Me |
| B-49 | H | H | OPr | H | H | COSMe | Me | Me |
| B-50 | H | H | OCHF₂ | H | H | COSMe | Me | Me |

TABLE 44

| | R¹ | R² | R³ | R⁴ | R⁵ | R⁶ | R⁷ | R⁸ |
|---|---|---|---|---|---|---|---|---|
| B-51 | H | H | OCF₃ | H | H | COSMe | Me | Me |
| B-52 | H | H | CF₃ | H | H | COSMe | Me | Me |
| B-53 | H | H | SMe | H | H | COSMe | Me | Me |
| B-54 | H | H | SEt | H | H | COSMe | Me | Me |
| B-55 | H | H | SPrⁱ | H | H | COSMe | Me | Me |
| B-56 | H | H | NMe₂ | H | H | COSMe | Me | Me |
| B-57 | H | H | NEt₂ | H | H | COSMe | Me | Me |
| B-58 | Me | Me | H | H | H | COSMe | Me | Me |
| B-59 | H | Me | Me | H | H | COSMe | Me | Me |
| B-60 | Et | Et | H | H | H | COSMe | Me | Me |

TABLE 44-continued

| | R¹ | R² | R³ | R⁴ | R⁵ | R⁶ | R⁷ | R⁸ |
|---|---|---|---|---|---|---|---|---|
| B-61 | H | Et | Et | H | H | COSMe | Me | Me |
| B-62 | OMe | Me | H | H | H | COSMe | Me | Me |
| B-63 | OMe | H | Me | H | H | COSMe | Me | Me |
| B-64 | NMe₂ | Me | H | H | H | COSMe | Me | Me |
| B-65 | H | NMe₂ | Me | H | H | COSMe | Me | Me |
| B-66 | Me | NMe₂ | H | H | H | COSMe | Me | Me |
| B-67 | NMe₂ | Cl | H | H | H | COSMe | Me | Me |
| B-68 | Me | NEt₂ | H | H | H | COSMe | Me | Me |
| B-69 | H | NEt₂ | Me | H | H | COSMe | Me | Me |
| B-70 | Prⁱ | H | F | H | H | COSMe | Me | Me |

TABLE 45

| | R¹ | R² | R³ | R⁴ | R⁵ | R⁶ | R⁷ | R⁸ |
|---|---|---|---|---|---|---|---|---|
| C-1 | H | H | H | H | H | CSSEt | Me | Me |
| C-2 | Cl | H | H | H | H | CSSEt | Me | Me |
| C-3 | Br | H | H | H | H | CSSEt | Me | Me |
| C-4 | Me | H | H | H | H | CSSEt | Me | Me |
| C-5 | Et | H | H | H | H | CSSEt | Me | Me |
| C-6 | Pr | H | H | H | H | CSSEt | Me | Me |
| C-7 | Bu | H | H | H | H | CSSEt | Me | Me |
| C-8 | Buⁱ | H | H | H | H | CSSEt | Me | Me |
| C-9 | Buᵗ | H | H | H | H | CSSEt | Me | Me |
| C-10 | OMe | H | H | H | H | CSSEt | Me | Me |
| C-11 | OPr | H | H | H | H | CSSEt | Me | Me |
| C-12 | OCHF₂ | H | H | H | H | CSSEt | Me | Me |
| C-13 | OCF₃ | H | H | H | H | CSSEt | Me | Me |
| C-14 | CF₃ | H | H | H | H | CSSEt | Me | Me |
| C-15 | SEt | H | H | H | H | CSSEt | Me | Me |
| C-16 | SPrⁱ | H | H | H | H | CSSEt | Me | Me |
| C-17 | NEt₂ | H | H | H | H | CSSEt | Me | Me |
| C-18 | H | Cl | H | H | H | CSSEt | Me | Me |
| C-19 | H | Br | H | H | H | CSSEt | Me | Me |
| C-20 | H | Me | H | H | H | CSSEt | Me | Me |
| C-21 | H | Et | H | H | H | CSSEt | Me | Me |
| C-22 | H | Pr | H | H | H | CSSEt | Me | Me |
| C-23 | H | Bu | H | H | H | CSSEt | Me | Me |
| C-24 | H | Buⁱ | H | H | H | CSSEt | Me | Me |
| C-25 | H | Buˢ | H | H | H | CSSEt | Me | Me |

TABLE 46

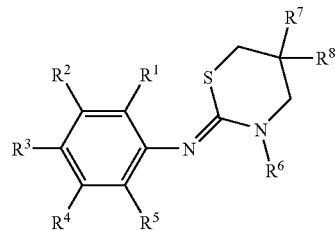

| | R¹ | R² | R³ | R⁴ | R⁵ | R⁶ | R⁷ | R⁸ |
|---|---|---|---|---|---|---|---|---|
| C-26 | H | Buᵗ | H | H | H | CSSEt | Me | Me |
| C-27 | H | OMe | H | H | H | CSSEt | Me | Me |
| C-28 | H | OEt | H | H | H | CSSEt | Me | Me |
| C-29 | H | OPr | H | H | H | CSSEt | Me | Me |
| C-30 | H | OCHF₂ | H | H | H | CSSEt | Me | Me |
| C-31 | H | OCF₃ | H | H | H | CSSEt | Me | Me |
| C-32 | H | CF₃ | H | H | H | CSSEt | Me | Me |
| C-33 | H | SMe | H | H | H | CSSEt | Me | Me |
| C-34 | H | SEt | H | H | H | CSSEt | Me | Me |
| C-35 | H | SPrⁱ | H | H | H | CSSEt | Me | Me |
| C-36 | H | NEt₂ | H | H | H | CSSEt | Me | Me |
| C-37 | H | H | Cl | H | H | CSSEt | Me | Me |
| C-38 | H | H | Br | H | H | CSSEt | Me | Me |
| C-39 | H | H | Me | H | H | CSSEt | Me | Me |
| C-40 | H | H | Et | H | H | CSSEt | Me | Me |
| C-41 | H | H | Pr | H | H | CSSEt | Me | Me |
| C-42 | H | H | Bu | H | H | CSSEt | Me | Me |
| C-43 | H | H | Buⁱ | H | H | CSSEt | Me | Me |
| C-44 | H | H | Buˢ | H | H | CSSEt | Me | Me |
| C-45 | H | H | Buᵗ | H | H | CSSEt | Me | Me |
| C-46 | H | H | OMe | H | H | CSSEt | Me | Me |
| C-47 | H | H | OEt | H | H | CSSEt | Me | Me |
| C-48 | H | H | OPr | H | H | CSSEt | Me | Me |
| C-49 | H | H | OCHF₂ | H | H | CSSEt | Me | Me |
| C-50 | H | H | OCF₃ | H | H | CSSEt | Me | Me |

TABLE 47

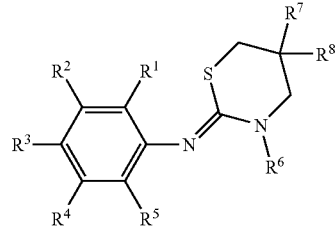

| | R¹ | R² | R³ | R⁴ | R⁵ | R⁶ | R⁷ | R⁸ |
|---|---|---|---|---|---|---|---|---|
| C-51 | H | H | CF₃ | H | H | CSSEt | Me | Me |
| C-52 | H | H | SMe | H | H | CSSEt | Me | Me |
| C-53 | H | H | SEt | H | H | CSSEt | Me | Me |
| C-54 | H | H | SPrⁱ | H | H | CSSEt | Me | Me |
| C-55 | H | H | NMe₂ | H | H | CSSEt | Me | Me |
| C-56 | H | H | NEt₂ | H | H | CSSEt | Me | Me |
| C-57 | Me | Me | H | H | H | CSSEt | Me | Me |
| C-58 | H | Me | Me | H | H | CSSEt | Me | Me |
| C-59 | Et | Et | H | H | H | CSSEt | Me | Me |
| C-60 | H | Et | Et | H | H | CSSEt | Me | Me |
| C-61 | OMe | Me | H | H | H | CSSEt | Me | Me |
| C-62 | OMe | H | Me | H | H | CSSEt | Me | Me |
| C-63 | NMe₂ | Me | H | H | H | CSSEt | Me | Me |

TABLE 47-continued

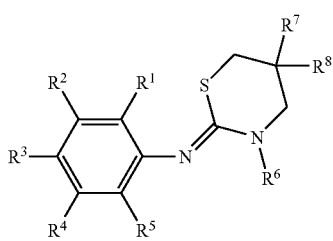

| | R¹ | R² | R³ | R⁴ | R⁵ | R⁶ | R⁷ | R⁸ |
|---|---|---|---|---|---|---|---|---|
| C-64 | H | NMe₂ | Me | H | H | CSSEt | Me | Me |
| C-65 | Me | NMe₂ | H | H | H | CSSEt | Me | Me |
| C-66 | NMe₂ | Cl | H | H | H | CSSEt | Me | Me |
| C-67 | Me | NEt₂ | H | H | H | CSSEt | Me | Me |
| C-68 | H | NEt₂ | Me | H | H | CSSEt | Me | Me |
| C-69 | Prⁱ | H | F | H | H | CSSEt | Me | Me |
| C-70 | OMe | H | OMe | H | H | CSSEt | Me | Me |
| C-71 | H | OMe | OMe | H | H | CSSEt | Me | Me |
| C-72 | H | OMe | OEt | H | H | CSSEt | Me | Me |
| C-73 | H | OEt | OMe | H | H | CSSEt | Me | Me |
| C-74 | H | OEt | OEt | H | H | CSSEt | Me | Me |
| C-75 | OMe | H | Me | H | H | CSSEt | Me | Me |

TABLE 48

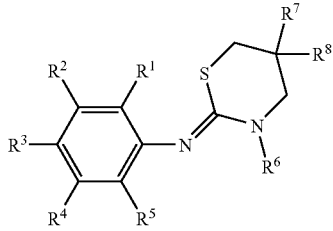

| | R¹ | R² | R³ | R⁴ | R⁵ | R⁶ | R⁷ | R⁸ |
|---|---|---|---|---|---|---|---|---|
| D-1 | Br | H | H | H | H | COSEt | Me | Me |
| D-2 | Buⁱ | H | H | H | H | COSEt | Me | Me |
| D-3 | OPr | H | H | H | H | COSEt | Me | Me |
| D-4 | OCHF₂ | H | H | H | H | COSEt | Me | Me |
| D-5 | OCF₃ | H | H | H | H | COSEt | Me | Me |
| D-6 | NEt₂ | H | H | H | H | COSEt | Me | Me |
| D-7 | H | Cl | H | H | H | COSEt | Me | Me |
| D-8 | H | Br | H | H | H | COSEt | Me | Me |
| D-9 | H | Et | H | H | H | COSEt | Me | Me |
| D-10 | H | Pr | H | H | H | COSEt | Me | Me |
| D-11 | H | Bu | H | H | H | COSEt | Me | Me |
| D-12 | H | Buⁱ | H | H | H | COSEt | Me | Me |
| D-13 | H | Buˢ | H | H | H | COSEt | Me | Me |
| D-14 | H | Buᵗ | H | H | H | COSEt | Me | Me |
| D-15 | H | OEt | H | H | H | COSEt | Me | Me |
| D-16 | H | OPr | H | H | H | COSEt | Me | Me |
| D-17 | H | OCHF₂ | H | H | H | COSEt | Me | Me |
| D-18 | H | OCF₃ | H | H | H | COSEt | Me | Me |
| D-19 | H | CF₃ | H | H | H | COSEt | Me | Me |
| D-20 | H | SMe | H | H | H | COSEt | Me | Me |
| D-21 | H | SEt | H | H | H | COSEt | Me | Me |
| D-22 | H | SPrⁱ | H | H | H | COSEt | Me | Me |
| D-23 | H | NMe₂ | H | H | H | COSEt | Me | Me |
| D-24 | H | NEt₂ | H | H | H | COSEt | Me | Me |
| D-25 | H | H | Br | H | H | COSEt | Me | Me |

TABLE 49

| | R¹ | R² | R³ | R⁴ | R⁵ | R⁶ | R⁷ | R⁸ |
|---|---|---|---|---|---|---|---|---|
| D-26 | H | H | Et | H | H | COSEt | Me | Me |
| D-27 | H | H | Pr | H | H | COSEt | Me | Me |
| D-28 | H | H | Bu | H | H | COSEt | Me | Me |
| D-29 | H | H | Buⁱ | H | H | COSEt | Me | Me |
| D-30 | H | H | Buˢ | H | H | COSEt | Me | Me |
| D-31 | H | H | Buᵗ | H | H | COSEt | Me | Me |
| D-32 | H | H | OMe | H | H | COSEt | Me | Me |
| D-33 | H | H | OEt | H | H | COSEt | Me | Me |
| D-34 | H | H | OPr | H | H | COSEt | Me | Me |
| D-35 | H | H | OCHF₂ | H | H | COSEt | Me | Me |
| D-36 | H | H | OCF₃ | H | H | COSEt | Me | Me |
| D-37 | H | H | CF₃ | H | H | COSEt | Me | Me |
| D-38 | H | H | SMe | H | H | COSEt | Me | Me |
| D-39 | H | H | SEt | H | H | COSEt | Me | Me |
| D-40 | H | H | SPrⁱ | H | H | COSEt | Me | Me |
| D-41 | H | H | NMe₂ | H | H | COSEt | Me | Me |
| D-42 | H | H | NEt₂ | H | H | COSEt | Me | Me |
| D-43 | Et | Et | H | H | H | COSEt | Me | Me |
| D-44 | H | Et | Et | H | H | COSEt | Me | Me |
| D-45 | OMe | Me | H | H | H | COSEt | Me | Me |
| D-46 | OMe | H | Me | H | H | COSEt | Me | Me |
| D-47 | NMe₂ | Me | H | H | H | COSEt | Me | Me |
| D-48 | H | NMe₂ | Me | H | H | COSEt | Me | Me |
| D-49 | H | OEt | OMe | H | H | COSEt | Me | Me |
| D-50 | H | OEt | OEt | H | H | COSEt | Me | Me |

TABLE 50

| | R¹ | R² | R³ | R⁴ | R⁵ | R⁶ | R⁷ | R⁸ |
|---|---|---|---|---|---|---|---|---|
| E-1 | H | H | H | H | H | CSSMe | Et | Et |
| E-2 | Cl | H | H | H | H | CSSMe | Et | Et |
| E-3 | Br | H | H | H | H | CSSMe | Et | Et |
| E-4 | Me | H | H | H | H | CSSMe | Et | Et |
| E-5 | Et | H | H | H | H | CSSMe | Et | Et |
| E-6 | Pr | H | H | H | H | CSSMe | Et | Et |
| E-7 | Bu | H | H | H | H | CSSMe | Et | Et |
| E-8 | Buⁱ | H | H | H | H | CSSMe | Et | Et |
| E-9 | Buᵗ | H | H | H | H | CSSMe | Et | Et |
| E-10 | OMe | H | H | H | H | CSSMe | Et | Et |
| E-11 | OEt | H | H | H | H | CSSMe | Et | Et |
| E-12 | OPrⁱ | H | H | H | H | CSSMe | Et | Et |
| E-13 | OPr | H | H | H | H | CSSMe | Et | Et |
| E-14 | OCHF₂ | H | H | H | H | CSSMe | Et | Et |
| E-15 | OCF₃ | H | H | H | H | CSSMe | Et | Et |
| E-16 | CF₃ | H | H | H | H | CSSMe | Et | Et |
| E-17 | SMe | H | H | H | H | CSSMe | Et | Et |
| E-18 | SEt | H | H | H | H | CSSMe | Et | Et |
| E-19 | SPrⁱ | H | H | H | H | CSSMe | Et | Et |
| E-20 | NMe₂ | H | H | H | H | CSSMe | Et | Et |
| E-21 | NEt₂ | H | H | H | H | CSSMe | Et | Et |
| E-22 | H | Cl | H | H | H | CSSMe | Et | Et |
| E-23 | H | Br | H | H | H | CSSMe | Et | Et |
| E-24 | H | Me | H | H | H | CSSMe | Et | Et |
| E-25 | H | Et | H | H | H | CSSMe | Et | Et |

TABLE 51

| | R¹ | R² | R³ | R⁴ | R⁵ | R⁶ | R⁷ | R⁸ |
|---|---|---|---|---|---|---|---|---|
| E-26 | H | Pr | H | H | H | CSSMe | Et | Et |
| E-27 | H | Prⁱ | H | H | H | CSSMe | Et | Et |
| E-28 | H | Bu | H | H | H | CSSMe | Et | Et |
| E-29 | H | Buⁱ | H | H | H | CSSMe | Et | Et |
| E-30 | H | Buˢ | H | H | H | CSSMe | Et | Et |
| E-31 | H | Buᵗ | H | H | H | CSSMe | Et | Et |
| E-32 | H | OMe | H | H | H | CSSMe | Et | Et |
| E-33 | H | OEt | H | H | H | CSSMe | Et | Et |
| E-34 | H | OPr | H | H | H | CSSMe | Et | Et |
| E-35 | H | OPrⁱ | H | H | H | CSSMe | Et | Et |
| E-36 | H | OCHF₂ | H | H | H | CSSMe | Et | Et |
| E-37 | H | OCF₃ | H | H | H | CSSMe | Et | Et |
| E-38 | H | CF₃ | H | H | H | CSSMe | Et | Et |
| E-39 | H | SMe | H | H | H | CSSMe | Et | Et |
| E-40 | H | SEt | H | H | H | CSSMe | Et | Et |
| E-41 | H | SPrⁱ | H | H | H | CSSMe | Et | Et |
| E-42 | H | NMe₂ | H | H | H | CSSMe | Et | Et |
| E-43 | H | NEt₂ | H | H | H | CSSMe | Et | Et |
| E-44 | H | H | Cl | H | H | CSSMe | Et | Et |
| E-45 | H | H | Br | H | H | CSSMe | Et | Et |
| E-46 | H | H | Me | H | H | CSSMe | Et | Et |
| E-47 | H | H | Et | H | H | CSSMe | Et | Et |
| E-48 | H | H | Pr | H | H | CSSMe | Et | Et |
| E-49 | H | H | Prⁱ | H | H | CSSMe | Et | Et |
| E-50 | H | H | Bu | H | H | CSSMe | Et | Et |

TABLE 52

|  | R¹ | R² | R³ | R⁴ | R⁵ | R⁶ | R⁷ | R⁸ |
|---|---|---|---|---|---|---|---|---|
| E-51 | H | H | Buⁱ | H | H | CSSMe | Et | Et |
| E-52 | H | H | Buˢ | H | H | CSSMe | Et | Et |
| E-53 | H | H | Buᵗ | H | H | CSSMe | Et | Et |
| E-54 | H | H | OMe | H | H | CSSMe | Et | Et |
| E-55 | H | H | OEt | H | H | CSSMe | Et | Et |
| E-56 | H | H | OPr | H | H | CSSMe | Et | Et |
| E-57 | H | H | OPrⁱ | H | H | CSSMe | Et | Et |
| E-58 | H | H | OCHF₂ | H | H | CSSMe | Et | Et |
| E-59 | H | H | OCF₃ | H | H | CSSMe | Et | Et |
| E-60 | H | H | CF₃ | H | H | CSSMe | Et | Et |
| E-61 | H | H | SMe | H | H | CSSMe | Et | Et |
| E-62 | H | H | SEt | H | H | CSSMe | Et | Et |
| E-63 | H | H | SPrⁱ | H | H | CSSMe | Et | Et |
| E-64 | H | H | NMe₂ | H | H | CSSMe | Et | Et |
| E-65 | H | H | NEt₂ | H | H | CSSMe | Et | Et |
| E-66 | Me | NMe₂ | H | H | H | CSSMe | Et | Et |
| E-67 | NMe₂ | Cl | H | H | H | CSSMe | Et | Et |
| E-68 | Me | NEt₂ | H | H | H | CSSMe | Et | Et |
| E-69 | H | NEt₂ | Me | H | H | CSSMe | Et | Et |
| E-70 | Prⁱ | H | F | H | H | CSSMe | Et | Et |
| E-71 | OMe | H | OMe | H | H | CSSMe | Et | Et |
| E-72 | H | OMe | OMe | H | H | CSSMe | Et | Et |
| E-73 | H | OMe | OEt | H | H | CSSMe | Et | Et |
| E-74 | H | OEt | OMe | H | H | CSSMe | Et | Et |
| E-75 | H | OEt | OEt | H | H | CSSMe | Et | Et |

TABLE 53

|  | R¹ | R² | R³ | R⁴ | R⁵ | R⁶ | R⁷ | R⁸ |
|---|---|---|---|---|---|---|---|---|
| F-1 | H | H | H | H | H | CSSMe | Pr | Pr |
| F-2 | Cl | H | H | H | H | CSSMe | Pr | Pr |
| F-3 | Br | H | H | H | H | CSSMe | Pr | Pr |
| F-4 | Me | H | H | H | H | CSSMe | Pr | Pr |
| F-5 | Et | H | H | H | H | CSSMe | Pr | Pr |
| F-6 | Pr | H | H | H | H | CSSMe | Pr | Pr |
| F-7 | Bu | H | H | H | H | CSSMe | Pr | Pr |
| F-8 | Buⁱ | H | H | H | H | CSSMe | Pr | Pr |
| F-9 | Buᵗ | H | H | H | H | CSSMe | Pr | Pr |
| F-10 | OMe | H | H | H | H | CSSMe | Pr | Pr |
| F-11 | OEt | H | H | H | H | CSSMe | Pr | Pr |
| F-12 | OPrⁱ | H | H | H | H | CSSMe | Pr | Pr |
| F-13 | OPr | H | H | H | H | CSSMe | Pr | Pr |

TABLE 53-continued

|  | R¹ | R² | R³ | R⁴ | R⁵ | R⁶ | R⁷ | R⁸ |
|---|---|---|---|---|---|---|---|---|
| F-14 | OCHF₂ | H | H | H | H | CSSMe | Pr | Pr |
| F-15 | OCF₃ | H | H | H | H | CSSMe | Pr | Pr |
| F-16 | CF₃ | H | H | H | H | CSSMe | Pr | Pr |
| F-17 | SMe | H | H | H | H | CSSMe | Pr | Pr |
| F-18 | SEt | H | H | H | H | CSSMe | Pr | Pr |
| F-19 | SPrⁱ | H | H | H | H | CSSMe | Pr | Pr |
| F-20 | NMe₂ | H | H | H | H | CSSMe | Pr | Pr |
| F-21 | NEt₂ | H | H | H | H | CSSMe | Pr | Pr |
| F-22 | H | Cl | H | H | H | CSSMe | Pr | Pr |
| F-23 | H | Br | H | H | H | CSSMe | Pr | Pr |
| F-24 | H | Me | H | H | H | CSSMe | Pr | Pr |
| F-25 | H | Et | H | H | H | CSSMe | Pr | Pr |

TABLE 54

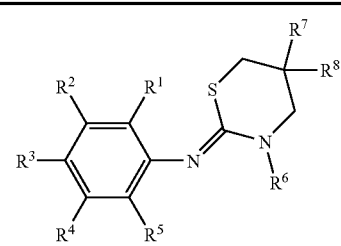

|  | R¹ | R² | R³ | R⁴ | R⁵ | R⁶ | R⁷ | R⁸ |
|---|---|---|---|---|---|---|---|---|
| F-26 | H | Pr | H | H | H | CSSMe | Pr | Pr |
| F-27 | H | Prⁱ | H | H | H | CSSMe | Pr | Pr |
| F-28 | H | Bu | H | H | H | CSSMe | Pr | Pr |
| F-29 | H | Buⁱ | H | H | H | CSSMe | Pr | Pr |
| F-30 | H | Buˢ | H | H | H | CSSMe | Pr | Pr |
| F-31 | H | Buᵗ | H | H | H | CSSMe | Pr | Pr |
| F-32 | H | OMe | H | H | H | CSSMe | Pr | Pr |
| F-33 | H | OEt | H | H | H | CSSMe | Pr | Pr |
| F-34 | H | OPr | H | H | H | CSSMe | Pr | Pr |
| F-35 | H | OPrⁱ | H | H | H | CSSMe | Pr | Pr |
| F-36 | H | OCHF₂ | H | H | H | CSSMe | Pr | Pr |
| F-37 | H | OCF₃ | H | H | H | CSSMe | Pr | Pr |
| F-38 | H | CF₃ | H | H | H | CSSMe | Pr | Pr |
| F-39 | H | SMe | H | H | H | CSSMe | Pr | Pr |
| F-40 | H | SEt | H | H | H | CSSMe | Pr | Pr |
| F-41 | H | SPrⁱ | H | H | H | CSSMe | Pr | Pr |
| F-42 | H | NMe₂ | H | H | H | CSSMe | Pr | Pr |
| F-43 | H | NEt₂ | H | H | H | CSSMe | Pr | Pr |
| F-44 | H | H | Cl | H | H | CSSMe | Pr | Pr |
| F-45 | H | H | Br | H | H | CSSMe | Pr | Pr |
| F-46 | H | H | Me | H | H | CSSMe | Pr | Pr |
| F-47 | H | H | Et | H | H | CSSMe | Pr | Pr |
| F-48 | H | H | Pr | H | H | CSSMe | Pr | Pr |
| F-49 | H | H | Prⁱ | H | H | CSSMe | Pr | Pr |
| F-50 | H | H | Bu | H | H | CSSMe | Pr | Pr |

TABLE 55

| | R¹ | R² | R³ | R⁴ | R⁵ | R⁶ | R⁷ | R⁸ |
|---|---|---|---|---|---|---|---|---|
| F-51 | H | H | Buⁱ | H | H | CSSMe | Pr | Pr |
| F-52 | H | H | Buˢ | H | H | CSSMe | Pr | Pr |
| F-53 | H | H | Buᵗ | H | H | CSSMe | Pr | Pr |
| F-54 | H | H | OMe | H | H | CSSMe | Pr | Pr |
| F-55 | H | H | OEt | H | H | CSSMe | Pr | Pr |
| F-56 | H | H | OPr | H | H | CSSMe | Pr | Pr |
| F-57 | H | H | OPrⁱ | H | H | CSSMe | Pr | Pr |
| F-58 | H | H | OCHF₂ | H | H | CSSMe | Pr | Pr |
| F-59 | H | H | OCF₃ | H | H | CSSMe | Pr | Pr |
| F-60 | H | H | CF₃ | H | H | CSSMe | Pr | Pr |
| F-61 | H | H | SMe | H | H | CSSMe | Pr | Pr |
| F-62 | H | H | SEt | H | H | CSSMe | Pr | Pr |
| F-63 | H | H | SPrⁱ | H | H | CSSMe | Pr | Pr |
| F-64 | H | H | NMe₂ | H | H | CSSMe | Pr | Pr |
| F-65 | H | H | NEt₂ | H | H | CSSMe | Pr | Pr |
| F-66 | Me | NMe₂ | H | H | H | CSSMe | Pr | Pr |
| F-67 | NMe₂ | Cl | H | H | H | CSSMe | Pr | Pr |
| F-68 | Me | NEt₂ | H | H | H | CSSMe | Pr | Pr |
| F-69 | H | NEt₂ | Me | H | H | CSSMe | Pr | Pr |
| F-70 | Buˢ | H | H | H | H | CSSMe | Pr | Pr |
| F-71 | OMe | H | OMe | H | H | CSSMe | Pr | Pr |
| F-72 | H | OMe | OMe | H | H | CSSMe | Pr | Pr |
| F-73 | H | OMe | OEt | H | H | CSSMe | Pr | Pr |
| F-74 | H | OEt | OMe | H | H | CSSMe | Pr | Pr |
| F-75 | H | OEt | OEt | H | H | CSSMe | Pr | Pr |

TABLE 56

| | R¹ | R² | R³ | R⁴ | R⁵ | R⁶ | R⁷ | R⁸ |
|---|---|---|---|---|---|---|---|---|
| G-1 | H | H | H | H | H | CSSEt | Et | Et |
| G-2 | Cl | H | H | H | H | CSSEt | Et | Et |
| G-3 | Br | H | H | H | H | CSSEt | Et | Et |
| G-4 | Me | H | H | H | H | CSSEt | Et | Et |
| G-5 | Et | H | H | H | H | CSSEt | Et | Et |
| G-6 | Pr | H | H | H | H | CSSEt | Et | Et |
| G-7 | Bu | H | H | H | H | CSSEt | Et | Et |
| G-8 | Buⁱ | H | H | H | H | CSSEt | Et | Et |
| G-9 | Buᵗ | H | H | H | H | CSSEt | Et | Et |
| G-10 | OMe | H | H | H | H | CSSEt | Et | Et |
| G-11 | OEt | H | H | H | H | CSSEt | Et | Et |
| G-12 | OPrⁱ | H | H | H | H | CSSEt | Et | Et |
| G-13 | OPr | H | H | H | H | CSSEt | Et | Et |
| G-14 | OCHF₂ | H | H | H | H | CSSEt | Et | Et |

TABLE 56-continued

| | R¹ | R² | R³ | R⁴ | R⁵ | R⁶ | R⁷ | R⁸ |
|---|---|---|---|---|---|---|---|---|
| G-15 | OCF₃ | H | H | H | H | CSSEt | Et | Et |
| G-16 | CF₃ | H | H | H | H | CSSEt | Et | Et |
| G-17 | SMe | H | H | H | H | CSSEt | Et | Et |
| G-18 | SEt | H | H | H | H | CSSEt | Et | Et |
| G-19 | SPrⁱ | H | H | H | H | CSSEt | Et | Et |
| G-20 | NMe₂ | H | H | H | H | CSSEt | Et | Et |
| G-21 | NEt₂ | H | H | H | H | CSSEt | Et | Et |
| G-22 | H | Cl | H | H | H | CSSEt | Et | Et |
| G-23 | H | Br | H | H | H | CSSEt | Et | Et |
| G-24 | H | Me | H | H | H | CSSEt | Et | Et |
| G-25 | H | Et | H | H | H | CSSEt | Et | Et |

TABLE 57

| | R¹ | R² | R³ | R⁴ | R⁵ | R⁶ | R⁷ | R⁸ |
|---|---|---|---|---|---|---|---|---|
| G-26 | H | Pr | H | H | H | CSSEt | Et | Et |
| G-27 | H | Prⁱ | H | H | H | CSSEt | Et | Et |
| G-28 | H | Bu | H | H | H | CSSEt | Et | Et |
| G-29 | H | Buⁱ | H | H | H | CSSEt | Et | Et |
| G-30 | H | Buˢ | H | H | H | CSSEt | Et | Et |
| G-31 | H | Buᵗ | H | H | H | CSSEt | Et | Et |
| G-32 | H | OMe | H | H | H | CSSEt | Et | Et |
| G-33 | H | OEt | H | H | H | CSSEt | Et | Et |
| G-34 | H | OPr | H | H | H | CSSEt | Et | Et |
| G-35 | H | OPrⁱ | H | H | H | CSSEt | Et | Et |
| G-36 | H | OCHF₂ | H | H | H | CSSEt | Et | Et |
| G-37 | H | OCF₃ | H | H | H | CSSEt | Et | Et |
| G-38 | H | CF₃ | H | H | H | CSSEt | Et | Et |
| G-39 | H | SMe | H | H | H | CSSEt | Et | Et |
| G-40 | H | SEt | H | H | H | CSSEt | Et | Et |
| G-41 | H | SPrⁱ | H | H | H | CSSEt | Et | Et |
| G-42 | H | NMe₂ | H | H | H | CSSEt | Et | Et |
| G-43 | H | NEt₂ | H | H | H | CSSEt | Et | Et |
| G-44 | H | H | Cl | H | H | CSSEt | Et | Et |
| G-45 | H | H | Br | H | H | CSSEt | Et | Et |
| G-46 | H | H | Me | H | H | CSSEt | Et | Et |
| G-47 | H | H | Et | H | H | CSSEt | Et | Et |
| G-48 | H | H | Pr | H | H | CSSEt | Et | Et |
| G-49 | H | H | Prⁱ | H | H | CSSEt | Et | Et |
| G-50 | H | H | Bu | H | H | CSSEt | Et | Et |

TABLE 58

|  | R¹ | R² | R³ | R⁴ | R⁵ | R⁶ | R⁷ | R⁸ |
|---|---|---|---|---|---|---|---|---|
| G-51 | H | H | Buⁱ | H | H | CSSEt | Et | Et |
| G-52 | H | H | Buˢ | H | H | CSSEt | Et | Et |
| G-53 | H | H | Buᵗ | H | H | CSSEt | Et | Et |
| G-54 | H | H | OMe | H | H | CSSEt | Et | Et |
| G-55 | H | H | OEt | H | H | CSSEt | Et | Et |
| G-56 | H | H | OPr | H | H | CSSEt | Et | Et |
| G-57 | H | H | OPrⁱ | H | H | CSSEt | Et | Et |
| G-58 | H | H | OCHF₂ | H | H | CSSEt | Et | Et |
| G-59 | H | H | OCF₃ | H | H | CSSEt | Et | Et |
| G-60 | H | H | CF₃ | H | H | CSSEt | Et | Et |
| G-61 | H | H | SMe | H | H | CSSEt | Et | Et |
| G-62 | H | H | SEt | H | H | CSSEt | Et | Et |
| G-63 | H | H | SPrⁱ | H | H | CSSEt | Et | Et |
| G-64 | H | H | NMe₂ | H | H | CSSEt | Et | Et |
| G-65 | H | H | NEt₂ | H | H | CSSEt | Et | Et |
| G-66 | Me | NMe₂ | H | H | H | CSSEt | Et | Et |
| G-67 | NMe₂ | Cl | H | H | H | CSSEt | Et | Et |
| G-68 | Me | NEt₂ | H | H | H | CSSEt | Et | Et |
| G-69 | H | NEt₂ | Me | H | H | CSSEt | Et | Et |
| G-70 | Buˢ | H | H | H | H | CSSEt | Et | Et |
| G-71 | OMe | H | OMe | H | H | CSSEt | Et | Et |
| G-72 | H | OMe | OMe | H | H | CSSEt | Et | Et |
| G-73 | H | OMe | OEt | H | H | CSSEt | Et | Et |
| G-74 | H | OEt | OMe | H | H | CSSEt | Et | Et |
| G-75 | H | OEt | OEt | H | H | CSSEt | Et | Et |

TABLE 59

|  | R¹ | R² | R³ | R⁴ | R⁵ | R⁶ | R⁷ | R⁸ |
|---|---|---|---|---|---|---|---|---|
| H-1 | H | H | H | H | H | CSSMe | —(CH₂)₂— | |
| H-2 | Cl | H | H | H | H | CSSMe | —(CH₂)₂— | |
| H-3 | Br | H | H | H | H | CSSMe | —(CH₂)₂— | |
| H-4 | Me | H | H | H | H | CSSMe | —(CH₂)₂— | |
| H-5 | Et | H | H | H | H | CSSMe | —(CH₂)₂— | |
| H-6 | Pr | H | H | H | H | CSSMe | —(CH₂)₂— | |
| H-7 | Bu | H | H | H | H | CSSMe | —(CH₂)₂— | |
| H-8 | Buⁱ | H | H | H | H | CSSMe | —(CH₂)₂— | |
| H-9 | Buᵗ | H | H | H | H | CSSMe | —(CH₂)₂— | |
| H-10 | OMe | H | H | H | H | CSSMe | —(CH₂)₂— | |
| H-11 | OEt | H | H | H | H | CSSMe | —(CH₂)₂— | |
| H-12 | OPrⁱ | H | H | H | H | CSSMe | —(CH₂)₂— | |
| H-13 | OPr | H | H | H | H | CSSMe | —(CH₂)₂— | |
| H-14 | OCHF₂ | H | H | H | H | CSSMe | —(CH₂)₂— | |
| H-15 | OCF₃ | H | H | H | H | CSSMe | —(CH₂)₂— | |
| H-16 | CF₃ | H | H | H | H | CSSMe | —(CH₂)₂— | |
| H-17 | SMe | H | H | H | H | CSSMe | —(CH₂)₂— | |
| H-18 | SEt | H | H | H | H | CSSMe | —(CH₂)₂— | |
| H-19 | SPrⁱ | H | H | H | H | CSSMe | —(CH₂)₂— | |
| H-20 | NMe₂ | H | H | H | H | CSSMe | —(CH₂)₂— | |
| H-21 | NEt₂ | H | H | H | H | CSSMe | —(CH₂)₂— | |
| H-22 | H | Cl | H | H | H | CSSMe | —(CH₂)₂— | |
| H-23 | H | Br | H | H | H | CSSMe | —(CH₂)₂— | |
| H-24 | H | Me | H | H | H | CSSMe | —(CH₂)₂— | |
| H-25 | H | Et | H | H | H | CSSMe | —(CH₂)₂— | |

TABLE 60

|  | R¹ | R² | R³ | R⁴ | R⁵ | R⁶ | R⁷ | R⁸ |
|---|---|---|---|---|---|---|---|---|
| H-26 | H | Pr | H | H | H | CSSMe | —(CH₂)₂— | |
| H-27 | H | Prⁱ | H | H | H | CSSMe | —(CH₂)₂— | |
| H-28 | H | Bu | H | H | H | CSSMe | —(CH₂)₂— | |
| H-29 | H | Buⁱ | H | H | H | CSSMe | —(CH₂)₂— | |
| H-30 | H | Buˢ | H | H | H | CSSMe | —(CH₂)₂— | |
| H-31 | H | Buᵗ | H | H | H | CSSMe | —(CH₂)₂— | |
| H-32 | H | OMe | H | H | H | CSSMe | —(CH₂)₂— | |
| H-33 | H | OEt | H | H | H | CSSMe | —(CH₂)₂— | |
| H-34 | H | OPr | H | H | H | CSSMe | —(CH₂)₂— | |
| H-35 | H | OPrⁱ | H | H | H | CSSMe | —(CH₂)₂— | |
| H-36 | H | OCHF₂ | H | H | H | CSSMe | —(CH₂)₂— | |
| H-37 | H | OCF₃ | H | H | H | CSSMe | —(CH₂)₂— | |
| H-38 | H | CF₃ | H | H | H | CSSMe | —(CH₂)₂— | |
| H-39 | H | SMe | H | H | H | CSSMe | —(CH₂)₂— | |
| H-40 | H | SEt | H | H | H | CSSMe | —(CH₂)₂— | |
| H-41 | H | SPrⁱ | H | H | H | CSSMe | —(CH₂)₂— | |
| H-42 | H | NMe₂ | H | H | H | CSSMe | —(CH₂)₂— | |
| H-43 | H | NEt₂ | H | H | H | CSSMe | —(CH₂)₂— | |
| H-44 | H | H | Cl | H | H | CSSMe | —(CH₂)₂— | |
| H-45 | H | H | Br | H | H | CSSMe | —(CH₂)₂— | |
| H-46 | H | H | Me | H | H | CSSMe | —(CH₂)₂— | |
| H-47 | H | H | Et | H | H | CSSMe | —(CH₂)₂— | |
| H-48 | H | H | Pr | H | H | CSSMe | —(CH₂)₂— | |
| H-49 | H | H | Prⁱ | H | H | CSSMe | —(CH₂)₂— | |
| H-50 | H | H | Bu | H | H | CSSMe | —(CH₂)₂— | |

TABLE 61

|  | R¹ | R² | R³ | R⁴ | R⁵ | R⁶ | R⁷ | R⁸ |
|---|---|---|---|---|---|---|---|---|
| H-51 | H | H | Buⁱ | H | H | CSSMe | —(CH₂)₂— | |
| H-52 | H | H | Buˢ | H | H | CSSMe | —(CH₂)₂— | |
| H-53 | H | H | Buᵗ | H | H | CSSMe | —(CH₂)₂— | |
| H-54 | H | H | OMe | H | H | CSSMe | —(CH₂)₂— | |
| H-55 | H | H | OEt | H | H | CSSMe | —(CH₂)₂— | |
| H-56 | H | H | OPr | H | H | CSSMe | —(CH₂)₂— | |
| H-57 | H | H | OPrⁱ | H | H | CSSMe | —(CH₂)₂— | |
| H-58 | H | H | OCHF₂ | H | H | CSSMe | —(CH₂)₂— | |
| H-59 | H | H | OCF₃ | H | H | CSSMe | —(CH₂)₂— | |
| H-60 | H | H | CF₃ | H | H | CSSMe | —(CH₂)₂— | |
| H-61 | H | H | SMe | H | H | CSSMe | —(CH₂)₂— | |
| H-62 | H | H | SEt | H | H | CSSMe | —(CH₂)₂— | |
| H-63 | H | H | SPrⁱ | H | H | CSSMe | —(CH₂)₂— | |
| H-64 | H | H | NMe₂ | H | H | CSSMe | —(CH₂)₂— | |
| H-65 | H | H | NEt₂ | H | H | CSSMe | —(CH₂)₂— | |
| H-66 | Me | NMe₂ | H | H | H | CSSMe | —(CH₂)₂— | |
| H-67 | NMe₂ | Cl | H | H | H | CSSMe | —(CH₂)₂— | |
| H-68 | Me | NEt₂ | H | H | H | CSSMe | —(CH₂)₂— | |
| H-69 | H | NEt₂ | Me | H | H | CSSMe | —(CH₂)₂— | |
| H-70 | Buˢ | H | H | H | H | CSSMe | —(CH₂)₂— | |
| H-71 | OMe | H | OMe | H | H | CSSMe | —(CH₂)₂— | |
| H-72 | H | OMe | OMe | H | H | CSSMe | —(CH₂)₂— | |
| H-73 | H | OMe | OEt | H | H | CSSMe | —(CH₂)₂— | |
| H-74 | H | OEt | OMe | H | H | CSSMe | —(CH₂)₂— | |
| H-75 | H | OEt | OEt | H | H | CSSMe | —(CH₂)₂— | |

TABLE 62

|  | R¹ | R² | R³ | R⁴ | R⁵ | R⁶ | R⁷ | R⁸ |
|---|---|---|---|---|---|---|---|---|
| N-1 | H | H | H | H | H | CSSMe | —(CH₂)₄— | |
| N-2 | Cl | H | H | H | H | CSSMe | —(CH₂)₄— | |
| N-3 | Br | H | H | H | H | CSSMe | —(CH₂)₄— | |
| N-4 | Me | H | H | H | H | CSSMe | —(CH₂)₄— | |
| N-5 | Et | H | H | H | H | CSSMe | —(CH₂)₄— | |
| N-6 | Pr | H | H | H | H | CSSMe | —(CH₂)₄— | |
| N-7 | Bu | H | H | H | H | CSSMe | —(CH₂)₄— | |
| N-8 | Buⁱ | H | H | H | H | CSSMe | —(CH₂)₄— | |
| N-9 | Buᵗ | H | H | H | H | CSSMe | —(CH₂)₄— | |
| N-10 | OMe | H | H | H | H | CSSMe | —(CH₂)₄— | |
| N-11 | OEt | H | H | H | H | CSSMe | —(CH₂)₄— | |
| N-12 | OPrⁱ | H | H | H | H | CSSMe | —(CH₂)₄— | |
| N-13 | OPr | H | H | H | H | CSSMe | —(CH₂)₄— | |
| N-14 | OCHF₂ | H | H | H | H | CSSMe | —(CH₂)₄— | |

TABLE 62-continued

|  | R¹ | R² | R³ | R⁴ | R⁵ | R⁶ | R⁷ | R⁸ |
|---|---|---|---|---|---|---|---|---|
| N-15 | OCF₃ | H | H | H | H | CSSMe | —(CH₂)₄— | |
| N-16 | CF₃ | H | H | H | H | CSSMe | —(CH₂)₄— | |
| N-17 | SMe | H | H | H | H | CSSMe | —(CH₂)₄— | |
| N-18 | SEt | H | H | H | H | CSSMe | —(CH₂)₄— | |
| N-19 | SPrⁱ | H | H | H | H | CSSMe | —(CH₂)₄— | |
| N-20 | NMe₂ | H | H | H | H | CSSMe | —(CH₂)₄— | |
| N-21 | NEt₂ | H | H | H | H | CSSMe | —(CH₂)₄— | |
| N-22 | H | Cl | H | H | H | CSSMe | —(CH₂)₄— | |
| N-23 | H | Br | H | H | H | CSSMe | —(CH₂)₄— | |
| N-24 | H | Me | H | H | H | CSSMe | —(CH₂)₄— | |
| N-25 | H | Et | H | H | H | CSSMe | —(CH₂)₄— | |

TABLE 63

|  | R¹ | R² | R³ | R⁴ | R⁵ | R⁶ | R⁷ | R⁸ |
|---|---|---|---|---|---|---|---|---|
| N-26 | H | Pr | H | H | H | CSSMe | —(CH₂)₄— | |
| N-27 | H | Prⁱ | H | H | H | CSSMe | —(CH₂)₄— | |
| N-28 | H | Bu | H | H | H | CSSMe | —(CH₂)₄— | |
| N-29 | H | Buⁱ | H | H | H | CSSMe | —(CH₂)₄— | |
| N-30 | H | Buˢ | H | H | H | CSSMe | —(CH₂)₄— | |
| N-31 | H | Buᵗ | H | H | H | CSSMe | —(CH₂)₄— | |
| N-32 | H | OMe | H | H | H | CSSMe | —(CH₂)₄— | |
| N-33 | H | OEt | H | H | H | CSSMe | —(CH₂)₄— | |
| N-34 | H | OPr | H | H | H | CSSMe | —(CH₂)₄— | |
| N-35 | H | OPrⁱ | H | H | H | CSSMe | —(CH₂)₄— | |
| N-36 | H | OCHF₂ | H | H | H | CSSMe | —(CH₂)₄— | |
| N-37 | H | OCF₃ | H | H | H | CSSMe | —(CH₂)₄— | |
| N-38 | H | CF₃ | H | H | H | CSSMe | —(CH₂)₄— | |
| N-39 | H | SMe | H | H | H | CSSMe | —(CH₂)₄— | |
| N-40 | H | SEt | H | H | H | CSSMe | —(CH₂)₄— | |
| N-41 | H | SPrⁱ | H | H | H | CSSMe | —(CH₂)₄— | |
| N-42 | H | NMe₂ | H | H | H | CSSMe | —(CH₂)₄— | |
| N-43 | H | NEt₂ | H | H | H | CSSMe | —(CH₂)₄— | |
| N-44 | H | H | Cl | H | H | CSSMe | —(CH₂)₄— | |
| N-45 | H | H | Br | H | H | CSSMe | —(CH₂)₄— | |
| N-46 | H | H | Me | H | H | CSSMe | —(CH₂)₄— | |
| N-47 | H | H | Et | H | H | CSSMe | —(CH₂)₄— | |
| N-48 | H | H | Pr | H | H | CSSMe | —(CH₂)₄— | |
| N-49 | H | H | Prⁱ | H | H | CSSMe | —(CH₂)₄— | |
| N-50 | H | H | Bu | H | H | CSSMe | —(CH₂)₄— | |

TABLE 64

| | R¹ | R² | R³ | R⁴ | R⁵ | R⁶ | R⁷ | R⁸ |
|---|---|---|---|---|---|---|---|---|
| N-51 | H | H | Buⁱ | H | H | CSSMe | —(CH₂)₄— | |
| N-52 | H | H | Buˢ | H | H | CSSMe | —(CH₂)₄— | |
| N-53 | H | H | Buᵗ | H | H | CSSMe | —(CH₂)₄— | |
| N-54 | H | H | OMe | H | H | CSSMe | —(CH₂)₄— | |
| N-55 | H | H | OEt | H | H | CSSMe | —(CH₂)₄— | |
| N-56 | H | H | OPr | H | H | CSSMe | —(CH₂)₄— | |
| N-57 | H | H | OPrⁱ | H | H | CSSMe | —(CH₂)₄— | |
| N-58 | H | H | OCHF₂ | H | H | CSSMe | —(CH₂)₄— | |
| N-59 | H | H | OCF₃ | H | H | CSSMe | —(CH₂)₄— | |
| N-60 | H | H | CF₃ | H | H | CSSMe | —(CH₂)₄— | |
| N-61 | H | H | SMe | H | H | CSSMe | —(CH₂)₄— | |
| N-62 | H | H | SEt | H | H | CSSMe | —(CH₂)₄— | |
| N-63 | H | H | SPrⁱ | H | H | CSSMe | —(CH₂)₄— | |
| N-64 | H | H | NMe₂ | H | H | CSSMe | —(CH₂)₄— | |
| N-65 | H | H | NEt₂ | H | H | CSSMe | —(CH₂)₄— | |
| N-66 | Me | NMe₂ | H | H | H | CSSMe | —(CH₂)₄— | |
| N-67 | NMe₂ | Cl | H | H | H | CSSMe | —(CH₂)₄— | |
| N-68 | Me | NEt₂ | H | H | H | CSSMe | —(CH₂)₄— | |
| N-69 | H | NEt₂ | Me | H | H | CSSMe | —(CH₂)₄— | |
| N-70 | Buˢ | H | H | H | H | CSSMe | —(CH₂)₄— | |
| N-71 | OMe | H | OMe | H | H | CSSMe | —(CH₂)₄— | |
| N-72 | H | OMe | OMe | H | H | CSSMe | —(CH₂)₄— | |
| N-73 | H | OMe | OEt | H | H | CSSMe | —(CH₂)₄— | |
| N-74 | H | OEt | OMe | H | H | CSSMe | —(CH₂)₄— | |
| N-75 | H | OEt | OEt | H | H | CSSMe | —(CH₂)₄— | |

TABLE 65

| | R¹ | R² | R³ | R⁴ | R⁵ | R⁶ | R⁷ | R⁸ |
|---|---|---|---|---|---|---|---|---|
| J-1 | H | H | H | H | H | CSSMe | —(CH₂)₅— | |
| J-2 | Cl | H | H | H | H | CSSMe | —(CH₂)₅— | |
| J-3 | Br | H | H | H | H | CSSMe | —(CH₂)₅— | |
| J-4 | Me | H | H | H | H | CSSMe | —(CH₂)₅— | |
| J-5 | Et | H | H | H | H | CSSMe | —(CH₂)₅— | |
| J-6 | Pr | H | H | H | H | CSSMe | —(CH₂)₅— | |
| J-7 | Bu | H | H | H | H | CSSMe | —(CH₂)₅— | |
| J-8 | Buⁱ | H | H | H | H | CSSMe | —(CH₂)₅— | |
| J-9 | Buᵗ | H | H | H | H | CSSMe | —(CH₂)₅— | |
| J-10 | OMe | H | H | H | H | CSSMe | —(CH₂)₅— | |
| J-11 | OEt | H | H | H | H | CSSMe | —(CH₂)₅— | |
| J-12 | OPrⁱ | H | H | H | H | CSSMe | —(CH₂)₅— | |
| J-13 | OPr | H | H | H | H | CSSMe | —(CH₂)₅— | |
| J-14 | OCHF₂ | H | H | H | H | CSSMe | —(CH₂)₅— | |
| J-15 | OCF₃ | H | H | H | H | CSSMe | —(CH₂)₅— | |
| J-16 | CF₃ | H | H | H | H | CSSMe | —(CH₂)₅— | |
| J-17 | SMe | H | H | H | H | CSSMe | —(CH₂)₅— | |
| J-18 | SEt | H | H | H | H | CSSMe | —(CH₂)₅— | |
| J-19 | SPrⁱ | H | H | H | H | CSSMe | —(CH₂)₅— | |
| J-20 | NMe₂ | H | H | H | H | CSSMe | —(CH₂)₅— | |
| J-21 | NEt₂ | H | H | H | H | CSSMe | —(CH₂)₅— | |
| J-22 | H | Cl | H | H | H | CSSMe | —(CH₂)₅— | |
| J-23 | H | Br | H | H | H | CSSMe | —(CH₂)₅— | |
| J-24 | H | Me | H | H | H | CSSMe | —(CH₂)₅— | |
| J-25 | H | Et | H | H | H | CSSMe | —(CH₂)₅— | |

TABLE 66

| | R¹ | R² | R³ | R⁴ | R⁵ | R⁶ | R⁷ | R⁸ |
|---|---|---|---|---|---|---|---|---|
| J-26 | H | Pr | H | H | H | CSSMe | —(CH₂)₅— | |
| J-27 | H | Prⁱ | H | H | H | CSSMe | —(CH₂)₅— | |
| J-28 | H | Bu | H | H | H | CSSMe | —(CH₂)₅— | |
| J-29 | H | Buⁱ | H | H | H | CSSMe | —(CH₂)₅— | |
| J-30 | H | Buˢ | H | H | H | CSSMe | —(CH₂)₅— | |
| J-31 | H | Buᵗ | H | H | H | CSSMe | —(CH₂)₅— | |
| J-32 | H | OMe | H | H | H | CSSMe | —(CH₂)₅— | |
| J-33 | H | OEt | H | H | H | CSSMe | —(CH₂)₅— | |
| J-34 | H | OPr | H | H | H | CSSMe | —(CH₂)₅— | |
| J-35 | H | OPrⁱ | H | H | H | CSSMe | —(CH₂)₅— | |
| J-36 | H | OCHF₂ | H | H | H | CSSMe | —(CH₂)₅— | |
| J-37 | H | OCF₃ | H | H | H | CSSMe | —(CH₂)₅— | |
| J-38 | H | CF₃ | H | H | H | CSSMe | —(CH₂)₅— | |
| J-39 | H | SMe | H | H | H | CSSMe | —(CH₂)₅— | |
| J-40 | H | SEt | H | H | H | CSSMe | —(CH₂)₅— | |
| J-41 | H | SPrⁱ | H | H | H | CSSMe | —(CH₂)₅— | |
| J-42 | H | NMe₂ | H | H | H | CSSMe | —(CH₂)₅— | |
| J-43 | H | NEt₂ | H | H | H | CSSMe | —(CH₂)₅— | |
| J-44 | H | H | Cl | H | H | CSSMe | —(CH₂)₅— | |
| J-45 | H | H | Br | H | H | CSSMe | —(CH₂)₅— | |
| J-46 | H | H | Me | H | H | CSSMe | —(CH₂)₅— | |
| J-47 | H | H | Et | H | H | CSSMe | —(CH₂)₅— | |
| J-48 | H | H | Pr | H | H | CSSMe | —(CH₂)₅— | |
| J-49 | H | H | Prⁱ | H | H | CSSMe | —(CH₂)₅— | |
| J-50 | H | H | Bu | H | H | CSSMe | —(CH₂)₅— | |

TABLE 67

| | R¹ | R² | R³ | R⁴ | R⁵ | R⁶ | R⁷ | R⁸ |
|---|---|---|---|---|---|---|---|---|
| J-51 | H | H | Buⁱ | H | H | CSSMe | —(CH₂)₅— | |
| J-52 | H | H | Buˢ | H | H | CSSMe | —(CH₂)₅— | |
| J-53 | H | H | Buᵗ | H | H | CSSMe | —(CH₂)₅— | |
| J-54 | H | H | OMe | H | H | CSSMe | —(CH₂)₅— | |
| J-55 | H | H | OEt | H | H | CSSMe | —(CH₂)₅— | |
| J-56 | H | H | OPr | H | H | CSSMe | —(CH₂)₅— | |
| J-57 | H | H | OPrⁱ | H | H | CSSMe | —(CH₂)₅— | |
| J-58 | H | H | OCHF₂ | H | H | CSSMe | —(CH₂)₅— | |
| J-59 | H | H | OCF₃ | H | H | CSSMe | —(CH₂)₅— | |
| J-60 | H | H | CF₃ | H | H | CSSMe | —(CH₂)₅— | |
| J-61 | H | H | SMe | H | H | CSSMe | —(CH₂)₅— | |
| J-62 | H | H | SEt | H | H | CSSMe | —(CH₂)₅— | |
| J-63 | H | H | SPrⁱ | H | H | CSSMe | —(CH₂)₅— | |
| J-64 | H | H | NMe₂ | H | H | CSSMe | —(CH₂)₅— | |
| J-65 | H | H | NEt₂ | H | H | CSSMe | —(CH₂)₅— | |
| J-66 | Me | NMe₂ | H | H | H | CSSMe | —(CH₂)₅— | |
| J-67 | NMe₂ | Cl | H | H | H | CSSMe | —(CH₂)₅— | |
| J-68 | Me | NEt₂ | H | H | H | CSSMe | —(CH₂)₅— | |
| J-69 | H | NEt₂ | Me | H | H | CSSMe | —(CH₂)₅— | |
| J-70 | Buˢ | H | H | H | H | CSSMe | —(CH₂)₅— | |
| J-71 | OMe | H | OMe | H | H | CSSMe | —(CH₂)₅— | |
| J-72 | H | OMe | OMe | H | H | CSSMe | —(CH₂)₅— | |
| J-73 | H | OMe | OEt | H | H | CSSMe | —(CH₂)₅— | |
| J-74 | H | OEt | OMe | H | H | CSSMe | —(CH₂)₅— | |
| J-75 | H | OEt | OEt | H | H | CSSMe | —(CH₂)₅— | |

TABLE 68

| | R¹ | R² | R³ | R⁴ | R⁵ | R⁶ | R⁷ | R⁸ |
|---|---|---|---|---|---|---|---|---|
| K-1 | H | H | H | H | H | COSEt | Et | Et |
| K-2 | Cl | H | H | H | H | COSEt | Et | Et |
| K-3 | Br | H | H | H | H | COSEt | Et | Et |
| K-4 | Me | H | H | H | H | COSEt | Et | Et |
| K-5 | Et | H | H | H | H | COSEt | Et | Et |
| K-6 | Pr | H | H | H | H | COSEt | Et | Et |
| K-7 | Bu | H | H | H | H | COSEt | Et | Et |
| K-8 | Buⁱ | H | H | H | H | COSEt | Et | Et |
| K-9 | Buᵗ | H | H | H | H | COSEt | Et | Et |
| K-10 | OMe | H | H | H | H | COSEt | Et | Et |
| K-11 | OEt | H | H | H | H | COSEt | Et | Et |
| K-12 | OPrⁱ | H | H | H | H | COSEt | Et | Et |
| K-13 | OPr | H | H | H | H | COSEt | Et | Et |
| K-14 | OCHF₂ | H | H | H | H | COSEt | Et | Et |
| K-15 | OCF₃ | H | H | H | H | COSEt | Et | Et |
| K-16 | CF₃ | H | H | H | H | COSEt | Et | Et |
| K-17 | SMe | H | H | H | H | COSEt | Et | Et |
| K-18 | SEt | H | H | H | H | COSEt | Et | Et |
| K-19 | SPrⁱ | H | H | H | H | COSEt | Et | Et |
| K-20 | NMe₂ | H | H | H | H | COSEt | Et | Et |
| K-21 | NEt₂ | H | H | H | H | COSEt | Et | Et |
| K-22 | H | Cl | H | H | H | COSEt | Et | Et |
| K-23 | H | Br | H | H | H | COSEt | Et | Et |
| K-24 | H | Me | H | H | H | COSEt | Et | Et |
| K-25 | H | Et | H | H | H | COSEt | Et | Et |

TABLE 69

| | R¹ | R² | R³ | R⁴ | R⁵ | R⁶ | R⁷ | R⁸ |
|---|---|---|---|---|---|---|---|---|
| K-26 | H | Pr | H | H | H | COSEt | Et | Et |
| K-27 | H | Prⁱ | H | H | H | COSEt | Et | Et |
| K-28 | H | Bu | H | H | H | COSEt | Et | Et |
| K-29 | H | Buⁱ | H | H | H | COSEt | Et | Et |
| K-30 | H | Buˢ | H | H | H | COSEt | Et | Et |
| K-31 | H | Buᵗ | H | H | H | COSEt | Et | Et |
| K-32 | H | OMe | H | H | H | COSEt | Et | Et |
| K-33 | H | OEt | H | H | H | COSEt | Et | Et |
| K-34 | H | OPr | H | H | H | COSEt | Et | Et |
| K-35 | H | OPrⁱ | H | H | H | COSEt | Et | Et |
| K-36 | H | OCHF₂ | H | H | H | COSEt | Et | Et |
| K-37 | H | OCF₃ | H | H | H | COSEt | Et | Et |
| K-38 | H | CF₃ | H | H | H | COSEt | Et | Et |
| K-39 | H | SMe | H | H | H | COSEt | Et | Et |
| K-40 | H | SEt | H | H | H | COSEt | Et | Et |
| K-41 | H | SPrⁱ | H | H | H | COSEt | Et | Et |
| K-42 | H | NMe₂ | H | H | H | COSEt | Et | Et |
| K-43 | H | NEt₂ | H | H | H | COSEt | Et | Et |
| K-44 | H | H | Cl | H | H | COSEt | Et | Et |
| K-45 | H | H | Br | H | H | COSEt | Et | Et |
| K-46 | H | H | Me | H | H | COSEt | Et | Et |
| K-47 | H | H | Et | H | H | COSEt | Et | Et |
| K-48 | H | H | Pr | H | H | COSEt | Et | Et |
| K-49 | H | H | Prⁱ | H | H | COSEt | Et | Et |
| K-50 | H | H | Bu | H | H | COSEt | Et | Et |

TABLE 70

| | R¹ | R² | R³ | R⁴ | R⁵ | R⁶ | R⁷ | R⁸ |
|---|---|---|---|---|---|---|---|---|
| K-51 | H | H | Buⁱ | H | H | COSEt | Et | Et |
| K-52 | H | H | Buˢ | H | H | COSEt | Et | Et |
| K-53 | H | H | Buᵗ | H | H | COSEt | Et | Et |
| K-54 | H | H | OMe | H | H | COSEt | Et | Et |
| K-55 | H | H | OEt | H | H | COSEt | Et | Et |
| K-56 | H | H | OPr | H | H | COSEt | Et | Et |
| K-57 | H | H | OPrⁱ | H | H | COSEt | Et | Et |
| K-58 | H | H | OCHF₂ | H | H | COSEt | Et | Et |
| K-59 | H | H | OCF₃ | H | H | COSEt | Et | Et |
| K-60 | H | H | CF₃ | H | H | COSEt | Et | Et |
| K-61 | H | H | SMe | H | H | COSEt | Et | Et |
| K-62 | H | H | SEt | H | H | COSEt | Et | Et |
| K-63 | H | H | SPrⁱ | H | H | COSEt | Et | Et |
| K-64 | H | H | NMe₂ | H | H | COSEt | Et | Et |
| K-65 | H | H | NEt₂ | H | H | COSEt | Et | Et |
| K-66 | Me | NMe₂ | H | H | H | COSEt | Et | Et |
| K-67 | NMe₂ | Cl | H | H | H | COSEt | Et | Et |
| K-68 | Me | NEt₂ | H | H | H | COSEt | Et | Et |
| K-69 | H | NEt₂ | Me | H | H | COSEt | Et | Et |
| K-70 | Buˢ | H | H | H | H | COSEt | Et | Et |
| K-71 | OMe | H | OMe | H | H | COSEt | Et | Et |
| K-72 | H | OMe | OMe | H | H | COSEt | Et | Et |
| K-73 | H | OMe | OEt | H | H | COSEt | Et | Et |
| K-74 | H | OEt | OMe | H | H | COSEt | Et | Et |
| K-75 | H | OEt | OEt | H | H | COSEt | Et | Et |

TABLE 71

| | R¹ | R² | R³ | R⁴ | R⁵ | R⁶ | R⁷ | R⁸ |
|---|---|---|---|---|---|---|---|---|
| L-1 | H | H | H | H | H | COSMe | Et | Et |
| L-2 | Cl | H | H | H | H | COSMe | Et | Et |
| L-3 | Br | H | H | H | H | COSMe | Et | Et |
| L-4 | Me | H | H | H | H | COSMe | Et | Et |
| L-5 | Et | H | H | H | H | COSMe | Et | Et |
| L-6 | Pr | H | H | H | H | COSMe | Et | Et |
| L-7 | Bu | H | H | H | H | COSMe | Et | Et |
| L-8 | Buⁱ | H | H | H | H | COSMe | Et | Et |
| L-9 | Buᵗ | H | H | H | H | COSMe | Et | El |
| L-10 | OMe | H | H | H | H | COSMe | Et | Et |
| L-11 | OEt | H | H | H | H | COSMe | Et | Et |
| L-12 | OPrⁱ | H | H | H | H | COSMe | Et | Et |
| L-13 | OPr | H | H | H | H | COSMe | Et | Et |
| L-14 | OCHF₂ | H | H | H | H | COSMe | Et | Et |
| L-15 | OCF₃ | H | H | H | H | COSMe | Et | Et |
| L-16 | CF₃ | H | H | H | H | COSMe | Et | Et |
| L-17 | SMe | H | H | H | H | COSMe | Et | Et |
| L-18 | SEt | H | H | H | H | COSMe | Et | Et |
| L-19 | SPrⁱ | H | H | H | H | COSMe | Et | Et |
| L-20 | NMe₂ | H | H | H | H | COSMe | Et | Et |
| L-21 | NEt₂ | H | H | H | H | COSMe | Et | Et |
| L-22 | H | Cl | H | H | H | COSMe | Et | Et |
| L-23 | H | Br | H | H | H | COSMe | Et | Et |
| L-24 | H | Me | H | H | H | COSMe | Et | Et |
| L-25 | H | Et | H | H | H | COSMe | Et | Et |

TABLE 72

| | R¹ | R² | R³ | R⁴ | R⁵ | R⁶ | R⁷ | R⁸ |
|---|---|---|---|---|---|---|---|---|
| L-26 | H | Pr | H | H | H | COSMe | Et | Et |
| L-27 | H | Prⁱ | H | H | H | COSMe | Et | Et |
| L-28 | H | Bu | H | H | H | COSMe | Et | Et |
| L-29 | H | Buⁱ | H | H | H | COSMe | Et | Et |
| L-30 | H | Buˢ | H | H | H | COSMe | Et | Et |
| L-31 | H | Buᵗ | H | H | H | COSMe | Et | Et |
| L-32 | H | OMe | H | H | H | COSMe | Et | Et |
| L-33 | H | OEt | H | H | H | COSMe | Et | Et |
| L-34 | H | OPr | H | H | H | COSMe | Et | Et |
| L-35 | H | OPrⁱ | H | H | H | COSMe | Et | Et |
| L-36 | H | OCHF₂ | H | H | H | COSMe | Et | Et |
| L-37 | H | OCF₃ | H | H | H | COSMe | Et | Et |
| L-38 | H | CF₃ | H | H | H | COSMe | Et | Et |
| L-39 | H | SMe | H | H | H | COSMe | Et | Et |
| L-40 | H | SEt | H | H | H | COSMe | Et | Et |
| L-41 | H | SPrⁱ | H | H | H | COSMe | Et | Et |
| L-42 | H | NMe₂ | H | H | H | COSMe | Et | Et |
| L-43 | H | NEt₂ | H | H | H | COSMe | Et | Et |
| L-44 | H | H | Cl | H | H | COSMe | Et | Et |
| L-45 | H | H | Br | H | H | COSMe | Et | Et |
| L-46 | H | H | Me | H | H | COSMe | Et | Et |
| L-47 | H | H | Et | H | H | COSMe | Et | Et |
| L-48 | H | H | Pr | H | H | COSMe | Et | Et |
| L-49 | H | H | Prⁱ | H | H | COSMe | Et | Et |
| L-50 | H | H | Bu | H | H | COSMe | Et | Et |

TABLE 73

| | R¹ | R² | R³ | R⁴ | R⁵ | R⁶ | R⁷ | R⁸ |
|---|---|---|---|---|---|---|---|---|
| L-51 | H | H | Buⁱ | H | H | COSMe | Et | Et |
| L-52 | H | H | Buˢ | H | H | COSMe | Et | Et |
| L-53 | H | H | Buᵗ | H | H | COSMe | Et | Et |
| L-54 | H | H | OMe | H | H | COSMe | Et | Et |
| L-55 | H | H | OEt | H | H | COSMe | Et | Et |
| L-56 | H | H | OPr | H | H | COSMe | Et | Et |
| L-57 | H | H | OPrⁱ | H | H | COSMe | Et | Et |
| L-58 | H | H | OCHF₂ | H | H | COSMe | Et | Et |
| L-59 | H | H | OCF₃ | H | H | COSMe | Et | Et |
| L-60 | H | H | CF₃ | H | H | COSMe | Et | Et |
| L-61 | H | H | SMe | H | H | COSMe | Et | Et |
| L-62 | H | H | SEt | H | H | COSMe | Et | Et |
| L-63 | H | H | SPrⁱ | H | H | COSMe | Et | Et |
| L-64 | H | H | NMe₂ | H | H | COSMe | Et | Et |
| L-65 | H | H | NEt₂ | H | H | COSMe | Et | Et |
| L-66 | Me | NMe₂ | H | H | H | COSMe | Et | Et |
| L-67 | NMe₂ | Cl | H | H | H | COSMe | Et | Et |
| L-68 | Me | NEt₂ | H | H | H | COSMe | Et | Et |
| L-69 | H | NEt₂ | Me | H | H | COSMe | Et | Et |
| L-70 | Buˢ | H | H | H | H | COSMe | Et | Et |
| L-71 | Prⁱ | H | H | H | H | COSMe | Et | Et |
| L-72 | H | OMe | OMe | H | H | COSMe | Et | Et |
| L-73 | H | OMe | OEt | H | H | COSMe | Et | Et |
| L-74 | H | OEt | OMe | H | H | COSMe | Et | Et |
| L-75 | H | OEt | OEt | H | H | COSMe | Et | Et |

TABLE 74

| | R¹ | R² | R³ | R⁴ | R⁵ | R⁶ | R⁷ | R⁸ |
|---|---|---|---|---|---|---|---|---|
| M-1 | H | H | H | H | H | COSMe | —(CH₂)₄— | |
| M-2 | Cl | H | H | H | H | COSMe | —(CH₂)₄— | |
| M-3 | Br | H | H | H | H | COSMe | —(CH₂)₄— | |
| M-4 | Me | H | H | H | H | COSMe | —(CH₂)₄— | |
| M-5 | Et | H | H | H | H | COSMe | —(CH₂)₄— | |
| M-6 | Pr | H | H | H | H | COSMe | —(CH₂)₄— | |
| M-7 | Bu | H | H | H | H | COSMe | —(CH₂)₄— | |
| M-8 | Buⁱ | H | H | H | H | COSMe | —(CH₂)₄— | |
| M-9 | Buᵗ | H | H | H | H | COSMe | —(CH₂)₄— | |
| M-10 | OMe | H | H | H | H | COSMe | —(CH₂)₄— | |
| M-11 | OEt | H | H | H | H | COSMe | —(CH₂)₄— | |
| M-12 | OPrⁱ | H | H | H | H | COSMe | —(CH₂)₄— | |
| M-13 | OPr | H | H | H | H | COSMe | —(CH₂)₄— | |
| M-14 | OCHF₂ | H | H | H | H | COSMe | —(CH₂)₄— | |
| M-15 | OCF₃ | H | H | H | H | COSMe | —(CH₂)₄— | |
| M-16 | CF₃ | H | H | H | H | COSMe | —(CH₂)₄— | |
| M-17 | SMe | H | H | H | H | COSMe | —(CH₂)₄— | |
| M-18 | SEt | H | H | H | H | COSMe | —(CH₂)₄— | |
| M-19 | SPrⁱ | H | H | H | H | COSMe | —(CH₂)₄— | |
| M-20 | NMe₂ | H | H | H | H | COSMe | —(CH₂)₄— | |
| M-21 | NEt₂ | H | H | H | H | COSMe | —(CH₂)₄— | |
| M-22 | H | Cl | H | H | H | COSMe | —(CH₂)₄— | |
| M-23 | H | Br | H | H | H | COSMe | —(CH₂)₄— | |
| M-24 | H | Me | H | H | H | COSMe | —(CH₂)₄— | |
| M-25 | H | Et | H | H | H | COSMe | —(CH₂)₄— | |

TABLE 75

| | R¹ | R² | R³ | R⁴ | R⁵ | R⁶ | R⁷ | R⁸ |
|---|---|---|---|---|---|---|---|---|
| M-26 | H | Pr | H | H | H | COSMe | —(CH₂)₄— | |
| M-27 | H | Prⁱ | H | H | H | COSMe | —(CH₂)₄— | |
| M-28 | H | Bu | H | H | H | COSMe | —(CH₂)₄— | |
| M-29 | H | Buⁱ | H | H | H | COSMe | —(CH₂)₄— | |
| M-30 | H | Buˢ | H | H | H | COSMe | —(CH₂)₄— | |
| M-31 | H | Buᵗ | H | H | H | COSMe | —(CH₂)₄— | |
| M-32 | H | OMe | H | H | H | COSMe | —(CH₂)₄— | |
| M-33 | H | OEt | H | H | H | COSMe | —(CH₂)₄— | |
| M-34 | H | OPr | H | H | H | COSMe | —(CH₂)₄— | |
| M-35 | H | OPrⁱ | H | H | H | COSMe | —(CH₂)₄— | |
| M-36 | H | OCHF₂ | H | H | H | COSMe | —(CH₂)₄— | |
| M-37 | H | OCF₃ | H | H | H | COSMe | —(CH₂)₄— | |
| M-38 | H | CF₃ | H | H | H | COSMe | —(CH₂)₄— | |
| M-39 | H | SMe | H | H | H | COSMe | —(CH₂)₄— | |
| M-40 | H | SEt | H | H | H | COSMe | —(CH₂)₄— | |
| M-41 | H | SPrⁱ | H | H | H | COSMe | —(CH₂)₄— | |
| M-42 | H | NMe₂ | H | H | H | COSMe | —(CH₂)₄— | |
| M-43 | H | NEt₂ | H | H | H | COSMe | —(CH₂)₄— | |
| M-44 | H | H | Cl | H | H | COSMe | —(CH₂)₄— | |
| M-45 | H | H | Br | H | H | COSMe | —(CH₂)₄— | |
| M-46 | H | H | Me | H | H | COSMe | —(CH₂)₄— | |
| M-47 | H | H | Et | H | H | COSMe | —(CH₂)₄— | |
| M-48 | H | H | Pr | H | H | COSMe | —(CH₂)₄— | |
| M-49 | H | H | Prⁱ | H | H | COSMe | —(CH₂)₄— | |
| M-50 | H | H | Bu | H | H | COSMe | —(CH₂)₄— | |

TABLE 76

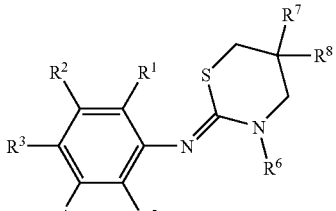

| | $R^1$ | $R^2$ | $R^3$ | $R^4$ | $R^5$ | $R^6$ | $R^7$ $R^8$ |
|---|---|---|---|---|---|---|---|
| M-51 | H | H | $Bu^i$ | H | H | COSMe | —$(CH_2)_4$— |
| M-52 | H | H | $Bu^s$ | H | H | COSMe | —$(CH_2)_4$— |
| M-53 | H | H | $Bu^t$ | H | H | COSMe | —$(CH_2)_4$— |
| M-54 | H | H | OMe | H | H | COSMe | —$(CH_2)_4$— |
| M-55 | H | H | OEt | H | H | COSMe | —$(CH_2)_4$— |
| M-56 | H | H | OPr | H | H | COSMe | —$(CH_2)_4$— |
| M-57 | H | H | $OPr^i$ | H | H | COSMe | —$(CH_2)_4$— |
| M-58 | H | H | $OCHF_2$ | H | H | COSMe | —$(CH_2)_4$— |
| M-59 | H | H | $OCF_3$ | H | H | COSMe | —$(CH_2)_4$— |
| M-60 | H | H | $CF_3$ | H | H | COSMe | —$(CH_2)_4$— |
| M-61 | H | H | SMe | H | H | COSMe | —$(CH_2)_4$— |
| M-62 | H | H | SEt | H | H | COSMe | —$(CH_2)_4$— |
| M-63 | H | H | $SPr^i$ | H | H | COSMe | —$(CH_2)_4$— |
| M-64 | H | H | $NMe_2$ | H | H | COSMe | —$(CH_2)_4$— |
| M-65 | H | H | $NEt_2$ | H | H | COSMe | —$(CH_2)_4$— |
| M-66 | Me | $NMe_2$ | H | H | H | COSMe | —$(CH_2)_4$— |
| M-67 | $NMe_2$ | Cl | H | H | H | COSMe | —$(CH_2)_4$— |
| M-68 | Me | $NEt_2$ | H | H | H | COSMe | —$(CH_2)_4$— |
| M-69 | H | $NEt_2$ | Me | H | H | COSMe | —$(CH_2)_4$— |
| M-70 | $Bu^s$ | H | H | H | H | COSMe | —$(CH_2)_4$— |
| M-71 | $Pr^i$ | H | H | H | H | COSMe | —$(CH_2)_4$— |
| M-72 | H | OMe | OMe | H | H | COSMe | —$(CH_2)_4$— |
| M-73 | H | OMe | OEt | H | H | COSMe | —$(CH_2)_4$— |
| M-74 | H | OEt | OMe | H | H | COSMe | —$(CH_2)_4$— |
| M-75 | H | OEt | OEt | H | H | COSMe | —$(CH_2)_4$— |

TABLE 77

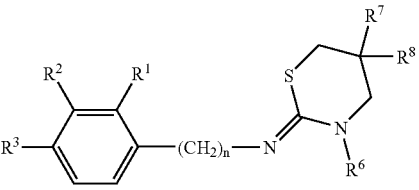

| | $R^1$ | $R^2$ | $R^3$ | n | $R^6$ | $R^7$ | $R^8$ |
|---|---|---|---|---|---|---|---|
| R-1 | H | H | H | 1 | CSSMe | Me | Me |
| R-2 | Cl | H | H | 1 | CSSMe | Me | Me |
| R-3 | Br | H | H | 1 | CSSMe | Me | Me |
| R-4 | Me | H | H | 1 | CSSMe | Me | Me |
| R-5 | Et | H | H | 1 | CSSMe | Me | Me |
| R-6 | Pr | H | H | 1 | CSSMe | Me | Me |
| R-7 | Bu | H | H | 1 | CSSMe | Me | Me |
| R-8 | $Bu^i$ | H | H | 1 | CSSMe | Me | Me |
| R-9 | $Bu^t$ | H | H | 1 | CSSMe | Me | Me |
| R-10 | $Pr^i$ | H | H | 1 | CSSMe | Me | Me |
| R-11 | OEt | H | H | 1 | CSSMe | Me | Me |
| R-12 | $OPr^i$ | H | H | 1 | CSSMe | Me | Me |
| R-13 | OPr | H | H | 1 | CSSMe | Me | Me |
| R-14 | $OCHF_2$ | H | H | 1 | CSSMe | Me | Me |
| R-15 | $OCF_3$ | H | H | 1 | CSSMe | Me | Me |
| R-16 | $CF_3$ | H | H | 1 | CSSMe | Me | Me |
| R-17 | SMe | H | H | 1 | CSSMe | Me | Me |
| R-18 | SEt | H | H | 1 | CSSMe | Me | Me |
| R-19 | $SPr^i$ | H | H | 1 | CSSMe | Me | Me |
| R-20 | $NMe_2$ | H | H | 1 | CSSMe | Me | Me |
| R-21 | $NEt_2$ | H | H | 1 | CSSMe | Me | Me |
| R-22 | H | Cl | H | 1 | CSSMe | Me | Me |
| R-23 | H | Br | H | 1 | CSSMe | Me | Me |

TABLE 77-continued

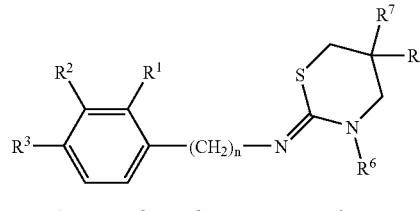

| | $R^1$ | $R^2$ | $R^3$ | n | $R^6$ | $R^7$ | $R^8$ |
|---|---|---|---|---|---|---|---|
| R-24 | H | Me | H | 1 | CSSMe | Me | Me |
| R-25 | H | Et | H | 1 | CSSMe | Me | Me |

TABLE 78

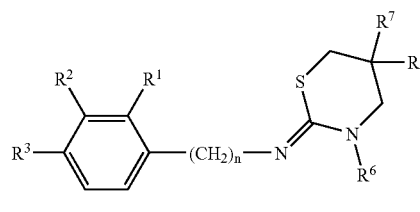

| | $R^1$ | $R^2$ | $R^3$ | n | $R^6$ | $R^7$ | $R^8$ |
|---|---|---|---|---|---|---|---|
| R-26 | H | Pr | H | 1 | CSSMe | Me | Me |
| R-27 | H | $Pr^i$ | H | 1 | CSSMe | Me | Me |
| R-28 | H | Bu | H | 1 | CSSMe | Me | Me |
| R-29 | H | $Bu^i$ | H | 1 | CSSMe | Me | Me |
| R-30 | H | $Bu^s$ | H | 1 | CSSMe | Me | Me |
| R-31 | H | $Bu^t$ | H | 1 | CSSMe | Me | Me |
| R-32 | H | OMe | H | 1 | CSSMe | Me | Me |
| R-33 | H | OEt | H | 1 | CSSMe | Me | Me |
| R-34 | H | OPr | H | 1 | CSSMe | Me | Me |
| R-35 | H | $OPr^i$ | H | 1 | CSSMe | Me | Me |
| R-36 | H | $OCHF_2$ | H | 1 | CSSMe | Me | Me |
| R-37 | H | $OCF_3$ | H | 1 | CSSMe | Me | Me |
| R-38 | H | $CF_3$ | H | 1 | CSSMe | Me | Me |
| R-39 | H | SMe | H | 1 | CSSMe | Me | Me |
| R-40 | H | SEt | H | 1 | CSSMe | Me | Me |
| R-41 | H | $SPr^i$ | H | 1 | CSSMe | Me | Me |
| R-42 | H | $NMe_2$ | H | 1 | CSSMe | Me | Me |
| R-43 | H | $NEt_2$ | H | 1 | CSSMe | Me | Me |
| R-44 | Cl | H | Cl | 1 | CSSMe | Me | Me |
| R-45 | H | H | Br | 1 | CSSMe | Me | Me |
| R-46 | H | H | Me | 1 | CSSMe | Me | Me |
| R-47 | H | H | Et | 1 | CSSMe | Me | Me |
| R-48 | H | H | Pr | 1 | CSSMe | Me | Me |
| R-49 | H | H | $Pr^i$ | 1 | CSSMe | Me | Me |
| R-50 | H | H | Bu | 1 | CSSMe | Me | Me |

TABLE 79

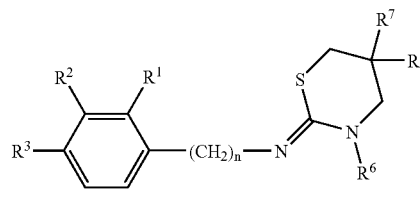

| | $R^1$ | $R^2$ | $R^3$ | n | $R^6$ | $R^7$ | $R^8$ |
|---|---|---|---|---|---|---|---|
| R-51 | H | H | $Bu^i$ | 1 | CSSMe | Me | Me |
| R-52 | H | H | $Bu^s$ | 1 | CSSMe | Me | Me |
| R-53 | H | H | $Bu^t$ | 1 | CSSMe | Me | Me |
| R-54 | H | H | OMe | 1 | CSSMe | Me | Me |
| R-55 | H | H | OEt | 1 | CSSMe | Me | Me |
| R-56 | H | H | OPr | 1 | CSSMe | Me | Me |

TABLE 79-continued

| | R¹ | R² | R³ | n | R⁶ | R⁷ | R⁸ |
|---|---|---|---|---|---|---|---|
| R-57 | H | H | OPr$^i$ | 1 | CSSMe | Me | Me |
| R-58 | H | H | OCHF$_2$ | 1 | CSSMe | Me | Me |
| R-59 | H | H | OCF$_3$ | 1 | CSSMe | Me | Me |
| R-60 | H | H | CF$_3$ | 1 | CSSMe | Me | Me |
| R-61 | H | H | SMe | 1 | CSSMe | Me | Me |
| R-62 | H | H | SEt | 1 | CSSMe | Me | Me |
| R-63 | H | H | SPr$^i$ | 1 | CSSMe | Me | Me |
| R-64 | H | H | NMe$_2$ | 1 | CSSMe | Me | Me |
| R-65 | H | H | NEt$_2$ | 1 | CSSMe | Me | Me |
| R-66 | Me | NMe$_2$ | H | 1 | CSSMe | Me | Me |
| R-67 | NMe$_2$ | Cl | H | 1 | CSSMe | Me | Me |
| R-68 | Me | NEt$_2$ | H | 1 | CSSMe | Me | Me |
| R-69 | H | NEt$_2$ | Me | 1 | CSSMe | Me | Me |
| R-70 | Bu$^s$ | H | H | 1 | CSSMe | Me | Me |
| R-71 | OMe | H | OMe | 1 | CSSMe | Me | Me |
| R-72 | H | OMe | OMe | 1 | CSSMe | Me | Me |
| R-73 | H | OMe | OEt | 1 | CSSMe | Me | Me |
| R-74 | H | OEt | OMe | 1 | CSSMe | Me | Me |
| R-75 | H | OEt | OEt | 1 | CSSMe | Me | Me |

TABLE 80

| | R¹ | R² | R³ | n | R⁶ | R⁷ | R⁸ |
|---|---|---|---|---|---|---|---|
| O-1 | H | H | H | 2 | CSSMe | Me | Me |
| O-2 | Cl | H | H | 2 | CSSMe | Me | Me |
| O-3 | Br | H | H | 2 | CSSMe | Me | Me |
| O-4 | Me | H | H | 2 | CSSMe | Me | Me |
| O-5 | Et | H | H | 2 | CSSMe | Me | Me |
| O-6 | Pr | H | H | 2 | CSSMe | Me | Me |
| O-7 | Bu | H | H | 2 | CSSMe | Me | Me |
| O-8 | Bu$^i$ | H | H | 2 | CSSMe | Me | Me |
| O-9 | Bu$^t$ | H | H | 2 | CSSMe | Me | Me |
| O-10 | Pr$^i$ | H | H | 2 | CSSMe | Me | Me |
| O-11 | OEt | H | H | 2 | CSSMe | Me | Me |
| O-12 | OPr$^i$ | H | H | 2 | CSSMe | Me | Me |
| O-13 | OPr | H | H | 2 | CSSMe | Me | Me |
| O-14 | OCHF$_2$ | H | H | 2 | CSSMe | Me | Me |
| O-15 | OCF$_3$ | H | H | 2 | CSSMe | Me | Me |
| O-16 | CF$_3$ | H | H | 2 | CSSMe | Me | Me |
| O-17 | SMe | H | H | 2 | CSSMe | Me | Me |
| O-18 | SEt | H | H | 2 | CSSMe | Me | Me |
| O-19 | SPr$^i$ | H | H | 2 | CSSMe | Me | Me |
| O-20 | NMe$_2$ | H | H | 2 | CSSMe | Me | Me |
| O-21 | NEt$_2$ | H | H | 2 | CSSMe | Me | Me |
| O-22 | H | Cl | H | 2 | CSSMe | Me | Me |
| O-23 | H | Br | H | 2 | CSSMe | Me | Me |
| O-24 | H | Me | H | 2 | CSSMe | Me | Me |
| O-25 | H | Et | H | 2 | CSSMe | Me | Me |

TABLE 81

| | R¹ | R² | R³ | m | R⁶ | R⁷ | R⁸ |
|---|---|---|---|---|---|---|---|
| O-26 | H | Pr | H | 2 | CSSMe | Me | Me |
| O-27 | H | Pr$^i$ | H | 2 | CSSMe | Me | Me |
| O-28 | H | Bu | H | 2 | CSSMe | Me | Me |
| O-29 | H | Bu$^i$ | H | 2 | CSSMe | Me | Me |
| O-30 | H | Bu$^s$ | H | 2 | CSSMe | Me | Me |
| O-31 | H | Bu$^t$ | H | 2 | CSSMe | Me | Me |
| O-32 | H | OMe | H | 2 | CSSMe | Me | Me |
| O-33 | H | OEt | H | 2 | CSSMe | Me | Me |
| O-34 | H | OPr | H | 2 | CSSMe | Me | Me |
| O-35 | H | OPr$^i$ | H | 2 | CSSMe | Me | Me |
| O-36 | H | OCHF$_2$ | H | 2 | CSSMe | Me | Me |
| O-37 | H | OCF$_3$ | H | 2 | CSSMe | Me | Me |
| O-38 | H | CF$_3$ | H | 2 | CSSMe | Me | Me |
| O-39 | H | SMe | H | 2 | CSSMe | Me | Me |
| O-40 | H | SEt | H | 2 | CSSMe | Me | Me |
| O-41 | H | SPr$^i$ | H | 2 | CSSMe | Me | Me |
| O-42 | H | NMe$_2$ | H | 2 | CSSMe | Me | Me |
| O-43 | H | NEt$_2$ | H | 2 | CSSMe | Me | Me |
| O-44 | F | H | F | 2 | CSSMe | Me | Me |
| O-45 | H | H | Br | 2 | CSSMe | Me | Me |
| O-46 | H | H | Me | 2 | CSSMe | Me | Me |
| O-47 | H | H | Et | 2 | CSSMe | Me | Me |
| O-48 | H | H | Pr | 2 | CSSMe | Me | Me |
| O-49 | H | H | Pr$^i$ | 2 | CSSMe | Me | Me |
| O-50 | H | H | Bu | 2 | CSSMe | Me | Me |

TABLE 82

| | R¹ | R² | R³ | n | R⁶ | R⁷ | R⁸ |
|---|---|---|---|---|---|---|---|
| O-51 | H | H | Bu$^i$ | 2 | CSSMe | Me | Me |
| O-52 | H | H | Bu$^s$ | 2 | CSSMe | Me | Me |
| O-53 | H | H | Bu$^t$ | 2 | CSSMe | Me | Me |
| O-54 | H | H | OMe | 2 | CSSMe | Me | Me |
| O-55 | H | H | OEt | 2 | CSSMe | Me | Me |
| O-56 | H | H | OPr | 2 | CSSMe | Me | Me |
| O-57 | H | H | OPr$^i$ | 2 | CSSMe | Me | Me |
| O-58 | H | H | OCHF$_2$ | 2 | CSSMe | Me | Me |
| O-59 | H | H | OCF$_3$ | 2 | CSSMe | Me | Me |
| O-60 | H | H | CF$_3$ | 2 | CSSMe | Me | Me |
| O-61 | H | H | SMe | 2 | CSSMe | Me | Me |
| O-62 | H | H | SEt | 2 | CSSMe | Me | Me |
| O-63 | H | H | SPr$^i$ | 2 | CSSMe | Me | Me |
| O-64 | H | H | NMe$_2$ | 2 | CSSMe | Me | Me |
| O-65 | H | H | NEt$_2$ | 2 | CSSMe | Me | Me |
| O-66 | Me | NMe$_2$ | H | 2 | CSSMe | Me | Me |
| O-67 | NMe$_2$ | Cl | H | 2 | CSSMe | Me | Me |
| O-68 | Me | NEt$_2$ | H | 2 | CSSMe | Me | Me |
| O-69 | H | NEt$_2$ | Me | 2 | CSSMe | Me | Me |
| O-70 | Bu$^s$ | H | H | 2 | CSSMe | Me | Me |
| O-71 | OMe | H | OMe | 2 | CSSMe | Me | Me |
| O-72 | H | OMe | OMe | 2 | CSSMe | Me | Me |
| O-73 | H | OMe | OEt | 2 | CSSMe | Me | Me |

TABLE 82-continued

| | R¹ | R² | R³ | n | R⁶ | R⁷ | R⁸ |
|---|---|---|---|---|---|---|---|
| O-74 | H | OEt | OMe | 2 | CSSMe | Me | Me |
| O-75 | H | OEt | OEt | 2 | CSSMe | Me | Me |

TABLE 83

| | R¹ | R² | R³ | n | R⁶ | R⁷ | R⁸ |
|---|---|---|---|---|---|---|---|
| P-1 | H | H | H | 1 | CSSMe | Et | Et |
| P-2 | Cl | H | H | 1 | CSSMe | Et | Et |
| P-3 | Br | H | H | 1 | CSSMe | Et | Et |
| P-4 | Me | H | H | 1 | CSSMe | Et | Et |
| P-5 | Et | H | H | 1 | CSSMe | Et | Et |
| P-6 | Pr | H | H | 1 | CSSMe | Et | Et |
| P-7 | Bu | H | H | 1 | CSSMe | Et | Et |
| P-8 | Buⁱ | H | H | 1 | CSSMe | Et | Et |
| P-9 | Buᵗ | H | H | 1 | CSSMe | Et | Et |
| P-10 | Prⁱ | H | H | 1 | CSSMe | Et | Et |
| P-11 | OEt | H | H | 1 | CSSMe | Et | Et |
| P-12 | OPrⁱ | H | H | 1 | CSSMe | Et | Et |
| P-13 | OPr | H | H | 1 | CSSMe | Et | Et |
| P-14 | OCHF₂ | H | H | 1 | CSSMe | Et | Et |
| P-15 | OCF₃ | H | H | 1 | CSSMe | Et | Et |
| P-16 | CF₃ | H | H | 1 | CSSMe | Et | Et |
| P-17 | SMe | H | H | 1 | CSSMe | Et | Et |
| P-18 | SEt | H | H | 1 | CSSMe | Et | Et |
| P-19 | SPrⁱ | H | H | 1 | CSSMe | Et | Et |
| P-20 | NMe₂ | H | H | 1 | CSSMe | Et | Et |
| P-21 | NEt₂ | H | H | 1 | CSSMe | Et | Et |
| P-22 | H | Cl | H | 1 | CSSMe | Et | Et |
| P-23 | H | Br | H | 1 | CSSMe | Et | Et |
| P-24 | H | Me | H | 1 | CSSMe | Et | Et |
| P-25 | H | Et | H | 1 | CSSMe | Et | Et |

TABLE 84

| | R¹ | R² | R³ | n | R⁶ | R⁷ | R⁸ |
|---|---|---|---|---|---|---|---|
| P-26 | H | Pr | H | 1 | CSSMe | Et | Et |
| P-27 | H | Prⁱ | H | 1 | CSSMe | Et | Et |
| P-28 | H | Bu | H | 1 | CSSMe | Et | Et |
| P-29 | H | Buⁱ | H | 1 | CSSMe | Et | Et |
| P-30 | H | Buˢ | H | 1 | CSSMe | Et | Et |
| P-31 | H | Buᵗ | H | 1 | CSSMe | Et | Et |
| P-32 | H | OMe | H | 1 | CSSMe | Et | Et |
| P-33 | H | OEt | H | 1 | CSSMe | Et | Et |
| P-34 | H | OPr | H | 1 | CSSMe | Et | Et |
| P-35 | H | OPrⁱ | H | 1 | CSSMe | Et | Et |
| P-36 | H | OCHF₂ | H | 1 | CSSMe | Et | Et |
| P-37 | H | OCF₃ | H | 1 | CSSMe | Et | Et |
| P-38 | H | CF₃ | H | 1 | CSSMe | Et | Et |
| P-39 | H | SMe | H | 1 | CSSMe | Et | Et |
| P-40 | H | SEt | H | 1 | CSSMe | Et | Et |
| P-41 | H | SPrⁱ | H | 1 | CSSMe | Et | Et |
| P-42 | H | NMe₂ | H | 1 | CSSMe | Et | Et |
| P-43 | H | NEt₂ | H | 1 | CSSMe | Et | Et |
| P-44 | OMe | H | H | 1 | CSSMe | Et | Et |
| P-45 | H | H | Br | 1 | CSSMe | Et | Et |
| P-46 | H | H | Me | 1 | CSSMe | Et | Et |
| P-47 | H | H | Et | 1 | CSSMe | Et | Et |
| P-48 | H | H | Pr | 1 | CSSMe | Et | Et |
| P-49 | H | H | Prⁱ | 1 | CSSMe | Et | Et |
| P-50 | H | H | Bu | 1 | CSSMe | Et | Et |

TABLE 85

| | R¹ | R² | R³ | n | R⁶ | R⁷ | R⁸ |
|---|---|---|---|---|---|---|---|
| P-51 | H | H | Buⁱ | 1 | CSSMe | Et | Et |
| P-52 | H | H | Buˢ | 1 | CSSMe | Et | Et |
| P-53 | H | H | Buᵗ | 1 | CSSMe | Et | Et |
| P-54 | H | H | OMe | 1 | CSSMe | Et | Et |
| P-55 | H | H | OEt | 1 | CSSMe | Et | Et |
| P-56 | H | H | OPr | 1 | CSSMe | Et | Et |
| P-57 | H | H | OPrⁱ | 1 | CSSMe | Et | Et |
| P-58 | H | H | OCHF₂ | 1 | CSSMe | Et | Et |
| P-59 | H | H | OCF₃ | 1 | CSSMe | Et | Et |
| P-60 | H | H | CF₃ | 1 | CSSMe | Et | Et |
| P-61 | H | H | SMe | 1 | CSSMe | Et | Et |
| P-62 | H | H | SEt | 1 | CSSMe | Et | Et |
| P-63 | H | H | SPrⁱ | 1 | CSSMe | Et | Et |
| P-64 | H | H | NMe₂ | 1 | CSSMe | Et | Et |
| P-65 | H | H | NEt₂ | 1 | CSSMe | Et | Et |
| P-66 | Me | NMe₂ | H | 1 | CSSMe | Et | Et |
| P-67 | NMe₂ | Cl | H | 1 | CSSMe | Et | Et |
| P-68 | Me | NEt₂ | H | 1 | CSSMe | Et | Et |
| P-69 | H | NEt₂ | Me | 1 | CSSMe | Et | Et |
| P-70 | Buˢ | H | H | 1 | CSSMe | Et | Et |
| P-71 | OMe | H | OMe | 1 | CSSMe | Et | Et |
| P-72 | H | OMe | OMe | 1 | CSSMe | Et | Et |
| P-73 | H | OMe | OEt | 1 | CSSMe | Et | Et |
| P-74 | H | OEt | OMe | 1 | CSSMe | Et | Et |
| P-75 | H | OEt | OEt | 1 | CSSMe | Et | Et |

TABLE 86

|  | R¹ | R² | R³ | n | R⁶ | R⁷ | R⁸ |
|---|---|---|---|---|---|---|---|
| Q-1 | H | H | H | 2 | CSSMe | Et | Et |
| Q-2 | Cl | H | H | 2 | CSSMe | Et | Et |
| Q-3 | Br | H | H | 2 | CSSMe | Et | Et |
| Q-4 | Me | H | H | 2 | CSSMe | Et | Et |
| Q-5 | Et | H | H | 2 | CSSMe | Et | Et |
| Q-6 | Pr | H | H | 2 | CSSMe | Et | Et |
| Q-7 | Bu | H | H | 2 | CSSMe | Et | Et |
| Q-8 | $Bu^i$ | H | H | 2 | CSSMe | Et | Et |
| Q-9 | $Bu^t$ | H | H | 2 | CSSMe | Et | Et |
| Q-10 | $Pr^i$ | H | H | 2 | CSSMe | Et | Et |
| Q-11 | OEt | H | H | 2 | CSSMe | Et | Et |
| Q-12 | $OPr^i$ | H | H | 2 | CSSMe | Et | Et |
| Q-13 | OPr | H | H | 2 | CSSMe | Et | Et |
| Q-14 | $OCHF_2$ | H | H | 2 | CSSMe | Et | Et |
| Q-15 | $OCF_3$ | H | H | 2 | CSSMe | Et | Et |
| Q-16 | $CF_3$ | H | H | 2 | CSSMe | Et | Et |
| Q-17 | SMe | H | H | 2 | CSSMe | Et | Et |
| Q-18 | SEt | H | H | 2 | CSSMe | Et | Et |
| Q-19 | $SPr^i$ | H | H | 2 | CSSMe | Et | Et |
| Q-20 | $NMe_2$ | H | H | 2 | CSSMe | Et | Et |
| Q-21 | $NEt_2$ | H | H | 2 | CSSMe | Et | Et |
| Q-22 | H | Cl | H | 2 | CSSMe | Et | Et |
| Q-23 | H | Br | H | 2 | CSSMe | Et | Et |
| Q-24 | H | Me | H | 2 | CSSMe | Et | Et |
| Q-25 | H | Et | H | 2 | CSSMe | Et | Et |

TABLE 87

|  | R¹ | R² | R³ | m | R⁶ | R⁷ | R⁸ |
|---|---|---|---|---|---|---|---|
| Q-26 | H | Pr | H | 2 | CSSMe | Et | Et |
| Q-27 | H | $Pr^i$ | H | 2 | CSSMe | Et | Et |
| Q-28 | H | Bu | H | 2 | CSSMe | Et | Et |
| Q-29 | H | $Bu^i$ | H | 2 | CSSMe | Et | Et |
| Q-30 | H | $Bu^s$ | H | 2 | CSSMe | Et | Et |
| Q-31 | H | $Bu^t$ | H | 2 | CSSMe | Et | Et |
| Q-32 | H | OMe | H | 2 | CSSMe | Et | Et |
| Q-33 | H | OEt | H | 2 | CSSMe | Et | Et |
| Q-34 | H | OPr | H | 2 | CSSMe | Et | Et |
| Q-35 | H | $OPr^i$ | H | 2 | CSSMe | Et | Et |
| Q-36 | H | $OCHF_2$ | H | 2 | CSSMe | Et | Et |
| Q-37 | H | $OCF_3$ | H | 2 | CSSMe | Et | Et |
| Q-38 | H | $CF_3$ | H | 2 | CSSMe | Et | Et |
| Q-39 | H | SMe | H | 2 | CSSMe | Et | Et |
| Q-40 | H | SEt | H | 2 | CSSMe | Et | Et |
| Q-41 | H | $SPr^i$ | H | 2 | CSSMe | Et | Et |
| Q-42 | H | $NMe_2$ | H | 2 | CSSMe | Et | Et |
| Q-43 | H | $NEt_2$ | H | 2 | CSSMe | Et | Et |
| Q-44 | OMe | H | H | 2 | CSSMe | Et | Et |
| Q-45 | H | H | Br | 2 | CSSMe | Et | Et |
| Q-46 | H | H | Me | 2 | CSSMe | Et | Et |
| Q-47 | H | H | Et | 2 | CSSMe | Et | Et |
| Q-48 | H | H | Pr | 2 | CSSMe | Et | Et |
| Q-49 | H | H | $Pr^i$ | 2 | CSSMe | Et | Et |
| Q-50 | H | H | Bu | 2 | CSSMe | Et | Et |

TABLE 88

|  | R¹ | R² | R³ | n | R⁶ | R⁷ | R⁸ |
|---|---|---|---|---|---|---|---|
| Q-51 | H | H | $Bu^i$ | 2 | CSSMe | Et | Et |
| Q-52 | H | H | $Bu^s$ | 2 | CSSMe | Et | Et |
| Q-53 | H | H | $Bu^t$ | 2 | CSSMe | Et | Et |
| Q-54 | H | H | OMe | 2 | CSSMe | Et | Et |
| Q-55 | H | H | OEt | 2 | CSSMe | Et | Et |
| Q-56 | H | H | OPr | 2 | CSSMe | Et | Et |
| Q-57 | H | H | $OPr^i$ | 2 | CSSMe | Et | Et |
| Q-58 | H | H | $OCHF_2$ | 2 | CSSMe | Et | Et |
| Q-59 | H | H | $OCF_3$ | 2 | CSSMe | Et | Et |
| Q-60 | H | H | $CF_3$ | 2 | CSSMe | Et | Et |
| Q-61 | H | H | SMe | 2 | CSSMe | Et | Et |
| Q-62 | H | H | SEt | 2 | CSSMe | Et | Et |
| Q-63 | H | H | $SPr^i$ | 2 | CSSMe | Et | Et |
| Q-64 | H | H | $NMe_2$ | 2 | CSSMe | Et | Et |
| Q-65 | H | H | $NEt_2$ | 2 | CSSMe | Et | Et |
| Q-66 | Me | $NMe_2$ | H | 2 | CSSMe | Et | Et |
| Q-67 | $NMe_2$ | Cl | H | 2 | CSSMe | Et | Et |
| Q-68 | Me | $NEt_2$ | H | 2 | CSSMe | Et | Et |
| Q-69 | H | $NEt_2$ | Me | 2 | CSSMe | Et | Et |
| Q-70 | $Bu^s$ | H | H | 2 | CSSMe | Et | Et |
| Q-71 | OMe | H | OMe | 2 | CSSMe | Et | Et |
| Q-72 | H | OMe | OMe | 2 | CSSMe | Et | Et |
| Q-73 | H | OMe | OEt | 2 | CSSMe | Et | Et |
| Q-74 | H | OEt | OMe | 2 | CSSMe | Et | Et |
| Q-75 | H | OEt | OEt | 2 | CSSMe | Et | Et |

The above compounds of the present invention were examined as shown below.

Example 1

Experiments for Human CB2 Receptor (CB2R) Binding Inhibition

The coding region of human CB2R cDNA (Munro etc, Nature, 1993, 365, 61–65) was inserted into the mammalian expression vector, pSVL SV40 Late Promoter Expression Vector (Amersham Pharmacia Biotech Inc.). The prepared vector was transfected into Chinese Hamster Ovary (CHO) cells with LipofectAMINE reagent (Gibco BRL) according to the manufacture's protocol, and the stable CB2R-expressing clones were selected.

The crude membrane fractions were then prepared from the CB2R-expressing CHO cells. Receptor binding assay was performed by incubating the membranes with each test compound and [$^3$H]CP55940 (at a final concentration of 0.5 nM: NEN Life Science Products) in the assay buffer (50 mM Tris-HCl, 1 mM EDTA, 3 mM MgCl$_2$, pH 7.4) containing 0.5% bovine serum albumin (BSA) for 2 hr at 25° C. The incubation mixture was filtered through 1% polyethylenimine (PEI)-treated GF/C glass filter and washed with 50 mM Tris-HCl (pH 7.4) containing 0.1% BSA. The radioactivity was then counted with a liquid scintillation counter. Nonspecific binding was determined in the presence of 10 µM WIN55212-2 (a CB agonist described in the patent U.S. Pat. No. 508,122, Research Biochemicals International), and the specific binding was calculated by subtracting the nonspecific binding from the total binding. The IC$_{50}$ value for each test compound was determined as the concentration at which 50% of the specific binding was inhibited.

For the receptor binding assay of human CB1 receptor (CB1R), the stable CB1R-expressing CHO cells were prepared as described above, and the binding assay was performed with their membrane fractions. As a consequence of these studies, the Ki values of each test compound for both cannabinoid receptors were determined, which were presented in Table 89. As shown in this table, a series of compounds described in the present invention were found to selectively block the binding of CP55940 (a CB agonist described in the patent U.S. Pat. No. 4,371,720) to CB2R more effectively than CB1R.

TABLE 89

| Compound | Ki (nM) | |
| No. | CB1 receptor | CB2 receptor |
| --- | --- | --- |
| I-5 | >5000 | 61 |
| I-23 | >5000 | 29 |
| I-50 | >5000 | 39 |
| I-51 | n.t. | 23 |
| I-52 | n.t. | 35 |
| I-56 | n.t. | 54 |
| I-6 | >5000 | 9 |
| I-57 | 4134 | 6 |
| I-69 | n.t. | 33 |
| I-60 | 2097 | 18 |
| I-62 | n.t. | 44 |
| I-63 | n.t. | 43 |
| I-74 | n.t. | 48 |
| I-77 | n.t. | 53 |
| I-84 | >5000 | 35 |
| I-85 | n.t. | 25 | n.t.: not tested

Example 2

Inhibition Experiments for CB2R-Mediated Suppression of cAMP Synthesis

The CHO cells expressing human CB2R were incubated with test compounds for 15 min. After the incubation, 4 µM forskolin (Sigma) was added and the cells were incubated for 20 min at 37° C. The reaction was stopped by the addition of 1N HCl and the amount of cAMP in the cell supernatant was measured using an EIA kit (Amersham Pharmacia Biotech) according to the manufacture's protocol. The cAMP amount increased by forskolin compared to that in the absence of forskolin was defined as 100%, and the IC$_{50}$ value of each test compound was determined as the concentration at which 50% of the forskolin-stimulated cAMP synthesis was inhibited. As a consequence of these studies, the IC$_{50}$ value of each test compound was presented in Table 90. As shown in Table 90, the compounds described in the present invention were found to possess agonistic activity toward CB2R.

The antagonistic activity of each compound was also evaluated in this assay.

TABLE 90

| Compound No. | IC$_{50}$ (nM) |
| --- | --- |
| I-5 | 6.5 |
| I-23 | 2.6 |
| I-51 | 2.8 |
| I-6 | 2.7 |
| I-57 | 5.5 |

Example 3

Experiments for Sheep Red Blood Cell (SRBC)-induced Delayed Type Hypersensitive (DTH) Reaction Female ddY mice (7 weeks old) were used for the sheep red blood cell (SRBC)-induced delayed type hypersensitive (DTH) reaction.

Cannabinoid receptor agonist, I-6, I-60, I-77 and I-118 were suspended in 0.6% arabic gum solution. Mice were sensitized by the intradermal injection of 10$^7$ cells of SRBC (40 µl/foot) into the left hind foot pad. After 5 days, DTH reaction was induced by the intradermal injection of 10$^8$ cells of SRBC in the right hind foot pad. Test compounds were administerd p.o. (10 ml/kg) 1 hr before and 5 hr after the induction of DTH reaction. After 24 hrs of the injection of SRBC, the left and right foot pad volumes were measured by the water displacement method. The foot pad swelling was calculated as the differences in the volumes between the right and left hind foot pad, and used as an index of the DTH reaction.

Data are expressed as the inhibition percentage of each compound. Statistical analysis was performed with Welch's t-test, in which the value of $P<0.05$ is considered as a significant difference.

TABLE 91

| Comp. No. | Dose (mg/kg) | Inhibition percentage (%) |
| --- | --- | --- |
| I-6 | 40 | 45.2 |
| I-60 | 30 | 31.1 |
| I-77 | 30 | 33.8 |
| I-118 | 30 | 33.0 |

INDUSTRIAL APPLICABILITY

The compound of the formula (I) and (II) of the present invention selectively binds to the cannabinoid type 2 receptor (CB2R) to exhibit an antagonistic activity or agonistic activity to CB2R. Therefore, the present compound neither causes side effects on the central nervous system such as illusion or the drug dependence associated with the cannabinoid type 1 receptor (CB1R) and can be used for treating or preventing diseases associated with the cannabinoid type 2 receptor (CB2R).

The invention claimed is:

1. A pharmaceutical composition comprising a compound of the formula (I):

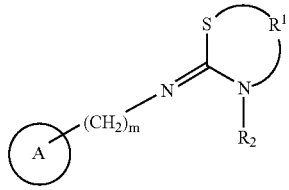

wherein $R^1$ is optionally substituted alkylene, $R^2$ is alkyl; a group of the formula: —C(=$R^5$)—$R^6$ wherein $R^5$ is O or S, $R^6$ is alkyl, alkoxy, alkylthio, optionally substituted amino, optionally substituted aralkyloxy, optionally substituted aralkylthio, optionally substituted aralkylamino, alkoxyalkyl, alkylthioalkyl or optionally substituted aminoalkyl; or a group of the formula: —$SO_2R^7$ wherein $R^7$ is alkyl, optionally substituted amino, optionally substituted aryl or optionally substituted heteroaryl, m is an integer of 1 to 2, A is optionally substituted aromatic carbocycle or optionally substituted aromatic heterocycle, a prodrug thereof, a pharmaceutically acceptable salt thereof or a solvate thereof.

2. The pharmaceutical composition according to claim 1 wherein the group of the formula:

is a group of the formula:

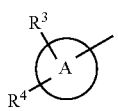

wherein $R^3$ and $R^4$ each is independently, hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl or a group of the formula: —C(=O)—$R^H$ wherein $R^H$ is hydrogen, alkyl, optionally substituted aryl or optionally substituted non-aromatic heterocyclic group, or $R^3$ and $R^4$ taken together may form alkylenedioxy, A is optionally substituted aromatic carbocycle or optionally substituted aromatic heterocycle.

3. The pharmaceutical composition according to claim 1 which has a binding activity to a cannabinoid type 2 receptor.

4. The pharmaceutical composition according to claim 3 which has an agonistic activity to a cannabinoid type 2 receptor.

5. The pharmaceutical composition according to claim 3 which is useful as an anti-inflammatory agent.

6. The pharmaceutical composition according to claim 3 which is useful as an immunosuppressive agent.

7. The pharmaceutical composition according to claim 3 which is useful as a nephritis treating agent.

8. A method for treating inflammation which comprises administering the pharmaceutical composition according to claim 1 to a patient in need thereof.

9. A method of immunosuppression which comprises administering the pharmaceutical composition according to claim 1 to a patient in need thereof.

10. A method for treating nephritis which comprises administering the pharmaceutical composition according to claim 1 to a patient in need thereof.

* * * * *